US009850549B2

(12) United States Patent
Sanford et al.

(10) Patent No.: US 9,850,549 B2
(45) Date of Patent: Dec. 26, 2017

(54) MONITORING TEMPERATURE WITH FLUORESCENCE

(71) Applicant: UNIVERSITY OF UTAH RESEARCH FOUNDATION, Salt Lake City, UT (US)

(72) Inventors: Lindsay N. Sanford, Salt Lake City, UT (US); Carl T. Wittwer, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 235 days.

(21) Appl. No.: 14/433,854

(22) PCT Filed: Oct. 8, 2013

(86) PCT No.: PCT/US2013/063939
§ 371 (c)(1),
(2) Date: Apr. 6, 2015

(87) PCT Pub. No.: WO2014/058919
PCT Pub. Date: Apr. 17, 2014

(65) Prior Publication Data
US 2015/0247209 A1  Sep. 3, 2015

Related U.S. Application Data

(60) Provisional application No. 61/711,631, filed on Oct. 9, 2012.

(51) Int. Cl.
*G01N 33/48* (2006.01)
*G01N 33/50* (2006.01)
*C12Q 3/00* (2006.01)
*G01K 11/20* (2006.01)
*G01N 21/64* (2006.01)
*B01L 7/00* (2006.01)
*C12Q 1/68* (2006.01)
*G01K 11/32* (2006.01)

(52) U.S. Cl.
CPC .............. *C12Q 3/00* (2013.01); *B01L 7/52* (2013.01); *C12Q 1/686* (2013.01); *G01K 11/20* (2013.01); *G01K 11/32* (2013.01); *G01N 21/6428* (2013.01); *B01L 2300/0636* (2013.01); *B01L 2300/18* (2013.01); *G01N 2021/6439* (2013.01)

(58) Field of Classification Search
None
See application file for complete search history.

(56) References Cited

U.S. PATENT DOCUMENTS

| 4,708,494 A | 11/1987 | Kleinerman |
| 5,196,709 A * | 3/1993 | Berndt ............... G01N 21/6408 250/458.1 |
| 5,788,374 A | 8/1998 | Bur et al. |
| 6,022,141 A | 2/2000 | Bass et al. |
| 6,140,054 A | 10/2000 | Wittwer et al. |
| 7,670,832 B2 | 3/2010 | Wittwer et al. |
| 2003/0128737 A1 | 7/2003 | Mcgrath et al. |
| 2004/0115632 A1* | 6/2004 | Mautner ............... C12Q 1/6858 435/6.11 |
| 2012/0231967 A1 | 9/2012 | Sood et al. |
| 2013/0157376 A1 | 6/2013 | Marion |
| 2014/0273181 A1 | 9/2014 | Abbott et al. |

FOREIGN PATENT DOCUMENTS

| CN | 101037541 | 9/2007 |
| DE | 102008056329 | 1/2010 |
| EP | 2313485 | 4/2011 |
| WO | 2004063342 | 7/2004 |
| WO | 2014058919 | 4/2014 |

OTHER PUBLICATIONS

Bruchhausen et al., "Instantaneous Measurement of Two-Dimensional Temperature Distributions by Means of Two-Color Planar Laser Induced Fluorescence (PLIF)," Exp. Fluids 38 (2005) 123-131.
Bruchhausen et al., "Temperature Measurements in Polydisperse Sprays by Means of Laser-Induced Fluorescence (LIF) on Three Spectral Bands," Automization and Sprays 16 (2006) 599-614.
Coppeta et al., "Dual Emission Laser Induced Fluorescence for Direct Planar Scalar Behavior Measurements," Exp. Fluids. 25 (1998) 1-15.
Defer et al., "Multicentre Quality Control of Polymerase Chain Reaction for Detection of HIV DNA," AIDS. 6 (1992) 659-63.
Erali et al., "High Resolution Melting Analysis for Gene Scanning," Methods. 50 (2010) 250-61.
Haff et al. "A High-Performance System for Automation of the Polymerase Chain Reaction," Biotechniques, 10 (1991), 102-3, 106-12.
He et al., "Effects of Thermocylcers and Primers on the Reproducibility of Banding Patterns in Randomly Amplified Polymorphic DNA Analysis," Mol. Cell. Probes. 8 (1994) 155-9.
Herrmann et al., "Amplicon DNA Melting Analysis for Mutation Scanning and Genotyping: Cross-Platform Comparison of Instruments and Dyes," Clin. Chem. 52 (2006), 494-503.
Hoelzel, "The Trouble with 'PCR' Machines," Trends Genet. 6 (1990) 237-8.
Huhmer et al., "Noncontact Infrared-Mediated Thermocycling for Effective Polymerase Chain Reaction Amplification of DNA in Nanoliter Volumes," Analytical Chemistry, 72 (2000) 5507-12.
Kopp et al., "Routine Monitoring of Temperature Inside Thermal Cycler Blocks for Quality Control," Clin. Chem. 40 (1994) 2117-9.

(Continued)

*Primary Examiner* — Russell S Negin
(74) *Attorney, Agent, or Firm* — Workman Nydegger

(57) ABSTRACT

Systems, methods, and kits are provided wherein a temperature-sensitive reagent that emits a luminescent signal is used to adjust the identification of the temperature of a sample or to control thermocycling. In various illustrative embodiments, the sample is a PCR mixture.

60 Claims, 18 Drawing Sheets

(56) References Cited

OTHER PUBLICATIONS

Lavieille et al., "Non-Intrusive Temperature Measurements Using Three-Color Laser-Induced Fluorescence," Exp. Fluids 36 (2004) 706-716.
Lavieille et al., Evaporating and Combusting Droplet Temperature Measurements Using Two-Color Laser-Induced Fluorescence, Exp. Fluids 21 (2001) 45-55.
Lavieille et al., "Temperature Measurements on Droplets in Monodisperse Stream Using Laser-Induced Fluorescence," Exp. Fluids 29 (2000) 429-437.
Lee et al., "Seven-Color, Homogeneous Detection of Six PCR Products," Biotechniques. 27 (1999) 342-9.
Lemoine et al., "Simultaneous Concentration and Velocity Measurements Using Combined Laser-Induced Fluorescence and Laser Doppler Velocimetry: Application to Turbulent Transport," Exp. Fluids 20 (1996), 319-327.
Lemoine et al., "Simultaneous Temperature and 2D Velocity Measurements in a Turbulent Heated Jet Using Combined Laser-Induced Fluorescence and LDA," Exp. Fluids 26 (1999) 315-323.
Liew et al., "Genotyping of Single-Nucleotide Polymorphisms by High-Resolution Melting of Small Amplicons," Clin. Chem. 50 (2004) 1156-64.
Linz, "Thermocycler Temperature Variation Invalidates PCR Results," Biotechniques. 9 (1990) 286, 288, 290-3.
Mondal et al., "In Situ Monitoring of Polymerase Extension Rate and Adaptive Feedback Control of PCR by Using Fluorescence Measurements," J. Biochem. Biophys. Methods. 65 (2005) 97-105.
Mondal et al., "Novel Fluorescence Detection Technique for Non-Contact Temperature Sensing in Microchip PCR," J. Biochem. Biophys. Methods. 70 (2007) 773-7.
Murray et al., "Fluorescence Methods for Determination of Temperature in Fuel Sprays," App. Opt. 24 (1985) 2783-7.
Palais et al., "Mathematical Algorithms for High-Resolution DNA Melting Analysis," Methods Enzymol. 454 (2009) 323-43.
Penner et al., "Reproducibility of Random Amplified Polymorphic DNA (RAPD) Analysis Among Laboratories," PCR Methods Appl. 2 (1993) 341-5.
Ririe et al., "Product Differentiation by Analysis of DNA Melting Curves During the Polymerase Chain Reaction," Anal. Biochem. 245 (1997) 154-60.
Ross et al., "Temperature Measurement in Microfluidic Systems Using a Temperature-Dependent Fluorescent Dye," Anal. Chem. 73 (2001) 4117-23.
Sakakibara et al., "Measurements of Thermally Stratified Pipe Flow Using Image-Processing Techniques," Exp. Fluids. 16 (1993) 82-96.
Sakakibara et al., Vortex Structure and Heat Transfer in the Stagnation Region of an Impinging Plant Jet (Simultaneous Measurements of Velocity and Temperature Fields by Digital Particle Image Velocimetry and Laser-Induced Fluorescence), International J. Heat Mass Transfer, 40 (1997), 3163-3176.
Sakakibara et al., "Whole Field Measurements of Temperature in Water Using Two-Color Laser Induced Fluorescence," Exp. Fluids. 26 (1999) 7-15.
Saunders et al., "Interlaboratory Study on Thermal Cycler Performance in Controlled PCR and Random Amplified Polymorphic DNA Analyses," Clin. Chem. 47 (2001) 47-55.
Schroder et al., "Novel Approach for Assessing Performance of PCR Cyclers Used for Diagnostic Testing," J. Clin. Microbiol. 43 (2005) 2724-8.
Schroder et al., "Physical Characteristics of Six New Thermocyclers," Clin. Chem. 49 (2003) 960-3.
Tweed et al., "Temperature Cycler Evaluation: What Do You Need to Know?" Biotechniques. 10 (1991) 526-30, 532.
Van Leuven, "The Trouble with PCR Machines: Fill Up the Empty Spaces!" Trends Genet. 7 (1991) 142.
Von Kanel et al., "Detecting and Resolving Position-Dependent Temperature Effects in Real-Time Quantitative Polymerase Chain Reaction," Anal. Biochem. 419 (2011) 161-7.
Von Keyserling et al., "The Use of Melting Curves as a Novel Approach for Validation of Real-Time PCR Instruments," Biotechniques, 51 (2011) 179-84.
Walker, "A Fluorescent Technique for Measurement of Concentration in Mixing Liquids," J. Phys. E: Sci. Instrum. 20 (1987) 217-24.
Wheeler et al., "Under-Three Minute PCR: Probing the Limits of Fast Amplification," Analyst. 136 (2011) 3707-12.
Wittwer et al., "Continuous Fluorescence Monitoring of Rapid Cycle DNA Amplification," Biotechniques, 22 (1997) 130-1, 134-8.
Wittwer, "Rapid Cycle DNA Amplification: Time and Temperature Optimization," Biotechniques, 10 (1991) 76-83.
Wittwer et al., "The Polymerase Chain Reaction," Springer-Verlag, Deerfield Beach, 1994, pp. 174-181.
Wittwer et al., "The PCR Revolution: Basic Technologies and Applications," Cambridge University Press, New York, 2010, pp. 48-69.
European Search Report for EP13846137 dated Mar. 4, 2016.
Han et al., "Fluorescent Indicators for Intracellular pH." Chem Rev. 110(05), May 12, 2010, p. 2709-28.
International Search Report and Written Opinion, United States Search Authority, PCT/US2013/063939, Completed Jan. 25, 2014.
International Preliminary Report on Patentability, United States Examining Authority, PCT/US2013/063939, Completed Sep. 8, 2014.
Islam et al., "Binding of DNA with Rhodamine B: Spectroscopic and molecular modeling studies," Dyes and Pigments 99, (2013), pp. 412-422.

* cited by examiner

Temperature (\C)

MONITORING TEMPERATURE WITH FLUORESCENCE

CROSS-REFERENCE TO RELATED APPLICATIONS

This application claims priority to and the benefit of PCT application No. PCT/US2013/063939, filed Oct. 8, 2013, entitled "MONITORING TEMPERATURE WITH FLUORESCENCE", which claims benefit of a priority to U.S. Provisional Application No. 61/711,631,filed Oct. 9, 2012, entitled "MONITORING TEMPERATURE WITH FLUORESCENCE DURING REAL-TIME PCR AND MELTONG ANALYSIS". All the aforementioned applications are incorporated by reference herein in their entirety.

GOVERNMENT LICENSE RIGHTS

This invention was made with government support under GM082116 awarded by the National Institutes of Health. The government has certain rights in the invention.

BACKGROUND

Polymerase chain reaction ("PCR") is a technique widely used in molecular biology. It derives its name from one of its key components, a DNA polymerase used to amplify a piece of DNA by enzymatic replication. Typically, PCR employs a thermostable polymerase, deoxynucleotide triphosphates ("dNTPs"), a pair of primers, and a template DNA. A single PCR reaction (or cycle) often involves (1) increasing the sample temperature to a temperature sufficient to melt or denature a double-stranded DNA molecule into single-stranded templates, (2) cooling the sample to allow a DNA primer to bind or anneal to each template, and optionally (3) re-adjusting the sample temperature to optimize the enzymatic addition of dNTPs onto a terminus of each bound primer to form a new DNA molecule. As PCR progresses, the generated DNA (the "amplicon") is itself used as a template for further replication. This sets in motion a chain reaction in which the DNA template is exponentially amplified. With PCR, it is possible to amplify a single or few copies of a DNA across multiple orders of magnitude, generating millions or more copies of the DNA.

Efficient PCR depends on accurately and reproducibly reaching product/template denaturation (or melting) and primer annealing temperatures during thermal cycling. This, in turn, depends on accurately measuring and controlling the sample and/or solution temperature. PCR sample temperature measurement and control can be performed manually or through automated instrumentation such as a thermal cycler (or thermocycler). Temperature sensors in many thermal cycling instruments measure the temperature of the metal block or air chamber surrounding the PCR tube that contains the amplification solution. With such "external" temperature sensors, accurate measurements can sometimes be obtained during equilibrium when the temperature is held constant. During temperature transitions, however, the solution temperature frequently lags behind the instrument block or chamber temperature, potentially leading to inaccuracy and inconsistency in temperature monitoring and control—an effect that becomes even more pronounced as the PCR cycling speeds increase.

Direct sensor contact within the PCR solution, while potentially more accurate than external temperature measurement, also can be problematic. Such direct, internal measurement of PCR is often disfavored because of product contamination, PCR inhibition, added thermal mass of the sensor, and obstruction of optical measurements. Many of these concerns become more acute as the sample volume decreases. In larger samples, however, direct physical sensors measure the temperature of only one location that may not accurately reflect the temperature of the entire solution.

Over time, temperature cycling for PCR has become faster. At faster speeds, most of the cycle time is spent in temperature transition, and the solution temperature seldom tracks the measured instrument temperature. Attempts to improve identifying the solution temperature during fast PCR cycling include prediction algorithms that depend on sample volume and sensors with the same thermal response as the samples so that they are kinetically matched. However, since the biochemical reactions in PCR are rapid and there are many ways to change the temperature of a sample quickly (especially small samples), the limiting factor for consistent PCR (especially at fast speeds) appears to be accurate temperature measurement.

BRIEF SUMMARY

The present invention extends to using luminescence to monitor the internal condition of a sample. One or more embodiments of the invention described herein include using one or more intrinsic luminescence properties of a condition-sensitive reagent to monitor the condition of a sample accurately. Certain embodiments include, for example, methods and systems that use the intrinsic luminescence of a pH- and/or temperature-sensitive reagent to monitor the temperature of a sample during PCR thermocycling and/or instrument calibration with improved accuracy. In at least one embodiment, the intrinsic fluorescence of a temperature-sensitive reagent changes as a function of temperature in a known and/or predictable manner. Accordingly, certain embodiments include using sample fluorescence as an internal temperature monitor to reflect the average temperature throughout a sample or to control thermocycling.

In an embodiment, a PCR mixture that includes at least one condition-sensitive reagent is described. The PCR mixture may include one or more reagents needed for performing PCR (e.g., at least one nucleic acid template, a plurality of nucleic acid primers that include at least one forward primer and at least one reverse primer configured to anneal to at least one portion of the at least one template nucleic acid, a thermostable polymerase, dNTPs, etc.) and the condition-sensitive reagent. In one embodiment the condition sensitive reagent may include at least one temperature-sensitive reagent capable of emitting a temperature-dependent luminescent signal in response to a stimulus. In at least one embodiment, the luminescent signal emitted from the at least one temperature-sensitive reagent has a fluorescent signal that changes by at least 50% between 95° C. and 50° C. For example, the at least one temperature-sensitive reagent may exhibit a temperature sensitivity of about 1%/° C. In at least one embodiment, the amount of luminescent signal emitted from the temperature-sensitive reagent is not directly proportional to an amount of nucleic acid present in the sample. For example, it is preferred that the temperature-sensitive reagent is not a dsDNA binding dye, the luminescent signal of the temperature-sensitive reagent is not affected by dsDNA denaturation (or melting), and/or the temperature-sensitive reagent is not tethered to a nucleic acid.

In another embodiment, a method of measuring the temperature of a sample is described. The method may include (1) providing a sample to be measured that includes a known amount of a temperature-sensitive reagent that emits a luminescent signal in response to a stimulus, wherein an amount of luminescent signal emitted by the temperature-sensitive reagent varies as a function of temperature in a known and predictable manner. The method further includes (2) measuring the amount of luminescent signal emitted from the temperature-sensitive reagent, and (3) determining the temperature of the sample as a function of the luminescent signal emitted by the temperature-sensitive reagent.

In certain embodiments, the temperature of the sample can be measured directly by observing the amount of luminescent signal emitted from the known amount of the temperature-sensitive reagent. In other embodiments, the temperature of the sample may be determined by (a) observing the amount of luminescent signal from the temperature-sensitive reagent at a first temperature, (b) observing the amount of luminescent signal from the temperature-sensitive reagent at a second temperature, and (c) determining the ratio of luminescent signal between the first and second temperatures.

In yet another embodiment, a method of calibrating a sample heating device is described. The method may include (1) providing a calibration sample that includes the temperature-sensitive reagent described above. The method may further include (2) measuring a device-determined temperature for the sample, (3) stimulating the temperature-sensitive reagent to induce emission of the luminescent signal therefrom, (4) measuring the amount of luminescence emitted from the temperature-sensitive reagent, and/or (5) measuring a luminescence-determined temperature of the calibration sample as a function of the luminescent signal emitted by the temperature-sensitive reagent. The method may also include (6) adjusting the device-determined temperature to reflect the luminescence-determined temperature. Illustratively, the temperature-sensitive reagent is a fluorescent dye.

Still other embodiments include a PCR system configured to employ temperature-dependent luminescence as an indication of internal sample temperature. The system may include (1) a sample vessel configured to receive a sample, (2) a sample temperature controlling device configured to manipulate the temperature of the sample, and/or (3) a sample temperature control mechanism configured to utilize the sample temperature controlling device to regulate the temperature of the sample. In at least one embodiment, the sample temperature controlling mechanism includes a sample temperature raising mechanism and a sample temperature lowering mechanism. The system may also include (4) a sample luminescence measuring element configured to quantify an amount of temperature-sensitive luminescence emitted by the sample. In at least one embodiment, the sample temperature control mechanism regulates the temperature of the sample based on sample luminescence.

Thus, in one illustrative embodiment, method are provided for measuring a temperature of a sample, the methods comprising providing a sample that includes a temperature-sensitive reagent that emits a luminescent signal in response to a stimulus; wherein an amount of luminescent signal emitted by the temperature-sensitive reagent changes as a function of temperature in a known manner; measuring the amount of luminescent signal emitted from the temperature-sensitive reagent; and determining a temperature of the sample as a function of the luminescent signal emitted by the temperature-sensitive reagent. In specific examples, the temperature-sensitive reagent comprises a fluorescent dye and the emitted luminescent signal comprises fluorescence. In other specific examples, the fluorescent dye comprises sulforhodamine B and the sample comprises a PCR mixture.

In other illustrative embodiments, methods of calibrating a sample heating device are provided, the methods comprising providing a sample that includes a temperature-sensitive reagent that emits a luminescent signal in response to a stimulus; wherein the luminescent signal emitted from the temperature-sensitive reagent changes as a function of temperature in a known and predictable manner, stimulating the temperature-sensitive reagent to induce emission of the luminescent signal therefrom; determining a luminescence-determined temperature of the sample based on the luminescent signal emitted by the temperature-sensitive reagent; determining a device-determined temperature for the sample; and adjusting a temperature setting of the sample heating device based on at least one of the luminescence-determined temperature and device-determined temperature.

In yet other embodiments, thermocycling systems are provided, the systems configured to employ temperature-dependent luminescence as an indication of average internal sample temperature comprising a sample vessel configured to receive a sample; a sample temperature controlling device configured to manipulate a temperature of the sample; a sample temperature control mechanism configured to utilize the sample temperature controlling device to regulate the temperature of the sample; wherein the sample temperature control mechanism comprises a sample temperature raising mechanism and a sample temperature lowering mechanism; and a sample luminescence measuring element configured to quantify an amount of temperature-sensitive luminescence emitted by the sample; wherein the sample temperature control mechanism regulates the temperature of the sample based on sample luminescence.

In still other illustrative embodiments PCR mixtures are provided, the PCR mixture comprising a temperature-sensitive reagent that emits a luminescent signal in response to a stimulus; wherein an amount of luminescent signal emitted from the temperature-sensitive reagent is not directly proportional to an amount of nucleic acid present in the sample; and wherein the temperature-sensitive reagent emits a fluorescent signal that changes between 95° C. and 50° C.

In additional illustrative embodiments, PCR kits are provided, the PCR kits comprising a temperature-sensitive reagent that emits a luminescent signal in response to a stimulus; and a perceivable protocol for using the temperature-sensitive reagent to determine the temperature of a sample.

In more illustrative embodiments, methods of controlling a thermocycling profile of a sample using feedback control are provided, the methods comprising providing a sample at a first temperature, wherein the sample includes a condition-sensitive reagent that emits a luminescent signal in response to a stimulus; stimulating the condition-sensitive reagent to induce emission of the luminescent signal therefrom; and detecting the luminescent signal emitted by the condition-sensitive reagent; wherein a predetermined value of the luminescent signal indicates an appropriate time to initiate a change to a next phase in the thermocycling profile.

In yet more illustrative embodiments, thermal cycling devices are provided, the thermal cycling devices configured to execute a thermocycling profile of a sample using feedback temperature control, comprising a sample vessel configured to receive a sample having at least one temperature-sensitive reagent that emits a luminescent signal in response to a stimulus, wherein the temperature-sensitive reagent comprises a passive reference reagent; a sample temperature controlling component configured to regulate a temperature of the sample and to initiate a change to a next phase in the thermocycling profile in response to a triggering event, where the triggering event comprises detection of a predetermined value of the luminescent signal.

Additional features and advantages of the embodiments of the invention will be set forth in the description that follows or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 6A illustrates the real-time amplification curve, while FIG. 6B illustrates negative derivative melting curves analyzed using the quantum method of background removal.

(FIG. 9A), 80° C. (FIG. 9B), and 50° C. (FIG. 9C) on three different instruments.

DETAILED DESCRIPTION

I. Introduction and Definitions

Figure 1:
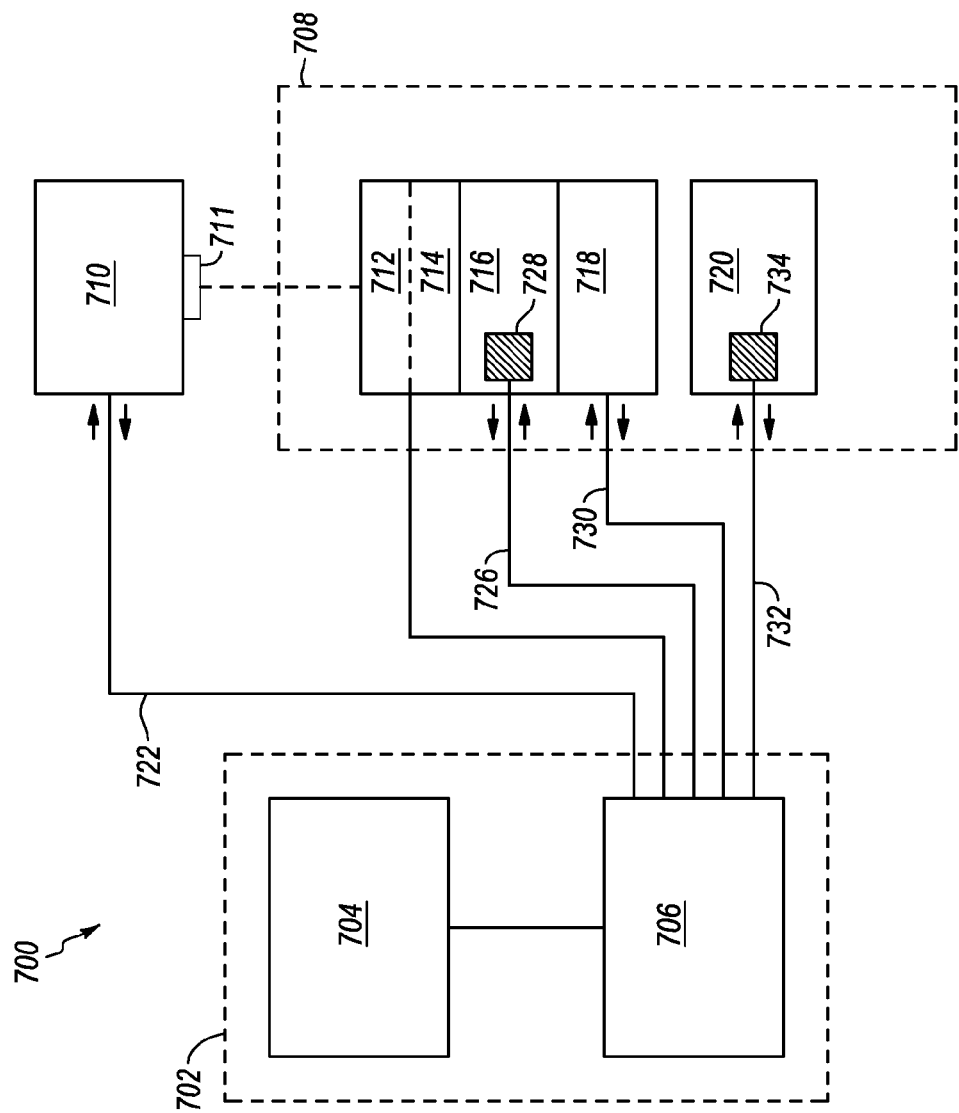
FIG. 1 illustrates a block diagram of an exemplary embodiment of a thermal cycling system in accordance with aspects of the disclosure.

The present invention extends to using luminescence to monitor an internal condition of a sample. One or more embodiments of the invention described herein include using intrinsic luminescence properties of a condition-sensitive reagent to monitor the condition of a sample accurately. Certain embodiments include, for example, methods and systems that use the intrinsic luminescence of a pH- and/or temperature-sensitive reagent to monitor accurately the temperature of a sample during PCR thermocycling and/or instrument calibration. In at least one embodiment, the intrinsic fluorescence of a temperature-sensitive reagent changes as a function of temperature in a known and/or predictable manner. Accordingly, certain embodiments include using sample fluorescence as an internal temperature monitor to reflect the average temperature throughout a sample or to control thermocycling.

As used herein, "nucleic acid," "template nucleic acid" and similar terms include "nucleotide(s)," "oligonucleotide(s)," and "DNA(s)," as well as RNA(s), nucleic acid analogs, and nucleic acid substitutes, (i.e. naturally occurring or synthetic analogs, substitutes, or equivalents; for example, those having other than a phosphodiester backbone), whether single-stranded, double-stranded, or otherwise configured. Illustrative examples of such substitutes, including the so called "peptide nucleic acids" (PNAs) and the so called "locked nucleic acids" (LNAs), as well as non-analogous nucleic acid substitutes are also included herein. Where appropriate, such terms may also include one or more dNTPs.

As used herein, "dNTP" and similar terms also include deoxyribonucleotide and/or deoxyribonucleotide triphosphate analogues, substitutes, equivalents and the like as previously discussed. Where appropriate, "dNTPs" and similar terms may also include other nucleotides and/or nucleotide triphosphates (NTPs), including ribonucleotides and/or ribonucleotide triphosphates and their analogues, substitutes, equivalents and the like as previously discussed. Furthermore, nucleosides and nucleotides are both contemplated herein.

As used herein, "base pair," "base pairing," and similar terms refer to the association of complementary nucleic acids as previously defined and are not limited to canonical Watson-Crick base pairing or association via hydrogen bonding.

As used herein, "double-stranded" refers to the base pairing of at least one pair of nucleic acids, as previously defined, and is not limited to nucleic acids of any particular length or base pairs from separate nucleic acid strands.

As used herein, "primer," "nucleic acid primer," and similar terms may also refer to a group, collection, plurality, and/or set of primers.

While PCR is the method used in the examples herein that requires temperature control, it is understood that any amplification, non-amplification, or other analysis and/or method in which temperature control is important may benefit by the invention. Illustrative amplification procedures include polymerase chain reaction (PCR); strand displacement amplification (SDA); nucleic acid sequence-based amplification (NASBA); cascade rolling circle amplification (CRCA); target based-helicase dependent amplification (HDA); transcription-mediated amplification (TMA), and the like. Therefore, when the term PCR is used, it should be understood to include other alternative amplification and non-amplification analysis and/or methods. Other illustrative analysis methods that may benefit by the invention include melting analysis, high resolution melting analysis, and isothermal amplification methods that require close temperature control. It is also understood that methods according to certain embodiments described herein may use nucleic acids obtained from other sources, including naturally occurring and synthetic nucleic acids.

As used herein, "sample plate," "sample container," and similar terms refer to a receptacle comprising at least one sample vessel or compartment, and does not necessarily imply the presence of a sample, known or unknown, within the sample vessel(s) thereof. Non-limiting examples of illustrative configurations include single vessel (Eppendorf) tubes, 8-tube strips, 12-tube strips, 48-well plates, 96-well plates, 384-well plates, 1536-well plates. Furthermore, use of a multi-well sample plate or a multi-tube strip herein is illustrative only. Additional illustrative examples of sample containers, including sample tubes, capillaries, flexible pouches, arrays, carousels, and the like are known in the art and are also included herein.

As used herein, "sample vessel," "sample compartment," "sample well," and similar terms refer to at least a portion or partition of a receptacle that is configured to provide a barrier that limits fluid communication between adjacent portions or partitions, and does not imply the presence of a sample, known or unknown, within the sample vessel, compartment, or well. Non-limiting, illustrative examples include wells or tubes of a sample plate or tube strip, blisters formed in a sample pouch, individual capillary tubes, and similar compartments.

As used herein, "condition-sensitive reagent," "condition-dependent reagent," and similar terms refer to any molecule, component, chemical, compound, dye, and/or other material whose property or properties change as a function of at least one condition and/or physical or other property and that is thereby capable of directly or indirectly demonstrating, suggesting, or revealing an actual, experimental, or approximate condition and/or physical or other property.

In certain embodiments, the condition-sensitive reagent may emit a luminescent signal in response to a stimulus. For example, the condition-sensitive reagent may include a temperature-sensitive fluorescent dye that emits a fluorescent signal in response to exposure to a stimulus (illustratively, light having a given wavelength) sufficient to excite or otherwise induce emission of a fluorescent signal from the dye.

It is noted, however, that reference to fluorescence and/or fluorescent reagents is illustrative only, and that non-fluorescent forms of luminescence are also contemplated within the scope of this invention. For example, chemiluminescence, bioluminescence, radio luminescence, electroluminescence, electrochemiluminescence, mechanoluminescence, crystalloluminescence, thermoluminescence, sonoluminescence, phosphorescence and other forms of photoluminescence, and the like are contemplated herein.

In addition, condition-sensitive reagents that respond to non-electromagnetic stimuli are also contemplated within the scope of this disclosure. Indeed, a condition sensitive reagent may include any reagent that responds to any suitable condition and/or physical or other property and that emits an amount of luminescent signal in response to a stimulus. Accordingly, any stimulus capable of stimulating such a luminescent response is contemplated within the scope of this disclosure. Therefore, a radioluminescent reagent that emits a temperature-sensitive or temperature-dependent signal (or amount of signal) in response to a stimulus (including ionizing radiation such as beta particles) is contemplated herein.

Thus, while for convenience, reference may be made to a particular form of luminescence and/or luminescent reagents and/or a corresponding stimulus for the same (such as fluorescence, fluorescent dye, and electromagnetic radiation, illustratively); all forms of luminescence, condition-sensitive and/or luminescent reagents, and corresponding stimuli are contemplated herein.

It is also noted that reference to temperature, temperature-dependence, temperature-sensitivity, and/or the use of temperature-dependent and/or temperature-sensitive reagents is illustrative only. For instance, the condition-sensitive reagents described in the systems, compositions, and methods disclosed herein may be sensitive to pH changes, ion or ionic strength changes, as well as changes in viscosity, density, specific gravity and other forms of physical and/or other property changes and/or corresponding reagents; all of which are contemplated within the scope of this disclosure. Thus, while for convenience, reference may be made to a particular condition, condition-sensitivity, condition dependence, and/or condition-sensitive and/or condition-dependent reagent (such as temperature, illustratively); all conditions, condition-sensitivity, condition dependence, and/or condition-sensitive and/or condition-dependent reagents are contemplated herein.

Condition-sensitive reagents may also include, illustratively, nucleic acid(s), protein(s), probe(s), and/or other molecule(s) with one or more bound, tethered, conjugated, and/or otherwise associated indicators of a condition and/or physical or other property, such as dyes, molecules, moieties, units, and so forth. Furthermore, reagents sensitive to a first condition and/or physical or other property (such as pH, illustratively), which may change as a function of a second condition and/or physical or other property (such as temperature, illustratively) are also included herein. In one aspect, the condition-sensitive reagent may not bind one or more nucleic acids with substantial specificity and/or may not display a substantial change in luminescence signal and/or emission upon binding one or more nucleic acids. As used herein, "binding" a nucleic acid may also refer to intercalating into and/or between nucleic acid secondary, tertiary, and/or quaternary structure, or minor groove binding.

As used herein, "passive reagent," "passive reference reagent," "passive dye," "passive reference dye," and similar terms refer to a condition-sensitive reagent that emits a luminescent signal in response to a stimulus, and (1) that does not inhibit and/or interfere with PCR and/or PCR product formation and/or (2) wherein the amount of luminescent signal emitted from the condition-sensitive reagent is not indicative of an amount of a nucleic acid present in a sample. In one aspect, the condition-sensitive reagent constituting the passive dye, passive reference dye, etc. may not bind one or more nucleic acids with substantial specificity and/or may not display a substantial change in luminescence signal and/or emission upon binding one or more nucleic acids.

As used herein, "temperature-sensitive," "temperature-dependent," and similar terms refer to a property, characteristic, and/or tendency of any reagent, matter, element, or other material to indicate a change in temperature in a perceivable manner or otherwise respond to a change in temperature.

As used herein, "quantitative indicator of PCR product formation" and similar terms refer to any molecule, component, chemical, compound, dye, reagent and/or other material that is capable of demonstrating, suggesting, or otherwise revealing an actual, experimental, or approximate quantity of PCR product in a sample, solution, suspension, and/or reaction mixture. One illustrative example is a dsDNA binding dye or other dsDNA-binding reagent. Such an indicator may also illustratively include a nucleic acid, protein, probe, and/or other molecule with one or more bound, tethered, conjugated, and/or otherwise associated indicators of PCR progress, such as dyes, molecules, moieties, units, and so forth.

As used herein, "device-determined temperature," "instrument temperature" and similar terms refer to a temperature measured, quantified, observed, determined, or otherwise ascertained by a device, instrument, element, member, hardware, sensor and/or other matter designed to perform the same without necessarily contacting the measured matter directly and/or by measuring temperature(s) external to the measured matter (i.e., an external temperature of the measured matter).

As used herein, "thermocouple-determined temperature," "thermocouple temperature," "temperature measured through direct contact," and similar terms refer to a temperature measured, quantified, observed, determined, or otherwise ascertained by contacting the measured matter with a temperature measuring device.

As used herein, "solution temperature," "luminescence-determined temperature," "fluorescence-determined temperature," and similar terms refer to a temperature measured, quantified, observed, determined, or otherwise ascertained through the use of a condition-sensitive reagent.

As used here, "thermal cycling profile," "thermocycling profile," and similar terms refer to any process, procedure, method, strategy, or other plan of action by which a sample or sample temperature is regulated and/or manipulated from a first temperature to at least a second temperature. Such profiles may be accomplished manually or via automation, including software or other programs configured to accomplish the same. In one aspect, such profiles may include multiple rounds of cycling through a plurality of temperatures. For instance, in an illustrative PCR or other profile, the plurality of temperatures may include at least one "melting" temperature, and at least one "annealing" temperature, wherein the melting temperature is higher than the annealing temperature, and the profile may include cycling through the melting and annealing temperatures one or more times. In certain aspects, a profile may include a third "elongation" temperature, illustratively between the melting and annealing temperatures. In addition, profiles generally involve several phases, including (1) at least one ramp or ramping period in which the sample temperature is changed from the first temperature to at least the second temperature, wherein each ramp or ramping period is configured with at least one ramp or ramping rate or speed at which the temperature is changed, and (2) at least one hold or holding period in which the sample temperature is held or otherwise kept substantially constant or otherwise unchanged, wherein the hold or holding period(s) are greater than or equal to zero seconds.

II. PCR Mixtures

A PCR mixture that includes at least one condition-sensitive reagent is described. The PCR mixture may include one or more reagents needed for performing PCR (e.g., at least one nucleic acid template, a plurality of nucleic acid primers that include at least one forward primer and at least one reverse primer configured to anneal to at least one portion of the at least one template nucleic acid, a thermostable polymerase, dNTPs, etc.) and the condition sensitive reagent.

In at least one embodiment, the condition-sensitive reagent includes a temperature sensitive reagent. The temperature sensitive reagent may produce a detectable signal (e.g., a luminescence signal and/or emission) in response to a stimulus, wherein the amount of the signal produced by the temperature sensitive reagent changes in response to changes in the temperature of a medium in which the temperature sensitive reagent is included. In one embodiment, the temperature-sensitive reagent may not bind one or more nucleic acids with substantial specificity and/or may not display a substantial change in luminescence signal and/or emission upon binding one or more nucleic acids, and/or the amount of luminescent signal emitted from the temperature-sensitive reagent is not indicative of an amount of a nucleic acid present in the sample. Furthermore, in certain embodiments, the PCR mixture may include a passive reference dye.

In certain embodiments, the amount of luminescent signal emitted by and/or from the temperature-sensitive reagent may change as a function of temperature in a known and/or predictable manner. For instance, temperature-dependent and/or temperature-sensitive changes in the amount of fluorescent signal emitted from a temperature-sensitive passive dye may have been previously studied, determined, concluded, and/or recorded.

In at least one embodiment, a temperature-sensitive reagent emits a luminescent signal that changes by a measurable amount within a defined temperature range. For example, the temperature-sensitive reagent may emit a luminescent signal that changes by about (or at least) 50% between about 95° C. and about 50° C. One will appreciate, however, that certain embodiments may include a temperature-sensitive reagent that emits a luminescent signal that changes by other amounts, including by a factor less than 50% between about 95° C. and about 50° C. Similarly, signal changes of about (or at least) 5%, 10%, 20%, 40%, 60%, 80%, or 100% between about 95° C. and about 50° C. are contemplated herein. It is understood that the signal change may be an increase or decrease, and if the signal change is an increase, a change of more than 100% is also contemplated.

Likewise, the temperature range in which the luminescent signal emitted by the temperature-sensitive reagent changes by a measurable amount, or by a specific or pre-determined factor or percentage, may be larger or smaller than between two or more selected temperature points (e.g., between about 95° C. and about 50° C.). For instance, the luminescent signal may increase by about 50% or more between about 50° C. and about 0° C., between about 75° C. and about 55° C., between about 95° C. and about 65° C., between about 95° C. and 45° C., between about 65° C. and about 32° C., or between any temperature ranges compatible with the use of such a reagent.

In at least one illustrative embodiment, the fluorescent signal emitted from the temperature-sensitive reagent at certain illustrative wavelength(s) changes by about 1%/° C. in a relevant temperature range. For example, a temperature-sensitive reagent may have and/or display a temperature sensitivity of about 1%/° C. between about 95° C. and about 50° C. at certain illustrative wavelength(s). Furthermore, temperature-sensitive and/or temperature-dependent signal changes of less than 1%/° C. and greater than 1%/° C. are also contemplated herein.

It is noted that signal changes may include signal increases, signal decreases, or other signal changes characteristic to the reagent. While different reagents or dyes, illustratively, may react differently to temperature changes, the fluorescence of most fluorescent dyes decrease as temperature is increased.

In certain embodiments, the luminescent signal emitted by the temperature-sensitive reagent changes in a substantially linear fashion or manner relative to (or dependent upon) sample temperature. In other illustrative embodiments, exponential, sigmoidal, logarithmic, logistic, and other mathematically-defined curve fits (including derivatives or other calculations or modifications) may substantially define the temperature-sensitive and/or temperature-dependent change in reagent luminescence and/or luminescent signal emission in a relevant temperature range. Illustratively, observation of the linearity of luminescent signal change may require or otherwise be subject to an initial "warm up" period for a luminescence signal detecting element or device.

In certain embodiments, the temperature-sensitive reagent may exhibit a thermal degradation of less than or equal to about 2.2% per hour at about 80° C. and/or about 5.4% per hour at about 94° C. One will appreciate, however, that some illustrative temperature-sensitive reagents may exhibit higher degrees of thermal degradation without departing from the scope of this disclosure. An illustrative reagent may also exhibit substantial thermal stability (i.e. absence of substantial thermal degradation within a relevant margin of error) at about 50° C. for up to 1 hour or more. One will appreciate, however, that thermal stability may be both temperature- and reagent-specific, and that variations in thermal stability between reagents may not necessarily render any specific reagent unacceptable or otherwise disfavored. Illustratively, dyes exhibiting thermal degradation at higher temperatures may be acceptable if rapid cycling is used and the dyes are not held at the higher temperatures for any significant period of time.

Likewise, illustrative temperature-sensitive reagents may exhibit negligible, measurable, or even substantial luminescence quenching at relevant temperature(s), within a relevant time frame, without departing from the scope of the invention. For instance, in at least one embodiment, the temperature-sensitive reagents may exhibit no substantial, appreciable, and/or apparent fluorescence quenching over about one hour at about 50° C. Furthermore, in certain embodiments, the absence of substantial fluorescence quenching may be exhibited irrespective of whether the samples are continuously illuminated or only illuminated periodically. One will appreciate, however, that luminescence quenching may be time-, temperature- and/or reagent-specific, and that variations in fluorescence quenching properties between reagents may not necessarily render any specific reagent unacceptable or otherwise disfavored.

In a specific illustrative example, the temperature-sensitive reagent included in the PCR mixture may include sulforhodamine B. Sulforhodamine B is relatively stable under temperature cycling conditions and produces known and predictable changes in fluorescence as a function of temperature. In addition, sulforhodamine B may be classified as a passive reference dye at least insofar as (1) it does not inhibit and/or interfere with PCR and/or PCR product formation and/or (2) the amount of luminescent signal emitted therefrom is not indicative of an amount of a nucleic acid present in a sample. The fluorescence signal (measured at about 514 nm, illustratively) of sulforhodamine B decreases by about 1.55% for each 1° C. increase when excited at 514 nm. Although the most efficient excitation for sulforhodamine B is at 560 nm, a common excitation wavelength of 470-483 nm may be used in certain illustrative embodiments (e.g., to compare across instruments). Under these conditions, a temperature sensitivity of 1.19%/° C. may be observed. It is understood that the lower excitation efficiency at these wavelengths may be compensated by a higher concentration of sulforhodamine B than may typically be used to maintain signal and limit noise.

Reference to sulforhodamine B, however, is illustrative only and is not meant to limit the scope of reagents disclosed herein. In certain embodiments, any suitable condition-sensitive reagent that exhibits the qualities necessary for the scope of use may be sufficient. Thus, when a temperature-sensitive passive dye that exhibits (1) a substantially linear increase of about 50% in fluorescent between about 95° C. and about 50° C. (approximately 1%/° C.), and/or (2) thermal degradation averages of about 2.2% per hour at about 80° C. and 5.4% per hour as about 94° C., and/or (3) no appreciable fluorescence quenching at about 50° C. for 1 hour is desirable, a reagent such as sulforhodamine B, which exhibits such properties, may be favorable. Likewise, if about a 60% increase in fluorescent or luminescent signal between about 95° C. and about 50° C. is desired, a reagent such as fluorescein, which exhibits such properties, may be used. Non-limiting examples of other fluorescent dyes include eosin B, ethyl eosin, and snarf-1. However, it is understood that various other condition-sensitive reagents and/or temperature-sensitive passive dyes may be used.

Some embodiments of the present invention may also include at least one template nucleic acid. Furthermore, in certain embodiments, the template nucleic acid may include any number of nucleotides sufficient to function as a template for PCR and need not be any minimum or maximum length.

A PCR mixture according to at least one embodiment of the present invention may also include a plurality of nucleic acid primers (e.g., at least one forward primer and at least one reverse primer). For instance, certain illustrative PCR mixtures may include a pair of (i.e., two kinds of, types of, sets of, and/or separate sequence-defined) nucleic acid primers. In some embodiments, each kind of primer may be configured to anneal to a separate strand of template nucleic acid, and may be provided in equal or different concentrations, as is known in the art. Certain embodiments of the present invention may also include one or more dNTPs.

Some embodiments of the present invention may also include a nucleic acid polymerase configured to incorporate one or more dNTPs onto a terminus of a nucleic acid primer and/or nascent nucleic acid or chain. One will appreciate, however, that certain embodiments may include an RNA polymerase, transcriptase, reverse transcriptase, ligase or other enzyme configured to perform a predetermined molecular or other function. For example, some illustrative embodiments may include a control or substitute enzyme not configured to incorporate dNTPs or other molecules onto a primer and/or nascent nucleic acid or chain.

Certain illustrative embodiments may further include a quantitative indicator of PCR product formation. Such an indicator may include a dsDNA-binding dye or other reagent. In at least one embodiment, the luminescence emission of the quantitative indicator of PCR product formation may not entirely overlap the luminescence of a temperature-sensitive reagent. For example, in certain illustrative embodiments, the signal from a passive dye can be spectrally separated from fluorescent channels that are used to monitor the progress of the PCR, allowing both target production and temperature to be monitored by fluorescence.

Furthermore, certain embodiments may contain one or more additional reagents configured for normalization of instrument optics. For example, an additional fluorescence reference dye may be included in certain illustrative embodiments. In some embodiments, the additional reagent may also (or alternatively) directly and/or indirectly indicate a quantity of the mixture or a reagent added to the mixture.

In some embodiments, the PCR mixture(s), sample(s), and/or one or more reagents described herein may be provided in or as a solution, dissolved in a solvent, and/or otherwise in liquid form. In at least one embodiment, the reaction mixture(s), sample(s), and/or one or more of the reagents are provided in freeze-dried, lyophilized, gelatinous, or in solid and/or semi-solid form. Indeed, such matter may be provided in any form or physical state compatible with the same. Furthermore, reagents may be provided in any combination and, in certain embodiments, as a kit containing some or all of the materials, components and/or reagents necessary for a user to then add one or more reaction-specific materials, components, and/or reagents, thereby completing a recipe, formula, or list of reagents necessary and/or sufficient for successful PCR.

Some embodiments may also include instruction(s) and/or protocol(s) for using the condition-sensitive reagent. In certain embodiments, the instructions may describe, detail, outline, or otherwise provide a method of measuring, calculating, or otherwise determining a temperature, condition, and/or physical or other property of a sample, a method of calibrating a sample-heating, thermocycling, or other device or system, and/or any other compatible method of use for said condition-sensitive reagent.

It is noted that a PCR mixture according to an embodiment of the present invention may include, incorporate, or otherwise comprise properties, reagents, steps, components, members, and/or elements described in other systems, methods, and/or mixtures disclosed herein.

III. PCR Systems

Certain embodiments of the present invention may also involve or include a PCR system configured to employ or otherwise utilize the temperature-sensitive luminescence of a temperature-sensitive reagent as an indication or indicator of (internal) sample temperature.

Referring to FIG. 1, a block diagram of an illustrative system 700 that includes control element 702, a thermocycling element 708, and an optical system 710 according to exemplary aspects of the disclosure is shown.

In at least one embodiment, the system may include at least one sample vessel 714. In certain embodiments, the sample vessel may include one or more samples 712. An illustrative sample 712 may include a PCR mixture configured to permit and/or effect amplification of a template nucleic acid. Certain illustrative embodiments may also include at least one sample block or chamber 716 configured to receive the at least one sample vessel 714. The sample vessel 714 may include one or more individual sample vessels in individual, strip, plate, or other format, and, illustratively, may be provided as or received by a sample block or chamber 716.

One or more embodiments may also include sample temperature controlling devices 718, 720 configured to manipulate and/or regulate the temperature of the sample(s). Such a sample temperature controlling device may be configured to raise, lower, and/or maintain the temperature of the sample(s). In one example, sample controlling device 718 includes a heating system and sample controlling device 720 includes a cooling system. Illustrative sample temperature controlling devices include (but are not limited to) heating and/or cooling blocks, elements, exchangers, coils, radiators, refrigerators, filaments, induction heaters, irradiative heating (including IR heating), Peltier devices, forced air blowers, handlers, vents, distributors, compressors, condensers, water baths, ice baths, flames and/or other combustion or combustible forms of heat, hot packs, cold packs, dry ice, dry ice baths, liquid nitrogen, microwave- and/or other wave-emitting devices, means for cooling, means for heating, means for otherwise manipulating the temperature of a sample, and/or any other suitable device configured to raise, lower, and/or maintain the temperature of the sample(s). It is understood that in some embodiments a single temperature controlling device may operate as both a heating system and a cooling system.

Certain embodiments of the PCR system may also include an optical system 710 configured to detect an amount of luminescence and/or temperature-sensitive luminescence emitted by the sample 712 (or a portion or reagent thereof). Such an optical system 710 may include an optical member configured to query the luminescence of the sample 712. Illustrative optical systems include single- and multi-channel fluorimeters.

At least one embodiment further includes a CPU 706 that functions in part as a sample temperature control or controlling mechanism. In certain embodiments, the sample temperature control or controlling mechanism may regulate the temperature controlling devices 718, 720 via connections 730, 732 to adjust the temperature of the sample 712 based on sample luminescence and/or any value calculated therefrom. For instance, the mechanism may effect a temperature change in response to a specific and/or predetermined amount or level of sample luminescence detected by the optical system 710 and/or an optical member or element 711 thereof. The mechanism may also (or alternatively) regulate temperature controlling devices 718, 720 to adjust the temperature of the sample 712 based on measurable and/or determinable factors other than luminescence, including sample temperature, sample pH, and the like, which may be calculated and/or determined from (at least) sample luminescence. Such a mechanism may involve utilizing one or more sample temperature controlling devices 718, 720 following detection and/or quantification of a predetermined amount or level of luminescence (e.g., temperature-sensitive fluorescence) and/or other measurable and/or determinable factor(s).

In at least one embodiment of the PCR system 700, the CPU 706 may execute instructions or be programmed or configured to operate, control, execute, or otherwise advance at least the sample temperature controlling mechanism based on sample luminescence or a value or parameter calculated therefrom, or to run or otherwise execute software designed to perform the same. Manual, mechanical, electrical, and/or other methods and/or devices configured to operate and/or otherwise affect the sample temperature controlling mechanism are also contemplated herein. For example, a mechanical or electrical trigger configured to alternate the positioning of the sample vessel or sample container 714 between a sample temperature controlling device 718 configured to raise the temperature of a sample 712 and a sample temperature controlling device 720 configured to lower the temperature of a sample 712 in response to detection and/or quantification of predetermined amounts of sample luminescence by the optical system 710 and/or optical element 711 (or a parameter calculated therefrom) is contemplated within the scope of this invention. The CPU 706 may accept input from or provide output to a user interface or terminal 704.

Certain illustrative embodiments of a PCR system may further include at least one sample temperature measuring device 728 or 734. Such a device may include a thermometer, thermistor, thermocouple, or other device capable of measuring a sample temperature. The sample temperature measuring device 728, 734 may be configured to measure the internal sample temperature directly (through direct contact with the sample 712) or measure an external temperature for the sample 712 (without directly contacting the sample 712) and may provide data to CPU 706 via connection 726, 732. Such indirect contact may involve measuring the temperature of a sample vessel or container 714, heating and/or cooling sources such as temperature controlling devices 718, 720, sample vessel or container receiving member or receptacle, and/or any other indicator of sample temperature. In some embodiments, sample temperature may be inferred from the temperature of associated members and/or elements such as a heating or cooling block or chamber, such as sample block or chamber 716. It is also understood that in some embodiments sample temperature controlling devices 718, 720 may receive input directly from one or more temperature measuring devices 728 or 734 or optical system 710, and may operate automatically based on one or more of the device-determined temperature, the thermocouple-determined temperature, or the solution temperature, with or without going through the CPU 706.

Additional examples of illustrative features, components, elements, and or members of illustrative PCR systems and/or thermal cyclers (thermocyclers) are known in the art and/or described in U.S. patent application Ser. No. 13/834,056, the entirety of which is herein incorporated by reference.

It is noted that a PCR system according to an embodiment of the present invention may include, incorporate, or otherwise comprise properties, reagents, steps, components, members, and/or elements described in other systems, methods, and/or mixtures disclosed herein.

IV. Methods of Measuring a Temperature

Certain embodiments of the present invention may include methods of measuring, calculating, or otherwise determining a temperature, condition, or physical, or other property of a sample. In at least one embodiment, the method may include providing a sample that includes at least one condition-sensitive reagent that emits a luminescent signal in response to at least one stimulus. In some embodiments, the amount of luminescent signal emitted by a temperature-sensitive reagent may be used to measure, calculate, or otherwise determine a luminescence-determined temperature for the sample. For example, the temperature-sensitive reagent may include sulforhodamine B, fluorescein, and/or any other fluorescent dye that emits a temperature-sensitive fluorescent signal in response to exposure to light having a given wavelength.

In at least one embodiment, a dedicated sample containing the fluorescent temperature-sensitive dye can be monitored to control cycling during PCR. Other embodiments may involve adding the fluorescent dye directly to a PCR mixture so that real-time amplification and temperature monitoring for cycling control may be conducted simultaneously for each sample or zone individually. This is attractive as well-to-well variation and temperature validation can be conducted on a run-by-run basis. In the case where the fluorescent-dye for temperature monitoring is added directly to the PCR mixture, color compensation may be required due to spectral overlap as discussed further in U.S. Pat. No. 6,140,054, the entirety of which is herein incorporated by reference.

One will appreciate that reference to a single sample, reagent, or condition is illustrative only. Certain embodiments may include providing a plurality of substantially identical or non-identical samples. Such samples may include sample replicates, positive and/or negative control samples, and/or independent sample variants. Likewise, a sample according to certain illustrative embodiments may include a plurality of temperature-sensitive reagents. At least one of such reagents may include and/or represent a control reagent. Furthermore, the sample may include a PCR mixture, illustratively.

In at least one embodiment, the method may further include stimulating the temperature-sensitive reagent sufficiently to induce the luminescent signal. For example, an embodiment may include stimulating a fluorescent dye with electromagnetic radiation or light having a given wavelength sufficient to induce emission of a fluorescent signal.

In certain embodiments, the amount of luminescent signal emitted from the temperature-sensitive reagent changes as a function of temperature and/or another condition or property in a known and/or predictable manner. Certain embodiments may also (or alternatively) include the determination of such temperature-sensitive changes.

Certain embodiments may also include measuring the amount of luminescent signal emitted from the temperature-sensitive reagent. Such measuring may include detecting and/or quantifying the emitted luminescent signal such that a sample and/or solution temperature may be determined, calculated, and/or inferred therefrom. Thus, certain illustrative embodiments may also include determining the temperature of the sample as a function of at least the luminescent signal emitted by the condition-sensitive reagent.

In certain illustrative embodiments, the determination of sample temperature as a function of luminescent signal may include comparing the measured amount of luminescent signal emitted from the sample and/or reagent to a standard for amounts of luminescent signal emitted by that reagent at various temperatures to determine the temperature at which the reagent is known to emit the measured amount of luminescent signal. One will appreciate, however, that the determination of sample temperature as a function of luminescent signal may include comparing the measured amount of luminescent signal emitted from the reagent to a standard for amounts of luminescent signal emitted by the reagent as a function of some other physical or other property (e.g., pH), that may change as a function of temperature, to determine the temperature at which the reagent is known to emit the measured amount of luminescent signal.

In at least one embodiment, the temperature of the sample can be measured directly by observing or otherwise detecting the amount of luminescent signal emitted from a known amount of temperature-sensitive reagent present in the sample. In another embodiment, the temperature of the sample may be determined by calculating the ratio of two different fluorescent signals, wherein one signal is generally temperature sensitive and the second signal is generally temperature insensitive. In one such embodiment, the temperature is calculated by at least (a) observing or otherwise detecting the amount of luminescent signal emitted from the temperature-sensitive reagent at a first wavelength, wherein the signal from the temperature-sensitive reagent is temperature sensitive at the first wavelength, (b) observing or otherwise detecting the amount of luminescent signal emitted from the temperature-sensitive reagent at a second wavelength, wherein the signal from the temperature-sensitive reagent is less temperature sensitive at the second wavelength, and (c) determining the ratio of luminescent signal at the first and second wavelengths. In another such embodiment, the temperature is calculated by at least (a) observing or otherwise detecting the amount of luminescent signal emitted from the temperature-sensitive reagent, (b) observing or otherwise detecting the amount of luminescent signal emitted from a second reagent that is generally temperature insensitive, and (c) determining the ratio of luminescent signal from the two reagents. Because fluorescent ratios from at least two signals are being compared, as opposed to observing or otherwise detecting the absolute fluorescence, it may not be necessary that the amount of the temperature-sensitive reagent in the sample be known in certain embodiments.

Some embodiments may include measuring the temperature of the sample by at least one other method. For instance, an embodiment may include measuring a device-determined temperature and/or a thermocouple-determined temperature for the sample. In certain embodiments, the difference or variance between a reagent luminescence-determined temperature and a device- or thermocouple-determined temperature is (or is known to be) less than or equal to about 1 degree Celsius. For example, the amount of fluorescence emitted by a temperature-sensitive reagent such as sulforhodamine B may be used to calculate or otherwise determine a luminescence-determined temperature for a PCR mixture within about 1 degree Celsius of a thermocouple-measured temperature of the sample. In certain embodiments, the luminescence-determined temperature accurately and/or substantially reflects the (average) internal temperature of the sample. Temperature determinations with greater or less than about 1 degree Celsius variation are also contemplated herein.

In certain illustrative embodiments, a raw, measured luminescence-determined temperature may be processed prior to being adopted or otherwise used as the temperature of the sample. Furthermore, determining the temperature of a sample as a function of at least the luminescent signal emitted by the reagent may also include averaging, factoring, calculating, and/or otherwise processing the luminescence-determined temperature with at least one other factor and/or determined temperature. For example, determining the temperature of a sample in a manner consistent with the luminescent signal emitted by the reagent may include determining the average between a raw (or processed) luminescence-determined solution temperature and a thermocouple-determined temperature or otherwise incorporating both the luminescence-determined solution temperature and thermocouple-determined temperature to arrive at a calculated sample temperature.

In at least one embodiment of the present invention, a second reagent that produces a second luminescent signal may be provided. In certain illustrative embodiments, the second luminescent signal may indicate the quantity or amount of sample, reagent, or mixture (e.g., the signal from a fluorescent or luminescent signal normalizing reagent). In some embodiments, the second luminescent signal may indicate an amount of nucleic acid present in the sample. For example, the second reagent may include a quantitative indicator of PCR product formation and/or other DNA binding reagent. One will appreciate however that the second reagent may also (or alternatively) include a positive or negative control reagent or another condition-sensitive reagent.

In certain embodiments, the sample may be provided as a PCR sample and/or mixture or a post-PCR sample and/or mixture. One will appreciate, however, that the sample may be any type of biochemical, industrial, commercial, scientific, or other experiment or reaction. Referring briefly to FIG. 1, CPU 706 may output to the user interface 704 a graph of the signal from the second reagent plotted against the temperature as determined using the temperature-sensitive reagent.

In at least one embodiment, a method of measuring the temperature of a sample may further include stimulating the temperature-sensitive reagent to induce the luminescent signal, measuring the luminescence emitted from the sample, determining the temperature of the sample as a function of at least the luminescent signal emitted by the reagent, measuring the temperature of the sample by at least one other method, and/or any other step or portion of any method described herein at a plurality of time points and/or temperatures. For example, the method may include a step(s) involving measuring the fluorescence emitted from an excited (or otherwise stimulated) sample at a plurality of time points during PCR cycling or melting during or after PCR. One will appreciate, however, that measuring the luminescence emitted from a non-stimulated sample is also contemplated herein.

In yet other embodiments, the luminescent signal from a temperature-sensitive reagent is used to adjust a melting curve generated from a biological or other substrate. For example, a melting curve of a PCR amplicon may be generated post-PCR, and the temperatures displayed for the melting curve may be adjusted based on the luminescent signal generated from the temperature-sensitive reagent during melting of the PCR amplicon.

Various embodiments of illustrative methods are available to correlate fluorescence emission with solution temperature. In one embodiment (termed single-dye/single-color), a single dye is excited at a specific wavelength and changes in emission intensity are monitored in a single spectral band, as discussed further in the following references, the entirety of each of which is herein incorporated by reference: (1) J. Sakakibara, K. Hishida, M. Maeda, Vortex structure and heat transfer in the stagnation region of an impinging plane jet (simultaneous measurements of velocity and temperature fields by digital particle image velocimetry and laser-induced fluorescence), Int. J. Heat Mass Transfer 40 (1997) 3163-3176; (2) F. Lemoine, M. Wolff, M. Lebouche, Simultaneous concentration and velocity measurements using combined laser-induced fluorescence and laser Doppler velocimetry: Application to turbulent transport, Exp. Fluids 20 (1996) 319-327; (3) F. Lemoine, Y. Antoine, M. Wolff, M. Lebouche, Simultaneous temperature and 2D velocity measurements in a turbulent heated jet using combined laser-induced fluorescence and LDA, Exp. Fluids 26 (1999) 315-323; and (4) P. Lavieille, F. Lemoine, G. Lavergne, F. Virepinte, M. Lebouché, Temperature measurements on droplets in monodisperse stream using laser-induced fluorescence, Exp. Fluids 29 (2000) 429-437.

Other embodiments may employ a ratio where fluorescence on two (single-dye/two-color) or even three (single-dye/three-color) spectral bands is measured, as discussed further in the following references, the entirety of each of which is herein incorporated by reference: (1) P. Lavieille, F. Lemoine, G. Lavergne, M. Lebouché, Evaporating and combusting droplet temperature measurements using two-color laser-induced fluorescence, Exp. Fluids 21 (2001) 45-55; (2) M. Bruchhausen, F. Guillard, F. Lemoine, Instantaneous measurement of two-dimensional temperature distributions by means of two-color planar laser induced fluorescence (PLIF), Exp. Fluids 38 (2005) 123-131; (3) P. Lavieille, A. Delconte, D. Blondel, M. Lebouché, F. Lemoine, Non-intrusive temperature measurements using three-color laser-induced fluorescence, Exp. Fluids 36 (2004) 706-716; and (4) M. Bruchhausen, A. Delconte, Temperature measurements in polydisperse sprays by means of laser-induced fluorescence (LIF) on three spectral bands, Atomization and Sprays 16 (2006) 599-614.

The some embodiments, measured fluorescence intensity from a spectral band that is sensitive to temperature is normalized by the intensity measured on a second spectral band that is insensitive to temperature, with the intent of improving temperature accuracy. Additional implementations excite a single dye (typically one that is sensitive to changes in pH) at two different excitation wavelengths (dual excitation single-dye/single-color). A ratio is then calculated using emission intensity measured on the same spectral band, as discussed further in J. Han, K. Burgess, Fluorescent Indicators for Intracellular pH, Chem Rev. 110 (2010) 2709-2728, the entirety of which is herein incorporated by reference.

It is noted that a method of measuring a temperature, condition, or physical or other property of a sample according to an embodiment of the present invention may include, incorporate, or otherwise comprise properties, reagents, steps, components, members, and/or elements described in other systems, methods, and/or mixtures disclosed herein.

V. Methods of Calibrating a Device

Certain embodiments of the present invention may also involve a method of calibrating a sample-heating, thermocycling, or other device or system. Such a method may include providing a calibration sample that includes at least one condition-sensitive reagent that emits a luminescent signal in response to a stimulus. The calibration sample may be provided as a suspension, solution, and/or other form or physical state of sample compatible with the methods herein disclosed and described.

Some embodiments may also involve stimulating the condition-sensitive reagent to induce emission of the condition-dependent or condition-sensitive luminescent signal therefrom. Appropriate qualitative and quantitative reagent stimulation may be required in certain embodiments. For example, for an illustrative fluorescent reagent such as sulforhodamine B, electromagnetic radiation may be a qualitatively appropriate form of stimulation, while an amount of, specific wavelength (such as 575 nm) or range of (such as 470-480 nm), and/or length of exposure to such electromagnetic radiation may be an appropriate quantitative factor or parameter for effective reagent stimulation.

Certain embodiments may also include measuring the amount of luminescence (or luminescent signal) emitted from the condition-sensitive reagent. Referring again to FIG. 1, such a measuring step may involve an optical system 710, optical element 711, or other luminescence measuring or detection member, element, or device configured to measure emission of luminescent signals.

In at least one embodiment, a method of calibrating a device may also include measuring and/or determining a luminescence-determined temperature as a function of (at least) the luminescence signal emitted by the condition-sensitive reagent.

Certain illustrative embodiments may also include measuring a device-determined temperature. In certain embodiments, the device-determined temperature for the sample is measured by inference from an external or indirect source. In certain illustrative embodiments, the temperature of a sample block or chamber 716 in which a sample 712 and/or sample vessel or container 714 is placed may be measured, optionally adjusted for known or suspected variation or discrepancy, and adopted as a device-determined temperature for the sample.

In certain embodiments, the method may also involve adjusting the device and/or the device-determined temperature to reflect (at least) the luminescence-determined temperature. Such a step may be termed a calibration step in certain illustrative embodiments. In at least one embodiment, adjusting the device and/or the device-determined temperature may involve adopting the raw or processed luminescence-determined temperature. One will appreciate, however, that adjusting the device and/or the device-determined temperature to reflect the luminescence-determined temperature may also (or alternatively) involve averaging and/or otherwise factoring one or more luminescence-determined temperatures and/or one or more temperatures otherwise measured or determined (e.g. internally; through direct contact with the sample). Other methods for measuring, determining, factoring, and/or calculating temperatures from a plurality of values and/or data points are known in the art and described in U.S. Patent Application Publication No. 2013-0157376, the entirety of which is herein incorporated by reference.

It is noted that calibrating and/or adjusting the device-determined temperature according to factors other than and/or in addition to the luminescence-determined temperature may still constitute adjusting the device-determined temperature to reflect or represent the luminescence-determined temperature and/or in a manner consistent with the luminescence-determined temperature. Therefore, all such (or similar) methods or steps of methods may involve adjusting the device-determined temperature in a manner consistent with the luminescence-determined temperature.

In certain illustrative embodiments, the adjusting step may include adjusting the output of temperature controlling device(s) 718, 720 to provide more heating and/or cooling. This adjusting step may include a single adjustment for one or more of the temperature controlling devices or may include multiple adjustments for one or more elements of such a device (such as a thermoelectric Peltier, illustratively). The adjusting step may involve manually performed steps and/or automated steps performed with the aid of a CPU 706, computer, or other hardware and/or software.

It is noted that a method of calibrating a sample-heating or other device according to an embodiment of the present invention may include, incorporate, or otherwise comprise reagents, steps, components, members, and/or elements described in other systems, methods, and/or mixtures disclosed herein.

VI. Methods of Fluorescence Feedback

Certain embodiments of the present invention may also involve a method of using the luminescent signal to adjust temperature of a sample-heating, thermocycling, or other device or system prior to or during PCR. Such a method may include providing a PCR sample that includes at least one condition-sensitive reagent that emits a luminescent signal in response to a stimulus. The feedback sample may be provided as a suspension, aqueous solution, or other form or physical state of sample compatible with the methods herein disclosed and described.

In one embodiment, rather than thermocycling between device-determined temperatures or thermocouple-determined temperatures, thermocycling occurs between luminescence-determined temperatures, and the luminescence signal is used to determine the start or end of programmed "hold" periods and/or trigger ramping to the next temperature in thermal cycling.

One illustrative example was constructed through modification of a LightCycler 24. The LightCycler 24 is a rapid-cycle real-time PCR instrument that uses air for temperature control. The LightCycler 24 was modified to allow for two methods of cycling control to be directly compared: (1) control by kinetically matched external thermocouple; and (2) control by fluorescence. Temperature control by fluorescence was achieved through a single-dye/single-color approach, although a single-dye/two-color approach and additional multi-dye and multichannel methods are contemplated within this disclosure. Temperature control by fluorescence provided equivalent or improved thermocycling control. While the LightCycler 24 was used as the initial instrument, it is expected that the methods will be applicable to any real-time thermocycler.

In the illustrative example, fluorescent-based temperatures (or the fluorescent value(s) from which they were calculated) were converted to voltage equivalents to replace standard thermocouple voltage input(s) for thermal cycling control. In other words, sample fluorescence (or fluorescence-determined temperature) was used instead of measured temperatures (i.e. thermocouple and/or instrument-determined temperatures) to control thermal cycling. Illustratively, sample temperature was determined as a function of fluorescent signal. Essentially, the voltage equivalents of measured amounts of fluorescent signal emitted from a sample were compared to and/or coordinated with a calibration standard for amounts of fluorescent signal emitted by that reagent at various temperatures. Thus, the calibration standard was used to provide a temperature point at which the reagent was known to emit a measured amount of fluorescent signal, such that fluorescent signal was correlated with sample temperature. One will appreciate that fluorescent-based temperatures could also be used directly or converted to voltage equivalents to replace standard instrument temperature-related voltage inputs for thermal cycling control.

Figure 2:
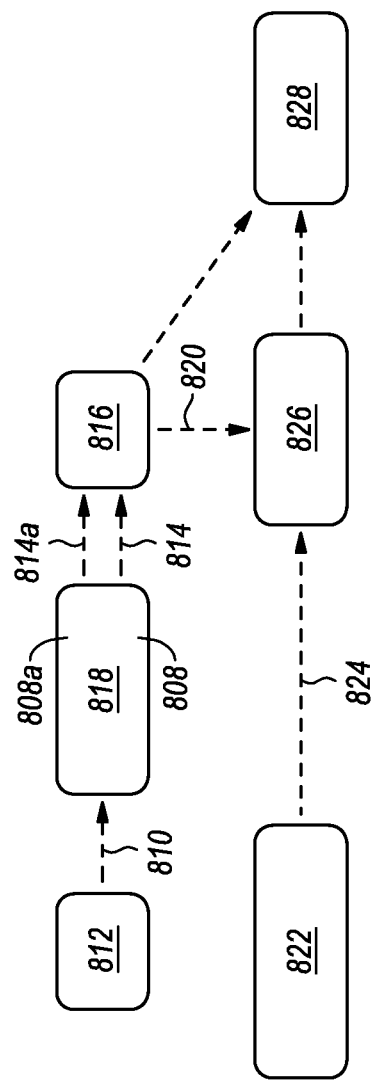
FIG. 2 illustrates a schematic diagram of fluorescence-based temperature control for a thermal cycling system.

A schematic diagram of an illustrative example of fluorescence-based temperature cycling control is shown in FIG. 2. In certain embodiments, the fluorescent dye 808, illustratively in a sample container (not shown) in block 818 is excited by light 810 from an illustrative light-emitting diode (LED) 812 or other suitable light source. The light 810 excites emission 814, 814a from the fluorescent dye included in samples 808 and 808a, respectively. The intensity of the emission 814, 814a from the fluorescent dye included in samples 808 and 808a, respectively, may be detected by an illustrative photomultiplier (tube) (PMT) 816 or other fluorescence detection apparatus. In some embodiments, excitation 810 and/or emission 814 pathways may be filtered through block 818.

Certain illustrative embodiments of this process involve an initial calibration to determine reference temperatures 826 for a reference sample 808 that may be used to calculate fluorescence-based temperatures 828 for a sample 808a during subsequent cycling. During initial calibration, reference fluorescence intensity values 820 and temperature measurement values 824 (via a thermocouple 822) from sample 808 may be recorded and used to calculate fluorescence-based or fluorescence-determined reference temperatures 826, which may be correlated with the fluorescence intensities 820 from which they were calculated and/or derived (e.g. to create a standard). These calculated reference temperatures or values 826 (or the standard which correlates fluorescence intensities with their respective temperatures) may then be used to control temperature of block 818, illustratively by triggering the next thermal cycling phase during PCR of sample 808a. For example, during PCR an illustrative fluorescent emission 814a (from sample 808a), which corresponds to a known reference temperature 826, may be detected by the PMT 816 and used to: (1) determine the (fluorescence-based) temperature 828 of the sample; (2) determine a cycle point in the temperature cycle; and/or (3) trigger or initiate a change to another phase in a thermal cycling profile.

One will appreciate, however, that thermocouple-determined temperatures or temperature readings may also be used during cycling. The modified LightCycler 24 may accept voltage inputs from both standard thermocouples and fluorescence-based equivalents. Thus, in certain embodiments, a standard thermocouple may be placed in an adjacent sample, well, or capillary for comparison and for use in determining reference temperature values.

Illustratively, a calibration curve may be acquired continuously by a slow ramping (for example, at a target rate 0.05° C./s-0.1° C./s) transition or a step and hold transition. In one embodiment, one point is recorded at the end of each holding period (1 s-10 s) at a set temperature increment (0.1° C.-1° C.). The illustrative instrument may be able to hold at a set temperature for up to 10 s, to determine reference values and for extension during cycling.

The illustrative instrument may also be able to cycle between three set temperatures (denaturation, annealing, and extension) for a number of cycles sufficient to complete the reaction. In some embodiments, PCR reactions of 35 cycles can be completed in about 3 minutes and 45 seconds, illustratively when using 2 trigger temperatures (denaturation and annealing/extension). The optical configuration may allow for the excitation and detection of at least two dyes (one for real-time monitoring, one for temperature control). The dye used for temperature control may be monitored at one, two, three or more wavelengths to provide ratios that improve the signal to noise ratio. In some illustrative embodiments, the excitation may be continuous or intermittent. For example, in one embodiment, the excitation light is intermittently flashed between an excitation wavelength that excites the real-time monitoring dye, and an excitation wavelength that excites the temperature control dye. It is understood that the frequency of excitation between the two wavelengths should be high enough so that temperature control can be achieved without substantial error. For example, if the rate of transition is 10° C./s, then flashing the wavelength that excites the temperature control dye at 100 Hz should allow a resolution of about 0.1° C.

To determine whether the methods described herein result in improved temperature control, thermal cycling controlled by the following methods may be compared:

Method A) An external thermocouple

Method B) Fluorescence—single-dye/single-color approach, where a single dye is excited at a specific wavelength and changes in emission intensity are monitored in a single spectral band.

Method C) Fluorescence—single-dye/two-color approach, where the measured fluorescence intensity from a spectral band that is sensitive to temperature is normalized by the intensity measured on a second spectral band that is insensitive to temperature.

It is noted that Methods B and C are illustrative only, and that other methods of controlling temperature using fluorescence are contemplated, including implementations that excite a single dye (typically one that is sensitive to changes in pH) at two different excitation wavelengths (dual excitation single-dye/single-color). A ratio may then be calculated using emission intensity measured on the same spectral band. Other approaches achieve normalization with two dyes (two-dye/two-color) configurations, wherein a temperature-sensitive dye is normalized using the signal from another dye with similar or opposing temperature sensitivity.

The Cq value may serve as a good indicator of temperature accuracy, particularly at annealing. If the annealing temperature is too low, primers may non-specifically hybridize. In such a case, the Cq value may be significantly lower, but the wrong product may have been amplified. Alternatively, if the annealing temperature is too high, primers may have difficulty in hybridizing to the DNA, lowering the efficiency, and pushing the Cq to later cycles. If temperature accuracy is enhanced, Method C may produce the lowest average Cq value when compared to Method A or B, with Method C producing the correct product.

Temperature accuracy may also be ascertained through the reproducibility of Cq values from real-time curves. The standard deviation of the Cq values may be calculated for cycling controlled through Methods A, B, and C. Factoring in potential pipetting uncertainties, the Cq values may have a standard deviation of no more than 0.5 cycles.

Samples amplified from Methods A, B, and C in Step 3 may be melted to determine product purity. Predicted melting curve may be used for comparison. These comparisons (of melting temperature, shape and number of peaks) may verify that lower Cq values are resultant from enhanced solution temperature accuracy during cycling and not as a result of non-specific amplification.

In certain embodiments, the fluorescence-based solution temperature from Method C may align more closely with recordings made by the physically inserted thermocouple when compared to Methods A or B. As a quantitative measure, the mean solution-thermocouple temperature difference (and standard deviation) may be compared during the three transition periods (denaturation to annealing, annealing to extension, and extension to denaturation) for cycles 1, 10, 20, and 30, illustratively. Values may be calculated for each method, and Method C may demonstrate the lowest mean value and standard deviation for all temperature transitions across all cycles.

VII. Use of Ratios for Added Control

Many dye and excitation/detection configurations exist for determining solution temperatures based upon changes in fluorescence. These approaches fall into distinct categories. Each may be used within the scope of the present invention, and illustrative examples of each are briefly discussed below.

Single-Dye/Single-Band Method

The single-dye/single-band method may employ the excitation of a temperature-sensitive dye at a set wavelength. Changes in the emission intensity, detected on a specific wavelength band across temperature, may be monitored. As temperature increases, fluorescence intensity of the dye may decrease, due to more significant collisional quenching occurring during the excited-state lifetime, which may reduce quantum yield. To obtain fluorescence-temperature correlations, a calibration curve may be generated at equilibration temperatures (T) and corresponding intensities (I). These data, along with a reference temperature ($T_{reference}$) and intensity ($I_{reference}$) measurement, allows for a calibration constant, C, to be determined. The value of C is equal to the slope of the linear line formed by plotting $$\left(\frac{1}{T} - \frac{1}{T{reference}}\right)$$

versus ln $$\left(\frac{I(T)}{I(Treference)}\right).$$

When the calibration constant is combined with reference measurements and real-time fluorescence readings, the average solution temperature may be calculated using the following equation:

$$\ln\left(\frac{I(T)}{I(Treference)}\right) = C\left(\frac{1}{T} - \frac{1}{Treference}\right) \qquad \text{[Equation 1]}$$

It is understood that the single-dye/single-band approach may be limited in accuracy because measurements are based on absolute intensity. In instances where variables such as excitation intensity, dye concentration, and sample volume cannot be kept sufficiently constant, their influence can substantially decrease the accuracy of the solution temperature measurement. Particularly in the case of laser-induced fluorescence, fluctuations in incident laser intensity can produce inaccurate temperature measurements. This has led to alternative approaches that employ ratios. The use of ratios allows for self-normalization and may largely account for variations in excitation intensity and changes in sample volume and dye concentration that may occur.

Single-Dye/Two-Band Method

The use of a ratio allows for experimental variation to be mitigated, thus increasing the accuracy of fluorescence-based solution temperature measurements. The single-dye/two-band method may employ two distinct spectral bands of a single fluorescent dye: one that may be sensitive to temperature and another that may be generally temperature insensitive. Self-normalization is achieved by taking a ratio of the intensities recorded on the two spectral bands. In this case, two calibration constants are calculated: one for each spectral band. The individual constants may be subtracted to determine the final calibration constant, $C_F$. As with the single-band approach, a reference temperature and intensity measurement may be employed, as shown in Equation 2.

$$\ln\left(\frac{R(T)}{R(T_{reference})}\right) = C_F\left(\frac{1}{T} - \frac{1}{T_{reference}}\right) \quad [\text{Equation 2}]$$

Wherein
R(T) is the ratio at the measured temperature
$R(T_{reference})$ is the ratio at the reference temperature
$T_{reference}$ is the reference temperature and
$C_F$ is the final calibration constant.

Single-Dye/Three-Band Method

For improved temperature accuracy at longer optical pathlengths and/or high dye concentrations (where fluorescence re-absorption may be significant) a single-dye/three-color method has been developed, and may be employed, wherein multiple ratio calculations are made using data from three spectral bands.

Ratiometric pH Indicators

Fluorescent pH-sensitive dyes may be used as an extension of the single-dye/two-band or other method. Through at least either single-excitation/dual-emission or dual-excitation/single-emission configurations, these dyes may be similarly self-normalizing.

PCR mixtures may include a buffer to aid in sensitivity (through optimizing polymerase activity) and specificity (by enhancing primer/DNA hybridization). An illustrative commonly used buffer is Tris, as it is well matched to the optimal pH range for Taq polymerase (7-8 pH units at 80° C.). The pH of Tris buffer solutions are also temperature dependent, thus allowing for the optimal pH range for PCR to be maintained while changes in temperature are correlated with observed changes in pH.

Fluorescent pH-sensitive dyes achieve different molecular forms (due to progressive dissociation) as the solution pH changes across temperature. Different forms of the molecule may exhibit different emission spectra, most notably alterations in intensity at specific wavelengths. The ratio of the intensities at prominent features (such as spectral peaks at set wavelengths) allows for self-normalization of the dye. Changes in temperature can then be monitored by fluorescence when a fluorescent pH-sensitive dye is added to the reaction mixture.

VI. Examples

In addition to the illustrative embodiments discussed above, the following illustrative examples and results may be useful in enabling a person of ordinary skill in the art to make and/or use the invention. Importantly, the following examples and results are illustrative only and are not intended to limit the scope of the present invention. Furthermore, different results may be observed when practicing certain embodiments of the present invention. As such, the following results are not intended to limit the scope of the present invention.

Real-Time PCR Instruments

Several real-time PCR instruments were used, based on availability and sample format. Four of these were carousel-based instruments: the LightCycler® 24 (Idaho Technology), LightCycler® 1.5 (Roche Applied Science), LightCycler® 2.0 (Roche Applied Science), and the Rotor-Gene® Q (Qiagen). In addition, five plate-based instruments were used for this study: the LightCycler® 480 (Roche Applied Science), Eco™ (Illumina), iCycler (Bio-Rad), CFX96™ (Bio-Rad), and the StepOnePlus™ (Life Technologies).

Different instruments vary widely in their ability to collect fluorescence during temperature cycling. Instruments naturally split into one of four classes. Class I instruments are most flexible and can continuously acquire fluorescence during heating, cooling and temperature holds. Class II-IV instruments are more limited. During temperature cycling, Class II and III instruments only allow fluorescence collection once each temperature hold, while Class IV instruments can only acquire once each cycle. During temperature transitions, Class II instruments can collect heating or cooling curves, while Class III and IV are limited to only melting curves.

Four Class I instruments, three Class II instruments, and one each of Class III and Class IV were studied. All instruments used LED excitation except the iCycler (tungsten halogen lamp) and the LightCycler® 480 (xenon lamp). Typical excitation ranges were 470-480 nm, with the exception of the Bio-Rad instruments that were excited around 575 nm for more efficient excitation of sulforhodamine B. Detection formats included CCD cameras (iCycler, LightCycler® 480 and the Eco™), PMTs (Rotor-Gene® Q) and photodiodes (all others). Detection ranges were typically within 600-650 nm. However, the only melting channel on the Eco™ (505-545 nm) was incompatible with sulforhodamine B, so fluorescein was used as the temperature sensitive dye. Five or 10 µL samples were used on most instruments, although a large volume range (5-70 µL) was studied on the LightCycler® 480. An oil overlay of 2 µL was used with LightCycler® capillaries, and 0-20 µL/well on plate based instruments. PCR cycle times were much faster on the carousel-based LightCyclers (18-27 s/cycle) than on other instruments (66-120 s/cycle). The most relevant characteristics and experimental conditions for the real-time instruments are listed in Table 1 (below).

TABLE 1

| Instrument | Vendor | Excitation (nm) Source | Emission (nm) Detector | Solution Volume (µL) | Oil Overlay Volume (µL) | Calibration Curve Rate (° C./s) | Calibration Data Density (points/° C.) | During Cycling | During Ramping | Instrument Class |
|---|---|---|---|---|---|---|---|---|---|---|
| LightCycler 24 | Idaho Technology | 470 LED | 650-690 Photodiode | 10 | 2 | 0.1 | 122 | Continuous | | I |

TABLE 1-continued

| Instrument | Vendor | Excitation (nm) Source | Emission (nm) Detector | Solution Volume (µL) | Oil Overlay Volume (µL) | Calibration Curve Rate (° C./s) | Calibration Data Density (points/° C.) | During Cycling | During Ramping | Instrument Class |
|---|---|---|---|---|---|---|---|---|---|---|
| LightCycler 1.5 | Roche | 470 LED | 645 Photodiode | 10 | 2 | 0.1 | 50 | Continuous | | I |
| LightCycler 2.0 | Roche | 470 LED | 640 Photodiode | 10 | 2 | 0.1 | 44 | Continuous | | I |
| LightCycler 480 | Roche | 483 Xenon | 640 CCD Camera | 5-70 | 0-20 | 0.05 | 11 | Continuous[a] | | I |
| Rotor-Gene Q | Qiagen | 470 LED | 605-615 PMT | 10 | 15 | 0.031 | 2.0 | Once each hold | Heating or Cooling[b] | II |
| iCycler | Bio-Rad | 560-590 Tungsten Halogen | 605-635 CCD Camera | 10 | 15 | 0.025 | 1.8 | Once each hold | Heating or Cooling[b] | II |
| CFX96 | Bio-Rad | 575 LED | 610-650 Photodiode | 10 | 15 | 0.018 | 2.5 | Once each hold | Heating or Cooling[b] | II |
| StepOne-Plus | Applied Biosystems | 470 LED | 580 Photodiode | 10 | 15 | 0.022 | 2.5 | Once each hold | Heating[c] | III |
| Eco | illumina | 452-486 LED | 505-545 CCD Camera | 5 | 5 | 0.091 | 10 | Once each cycle | Heating[b] | IV |

[a]The fastest possible continuous acquisition rate is 0.57° C./s (programmed as 1 acquisition/° C. for a single color).
[b]Fluorescence is acquired once each temperature increment or step.
[c]Fluorescence acquisition can be either continuous or "step and hold".

Reagents

Fluorescence was measured in an illustrative "mock" PCR solution without polymerase and containing (Sigma-Aldrich), 50 mM Tris (pH 8.3), 2 mM $MgCl_2$, 0.2 mM each deoxynucleotide triphosphate (Roche), 500 µg/ml bovine serum albumin (Sigma), and 0.08% (v/v) glycerol. For the instruments other than the Eco™, 0.6 mM sulforhodamine B was used. For the Eco™ instrument, 4 µM fluorescein (Matheson, Coleman and Bell) was used in place of sulforhodamine B for optical compatibility of the dedicated melting channel. One will appreciate however, that control and/or "mock" PCR solutions, as well as PCR mixtures and/or other sample mixtures, according to the present invention may vary in certain reagent composition and concentration as disclosed herein and as otherwise known in the art.

Polymerase Chain Reaction

A 74 bp product of the 3'-untranslated region of the F2 gene bracketing rs1799963 was used in certain examples, illustratively, to test for sulforhodamine B inhibition of PCR. The reaction included the above mock PCR solution with the addition of 0.4 U/10 µl of KlenTaq polymerase (AB Peptides), 50 ng/10 µl of human genomic DNA, 0.5 µM of primers GGTTCCCAATAAAAGTGACTCTAG (Seq. ID No. 1) and CTGAGCCCAGAGAGCTGC (Seq. ID No. 2) and 3 mM $MgCl_2$. PCR was performed in glass capillaries in 10 µL volumes in a LightScanner®-32 (LS-32) thermal cycler (BioFire Diagnostics). An initial denaturation at 95° C. for 30 s was followed by 35 cycles of 95° C. for 0 s, 60° C. for 0 s, and 74° C. for 2 s.

In other examples, three forensic single-nucleotide polymorphisms (SNPs)—rs876724, rs917118, and rs763869—were amplified using the following primers: rs876724 CCACTGCACTGAAGTATAAGT (Seq. ID No. 3) and TTAGCAGAGTGTGACAAAAAA (Seq. ID No. 4), rs917118 AAGATGGAGTCAACATTTTACAAG (Seq. ID No. 5) and GATGACTGAGGTCAACGAG (Seq. ID No. 6) and rs763869 AGGATGTTTGTTTATATTATTTCTAACTCA (Seq. ID No. 7) and CTACTCCCTCATAATGTAATGC (Seq. ID No. 8). Each 10 µl reaction contained 50 mM Tris-HCl pH 8.3, 2.0 mM $Mg^{2+}$, 200 µM each dNTP, 1× LCGreen Plus (BioFire Diagnostics), 0.4 U KlenTaq1 (Ab Peptides) with 64 ng anti-Taq antibody (eEnzyme), 0.5 µg BSA, 0.5 µM primers and 50 ng genomic DNA. After an initial denaturation at 95° C. for 1 min, amplification conditions on the modified LightCycler were 85° C. for 10 s and 60° C. for 10 s for 35 cycles. To demonstrate the utility of fluorescence-based temperature control for use with more rapid protocols, the rs917118 target was amplified using "0"s hold times. The use of "0"s hold times was aided by increasing the concentration of primers by 5-fold (final concentration 2.5 µM). After an initial denaturation at 95° C. for 1 min, 35 cycles of 83° C. for "0"s and 61° C. for "0"s were performed. In all illustrative examples, thermal cycling was controlled by fluorescence-based temperature measurements.

Fluorescent Dye Temperature-Sensitivity

The temperature-sensitivity of 22 fluorescent dyes was examined on a custom multicolor fluorimeter with xenon excitation, spectral dispersion (405-590 nm) on a grating and focused onto a fiber optic (delta RAM, Photon Technology International). The fiber optic illuminated the end of a glass capillary (LightCycler, Roche Applied Science) placed within a heating unit (HR-1, BioFire Diagnostics). Fluorescent emission was collected by another fiber optic at a right angle to the capillary, delivering light onto a CCD spectrometer (DV420-OE, Andor Technology) collecting, 1024 bins between 400-850 nm. A J-type micro-thermocouple (5SRTC, Omega) was inserted into the sample capillary for physical temperature measurements.

Fluorescent dyes were tested in the "mock" (no polymerase) PCR solution described above. Final concentrations for each dye are listed in Table 2, along with excitation wavelengths. Twenty-five µL sample volumes were heated from 45° C. to 95° C. (in discrete 10° C. increments, with 100 points averaged per step). The ramp rate between steps during heating was approximately 0.4° C./s. The entire emission spectrum was then recorded and the fold-change in fluorescence (45-95° C.) calculated.

TABLE 2

| Dye | Source | Excitation Wavelength (nm)[3] | Concentration (μM) | Average Emission Peak Wavelength (nm)[5] | Fold-Change in Fluorescence (45-95° C.)[6] |
|---|---|---|---|---|---|
| 2',7'-Dichlorofluorescein | Sigma-Aldrich | 455/470/490 | 80 | 531 | 1.56 |
| 5(6) Carboxyfluorescein | Sigma-Aldrich | *470*/490 | 4 | 520 | *1.38* |
| 5(6) Carboxynapthofluorescein | Marker Gene Technologies, Inc. | *455*/470/490 | 4000 | 542 | *1.17* |
| Coumarin 6 | Sigma-Aldrich | *455*/470/490 | 800 | 521 | *2* |
| Eosin B | Sigma-Aldrich | *530* | 40 | 575 | *12.48* |
| Ethyl Eosin | Sigma-Aldrich | 455/470 490/530 | 800 80 | 557 | 2 |
| Fluorescein | Sigma-Aldrich | 455/*470*/490 | 800 | 516 | *1.26* |
| Fluorescein Sodium Salt | Matheson, Coleman, and Bell | 455/*470*/490 | 40 | 522 | *1.5* |
| HPTS | Invitrogen | 405/*455*/470/ 490 | 80 | 517 | *1.85* |
| Merocyanine 540 | Sigma-Aldrich | *470*/490/530 | 40 | 581 | *7* |
| Oregon Green 488 | Invitrogen | 455/470/490 | 40 | 522 | 1.15 |
| Resorufin | Sigma-Aldrich | *455* 470/490/530 | 800 80 | 591 | *1.25* |
| Rhodamine 101 | Sigma-Aldrich | 455/470/490 *530* | 4 40 | 599 | *1.21* |
| Rhodamine 110 | Invitrogen | 455/*470*/490 | 40 | 525 | *1.32* |
| Rhodamine 6G | Sigma-Aldrich | 470/490/*530* | 40 | 560 | *1.26* |
| Rhodamine B | Sigma-Aldrich | 470/490/*530* | 4 | 575 | *3.26* |
| Rose Bengal | Sigma-Aldrich | 490/*530* | 20 | 574 | *2.2* |
| Snarf-1 | Invitrogen | *455*/470/*490*/ 530 | 160 | 644 | *1.28* |
| Sulforhodamine 101 | Sigma-Aldrich | 470/490/*530* | 40 | 607 | *1.53* |
| Sulforhodamine B (monosodium salt)[1] | Sigma-Aldrich | *470* | 4,000 | 582 | *2.85* |

[1]Dye content is 75%.
[2]Dye content is 95%.
[3]Fluorescent trends as temperature is increased at a specific wavelength are denoted in bold (fluorescence increases), italicized (fluorescence decreases) or regular text (variable). The wavelength where the greatest changes in fluorescence were present is underlined.
[4]Listed concentrations do not account for percentage dye content. Where dye content is specified, these concentrations will be less.
[5]Emission peak wavelengths were averaged for all tested excitation wavelength/concentration combinations for each dye.
[6]The maximum fold-change in fluorescence from 45 to 95° C. (at the underlined excitation wavelength). Increased (bold) or decreased (italicized) fluorescence between the measurements at 45° C. and 95° C. is indicated.

The spectral profiles of the 22 dyes were recorded at multiple excitation wavelengths and temperatures (data not shown). For each dye, the fold change in fluorescence during heating from 45-95° C. is shown in Table 2, along with general trends in fluorescence (i.e. increased (bold) or decreased (italicized) intensity levels) that occurred during heating. The average fold-change in fluorescence for all dyes was 0.74 (±0.45). Eosin B, excited at 530 nm, exhibited the greatest fold-change in fluorescence (fluorescence decreased by a factor of 12.48), although differences in fluorescence levels at 85° C. and 95° C. were limited for that dye. An illustrative example for sulforhodamine B (monosodium salt), excited at 530 nm, is shown in FIG. 3.

Figure 3:
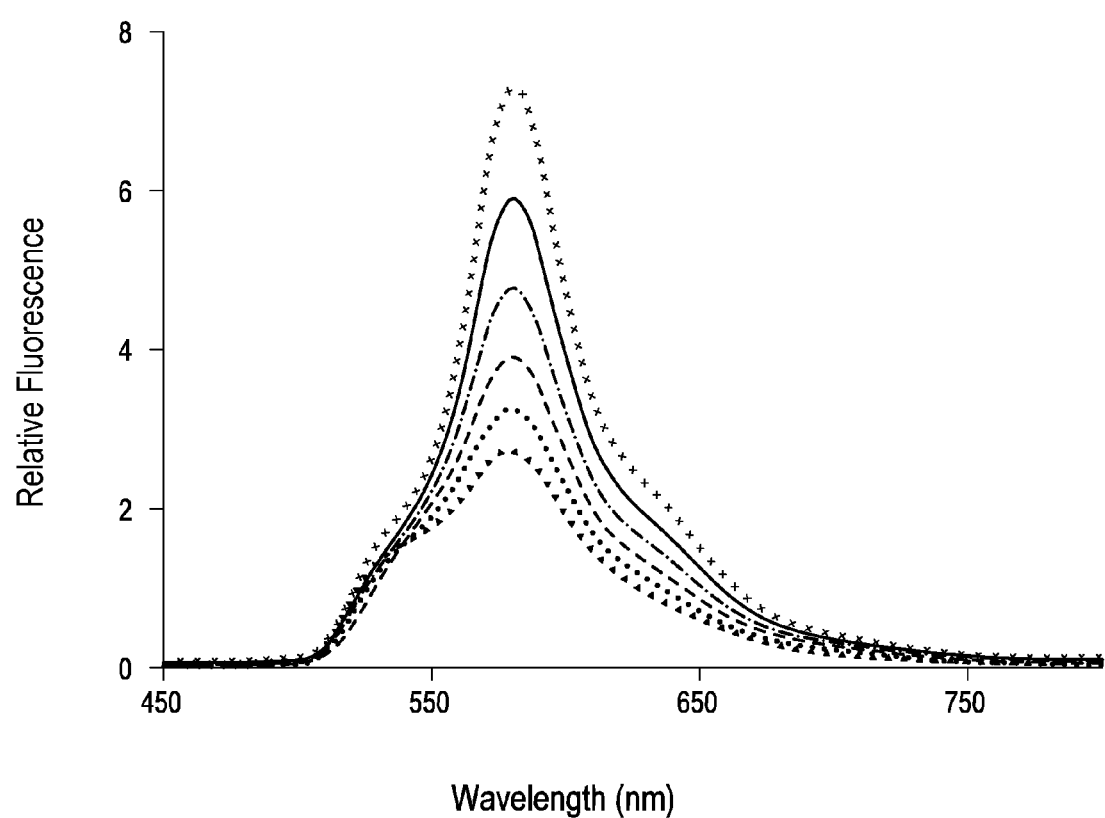
FIG. 3 illustrates a temperature-sensitivity profile for sulforhodamine B (monosodium salt) excited at 530 nm held at 45° C. (x-line), 55° C. (solid line), 65° C. (dash-dotted line), 75° C. (dashed line), 85° C. (dotted line), and 95° C. (triangle line).

FIG. 3 illustrates a temperature-sensitivity profile for (2,400 μM) sulforhodamine B (monosodium salt) in 25 μL sample volumes held at temperatures ranging from 45° C. (x-line) to 95° C. (triangle line) in 10° C. intervals. Specifically, sample(s) were held at 45° C. (x-line), 55° C. (solid line), 65° C. (dash-dotted line), 75° C. (dashed line), 85° C. (dotted line), and 95° C. (triangle line). Regions of high temperature-sensitivity (near 580 nm) are clearly discernible from regions of low temperature-sensitivity (near 525 nm).

Dyes exhibiting at least a 2-fold change in fluorescence were selected for more in-depth examination. Dyes that exhibited variable trends in fluorescence with increasing temperature or minimal differences (<5%) in fluorescence intensity at high temperatures (85° C. to 95° C.), were excluded from further consideration, although it is understood that such dyes may be useful in certain embodiments. Ethyl eosin, merocyanine 540, rhodamine B, snarf-1, sulforhodamine B (acid form), and sulforhodamine B (monosodium salt) were studied further.

Figure 4:
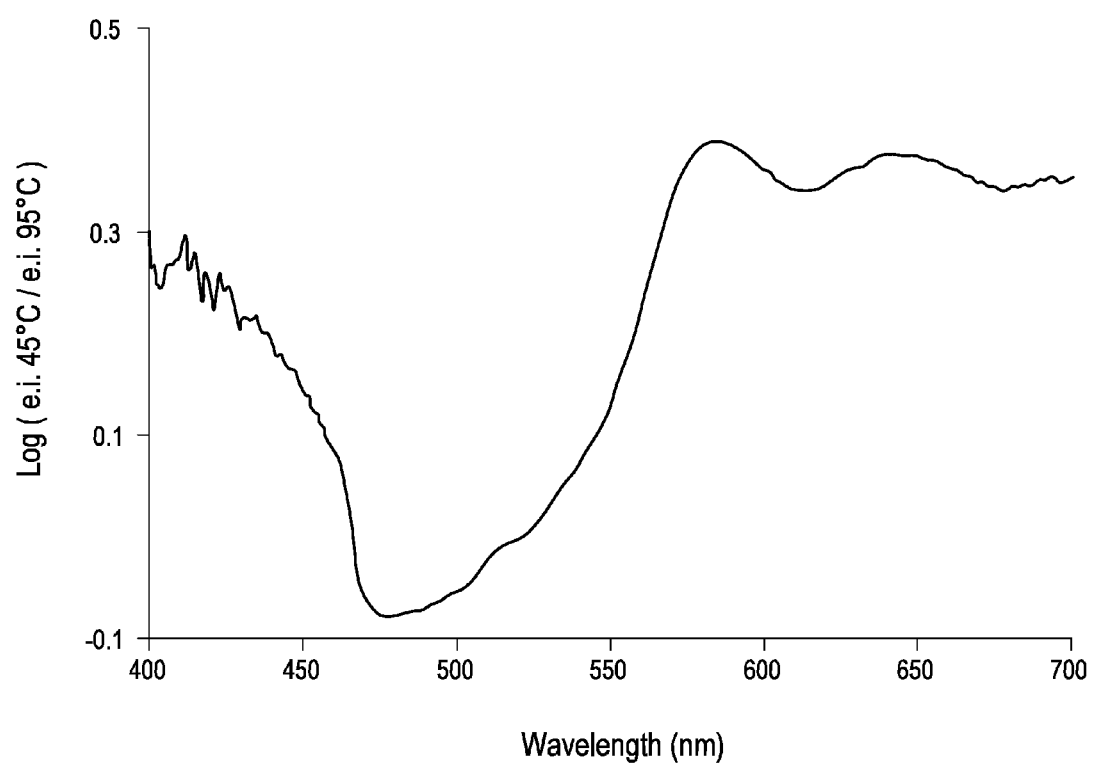
FIG. 4 illustrates temperature sensitivity and insensitivity of sulforhodamine B (monosodium salt) excited at 490 nm, with spectral data displayed as a log of the ratio of (emission intensity (e.i.) at 45° C./emission intensity (e.i.) at 95° C.) across wavelength.

To determine temperature sensitive and temperature insensitive regions of the emission spectrum, spectral data were displayed as a ratio (emission intensity at 45° C./emission intensity at 95° C.) on a log scale across wavelength (see e.g. FIG. 4). For instance, FIG. 4 illustrates temperature sensitivity of sulforhodamine B (monosodium salt) between 45° C. and 95° C., excited at 490 nm, with spectral data displayed as a ratio (emission intensity (e.i.) at 45° C./emission intensity (e.i.) at 95° C.) on a log scale across wavelength ranging from 400 nm to 700 nm, illustratively. It is understood that regions of low temperature-sensitivity have a ratio close to zero while regions of high temperature sensitivity have values furthest away from zero. Bands for each dye having the greatest temperature-sensitivity and insensitivity, respectively, were identified and are listed in Table 3.

Fluorescence-Based and Thermocouple Temperature Comparisons During Melting

The six dyes that exhibited the greatest sensitivity to temperature were further examined (see Table 4). Dye concentrations and excitation wavelengths are detailed in Table 4. Calibration constants for each dye were calculated from temperature and fluorescence data acquired from 45° C. to 95° C. in 10° C. increments. Using a second sample with a 30 μL final volume (25 μL sample with 5 μL oil overlay), an initial holding period at 50° C. was used to determine reference temperature and intensity values. The sample was then heated to 95° C. at an approximate rate of

TABLE 3

| Dye | Concentration (μM) | Excitation Wavelength (nm) | Degradation (Fold-change)[1] | Temperature-Sensitive Band (nm) | Temperature-Insensitive Band (nm) |
|---|---|---|---|---|---|
| Ethyl Eosin | 800 | 455 | 0.76 | 535-600 | 490-515 |
| Ethyl Eosin | 800 | 470 | 0.83 | 535-590 | 490-515 |
| Merocyanine 540 | 40 | 470 | 0.41 | 580-650 | 500-525 |
| Merocyanine 540 | 40 | 490 | 0.54 | 575-625 | 525-550 |
| Merocyanine 540 | 40 | 530 | 0.53 | 575-700 | 530-550 |
| Rhodamine B | 4 | 470 | 0.99 | 570-610 | 525-550 |
| Rhodamine B | 4 | 490 | 0.98 | 570-610 | 525-550 |
| Rhodamine B | 4 | 530 | 0.98 | 560-590 | 514-540 |
| Snarf-1 | 160 | 455 | 0.96 | 630-680 | 500-525 or 580-600 |
| Snarf-1 | 160 | 470 | 0.97 | 630-680 | 500-525 or 560-600 |
| Snarf-1 | 160 | 490 | 0.89 | 625-675 | 525-575 |
| Sulforhodamine B, Acid form | 8 | 455 | 0.85 | 575-610 | 500-550 |
| Sulforhodamine B, Acid form | 8 | 470 | 0.93 | 575-620 | 500-550 |
| Sulforhodamine B, Acid form | 8 | 490 | 0.95 | 575-620 | 525-550 |
| Sulforhodamine B, Acid form | 8 | 530 | 0.86 | 575-620 | 525-550 |
| Sulforhodamine B (monosodium salt) | 4,000 | 470 | 1.0 | 575-610 | 516-545 |
| Sulforhodamine B (monosodium salt) | 2,400 | 490 | 0.98 | 575-610 | 516-545 |
| Sulforhodamine B (monosodium salt) | 2,400 | 530 | 0.97 | 575-610 | 516-545 |

[1]Samples were heated from 45 to 95° C. and then cooled to 45° C. Values were calculated at the emission peak wavelength. The fluorescence at the second measurement was divided by the fluorescence of the first measurement. Thus, a value of 1 indicates that no degradation occurred.

Fluorescent Dye Degradation

The custom multicolor instrument described above to assess temperature sensitivity was also used to assess the amount of dye degradation after a single heating and cooling cycle. After the sample temperature reached 95° C., samples were cooled to 45° C. (using passive cooling), and an additional spectral measurement was made.

For most dyes, dye degradation caused a decrease in fluorescence even after a single heating and cooling cycle (see Table 3). Illustratively, Sulforhodamine B, excited at 470 nm, had a value of 1, indicating that no degradation occurred. Values for ethyl eosin (excited at 455 nm) and merocyanine 540 (excited at 470 nm) were 0.76 and 0.41, respectively, showing more degradation in these two dyes.

0.05° C./s. Fluorescence-based solution temperatures were calculated for both single-dye/single-color and single-dye/two-color configurations using sulforhodamine B (acid form). Solution temperatures using the single-dye/two-color method were calculated as described in P. Lavieille, F. Lemoine, G. Lavergne, M. Lebouché, Evaporating and combusting droplet temperature measurements using two-color laser-induced fluorescence, Exp. Fluids 21 (2001) 45-55, the entirety of which is herein incorporated by reference. Fluorescence-based temperatures were compared to thermocouple readings. Because sulforhodamine B (monosodium salt) exhibited the strongest temperature sensitivity as well as the most repeatable fluorescence after heating and cooling, it was used for thermal cycling control, as well as testing of all of the instruments except the Eco™.

TABLE 4

| Dye | Concentration (μM) | Excitation (nm) | Utilized Bands | Emission (nm) | Calibration Constant | Temperature Difference (Fluorescence-Thermocouple) Max (° C.)[1] | Temperature Difference (Fluorescence-Thermocouple) Mean ± SD (° C.)[2] |
|---|---|---|---|---|---|---|---|
| Ethyl Eosin | 800 | 470 | 1 | 550-625 | −1445 | 9.8 | 2.2 ± 4.9 |
| Merocyanine 540 | 40 | 490 | 1 | 575-625 | 4267 | 21.3 | 7.1 ± 3.7 |
| Rhodamine B | 4 | 490 | 1 | 574-610 | 2551 | 1.1 | −0.1 ± 0.5 |
| Snarf-1 | 160 | 490 | 1 | 640-675 | 1712 | 5.4 | 4.1 ± 1.5 |
| Sulforhodamine B, Acid Form | 80 | 490 | 1 | 574-610 | 2570 | 0.6 | −0.4 ± 0.1 |
| Sulforhodamine B, Acid Form | 80 | 490 | 2 | 525-550 and 574-610 | 1856 | 0.3 | 0.1 ± 0.1 |
| Sulforhodamine B (monosodium salt) | 4,000 | 490 | 1 | 574-610 | 2040 | 2.4 | 1.2 ± 0.9 |

[1]The absolute temperature difference between fluorescence-based and thermocouple temperatures.
[2]Thermocouple temperatures are subtracted from fluorescence-based temperatures.

Correlating Temperature to Passive Dye Fluorescence

To correlate fluorescence intensity to temperature, calibration curves were generated on each instrument by slowly heating. To limit dye degradation, a 50-95° C. range was completed in less than 45 minutes. Rates of 0.018-0.1° C./s were used. The fastest rate (0.1° C./s) was used on the LightCycler® carousel instruments because of rapid thermal equilibrium, single sample acquisition, and high data densities (44-122 points/° C.). Of similar rate (0.05 and 0.091° C./s), but with decreased data density (11 and 10 points/° C.), were the LightCycler® 480 and Eco™, respectively. All other instruments fell into a third range of lower rates (0.018-0.031° C./s) required by slower data acquisition for 1.8-2.5 points/° C.

Three possible sources of bias; instrument drift, thermal degradation, and fluorescence quenching were examined on the LightCycler® 1.5, 2.0, and 480. To examine instrument drift and thermal degradation of the dye, temperatures were held at 50° C., 80° C. and 94° C. for one hour. Once each minute, the sample was illuminated and fluorescence acquired. To test for fluorescence quenching, the temperature was held at 80° C. and data collected for 1 hour during either continuous or intermittent (once per minute) illumination.

Calculation of Solution Temperatures from Fluorescence

Fluorescence emission has been modeled previously, correlating fluorescence intensity to either concentration or temperature, depending on which variable is kept constant. Dyes that decrease in fluorescence with increasing temperature result from quenching of the excited state and lowered quantum yield. Temperature can be related to fluorescence through a calibration constant:

$$C = \ln\left(\frac{1}{I_{ref}}\right) \Big/ \left(\frac{1}{T} - \frac{1}{T_{ref}}\right)$$

Fluorescence intensities I are measured at temperatures T (in degrees Kelvin) and related to a reference fluorescence intensity ($I_{ref}$) of the temperature-sensitive reagent at a reference temperature ($T_{ref}$). Experimentally, plots of ln $$\left(\frac{1}{I_{ref}}\right)$$

against $$\left(\frac{1}{T} - \frac{1}{T_{ref}}\right)$$

form a straight line with slope C and intercept 0. The calibration constant is dependent on the physical characteristics of the fluorescent molecule in a particular solvent. Reference temperatures were 50° C. for calibration constant determination and melt curve analysis and 55° C. for PCR cycling experiments on each instrument. Solution temperatures were determined from fluorescence using C, the reference temperature, and the reference fluorescence:

$$T = \frac{1}{\frac{\ln(I/I_{ref})}{C} + (1/T_{ref})}$$

Fluorescence was acquired according to the capability of each instrument: continuously, at temperature holds, or during transitions (heating and/or cooling). Instrument-specific calibration constants were used to convert fluorescence to solution temperatures for comparison to temperatures displayed by the instruments. The calibration constant may be used to provide a quantitative method of judging the overall temperature sensitivity of the reagent/dye and/or optics. A higher value of the calibration constant may correlate to greater temperature sensitivity and system precision. Unless otherwise specified, the fastest transition rates were used on each instrument during cycling. One will appreciate, however, that the equations, variables, and calculations discussed herein are illustrative only, and that a variety of reference temperatures, reference fluorescence intensities, and/or other variables, equations, and/or calculations may be used in the calculation and/or determination of temperature(s) from fluorescence emissions.

Micro-Thermocouple Measurements

When physical instrument configuration allowed, sample temperatures *were* also monitored with a J-type micro-thermocouple (5SRTC, Omega) with conditioning, digitization and display (USB-TC01, National Instruments) to correlate with solution and instrument temperatures. Other thermocouples are known in the art and contemplated herein.

Melting Curve Analysis

Melting curves were obtained on the LC480 using both instrument and solution temperatures. Bacteriophage lambda DNA (New England BioLabs) at 2 µg/ml and 1× LCGreen® Plus (BioFire Diagnostics) were included in the mock PCR solution. Both DNA melting (LCGreen Plus, excitation at 450 nm, emission at 500 nm) and temperature (sulforhodamine B, excitation at 558 nm, emission at 610 nm) were monitored simultaneously by fluorescence during heating of the sample from 60-95° C. Data were collected at either 2 acquisitions/° C. (0.14° C./s), or at 40 acquisitions/° C. (0.01° C./s). Sulforhodamine B fluorescence was converted to temperature and negative derivative melting plots were displayed using either solution or instrument temperatures.

Fluorescence-Based Temperature Cycling Control

Figure 5A:
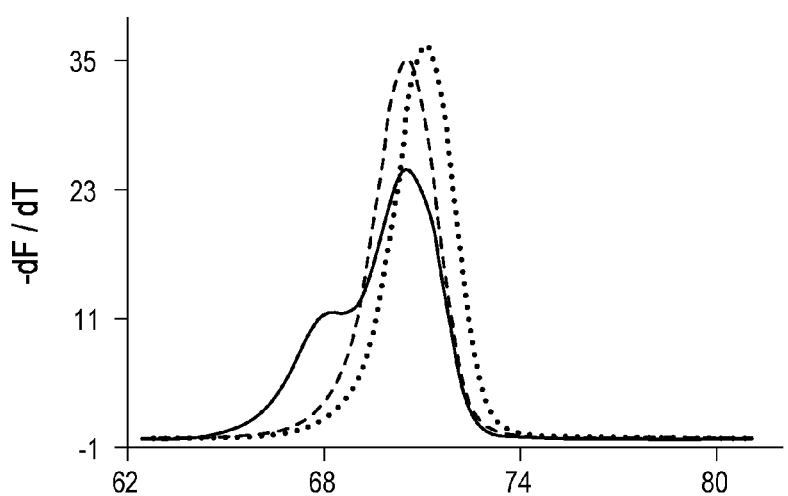
FIG. 5A-5C show derivative-melting plots for 3 forensic single-nucleotide polymorphisms, rs763869 (FIG. 5A), rs876724 (FIG. 5B), and rs917118 (FIG. 5C), amplified using fluorescence-based cycling control.
Figure 5B:
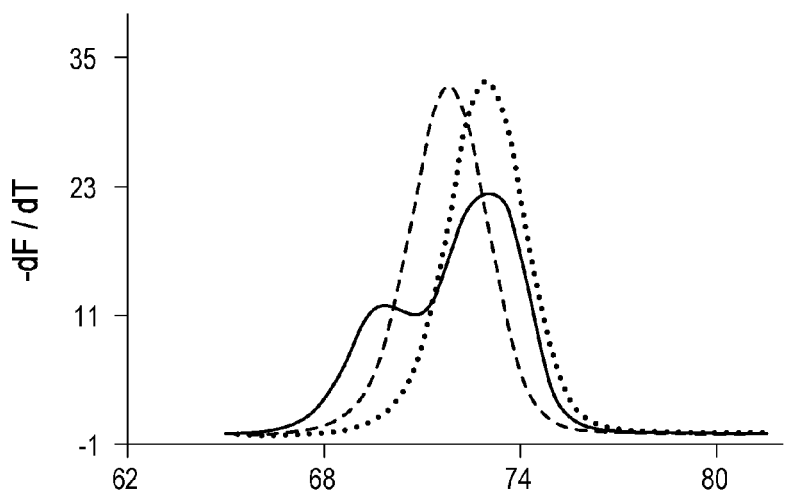
Figure 5C:
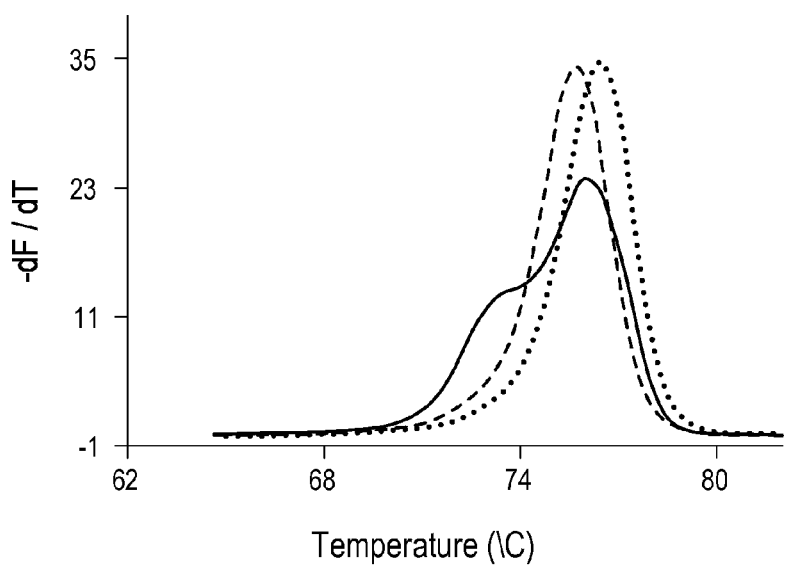

Temperature or thermal cycling using fluorescence-determined temperatures to control cycling was demonstrated using the modified LightCycler 24 described above. As illustrated in FIGS. 5A-5C), the three forensic single-nucleotide polymorphisms (SNPs) rs876724 (FIG. 5A), rs917118 (FIG. 5B), and rs763869 (FIG. 5C) were genotyped after amplification utilizing fluorescence-based thermal cycling control with 10 s holding times (quantification cycle ($C_q$) value of 24). After an initial denaturation at 95° C. for 1 min, amplification conditions were 85° C. for 10 s and 60° C. for 10 s for 35 cycles, resulting in a protocol time of 15 minutes and 46 seconds. Melting analysis using the quantum method of background removal (see U.S. Patent Application No. 61/872,173, the entirety of which is herein incorporated by reference) identified all genotypes, with all 3 genotypes (wild-type (dotted line), variant (dashed line) and heterozygotes (solid line)) clearly distinguishable (see FIGS. 5A-5C) for all targets.

Figure 6A:
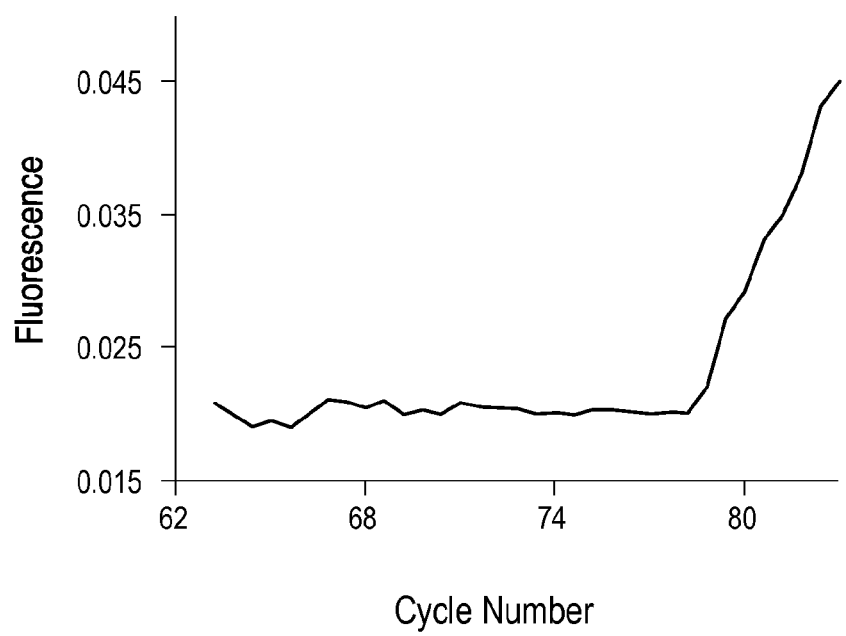
FIGS. 6A-6B illustrate amplification using "0"s hold times with fluorescence-based temperature control.
Figure 6B:
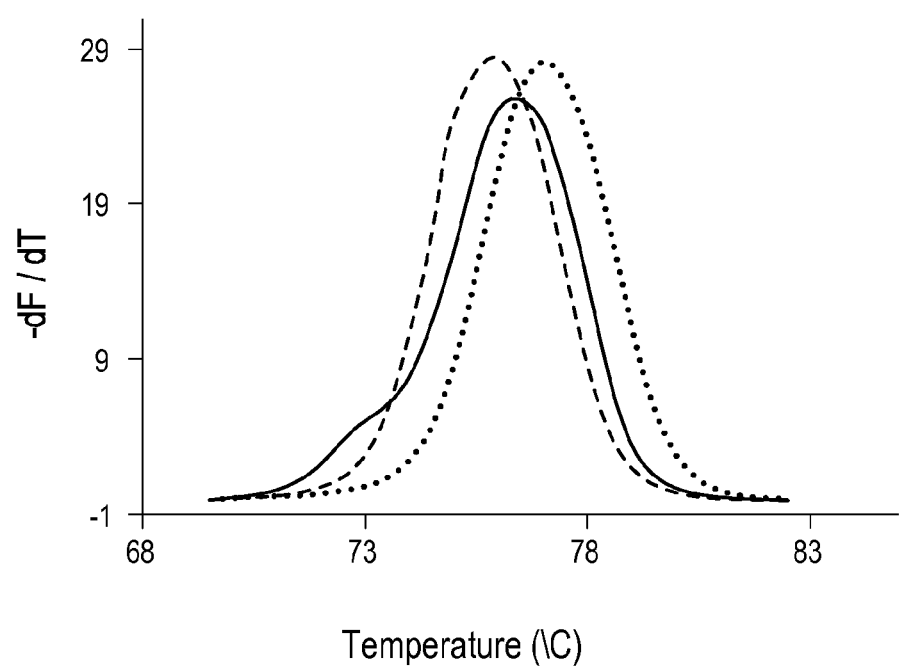

The rs917118 target was also used to demonstrate successful amplification under "0"s holding times, requiring only 3 minutes and 45 s to complete 35 cycles (see FIGS. 6A-6B). While the $C_q$ increased to 28 (see FIG. 6A), robust results were produced that enabled all 3 genotypes to be clearly identified (see FIG. 6B). FIG. 6B illustrates negative derivative melting curves analyzed using the quantum method of background removal. Illustratively, all 3 genotypes (wild-type (dotted line), variant (dashed line) and heterozygotes (solid line)) are clearly distinguishable.

Illustrative Results

It is noted that the results disclosed herein are illustrative only, and that different results may be observed when practicing certain embodiments of the present invention. As such, the following results are not intended to limit the scope of the present invention.

Figure 7:
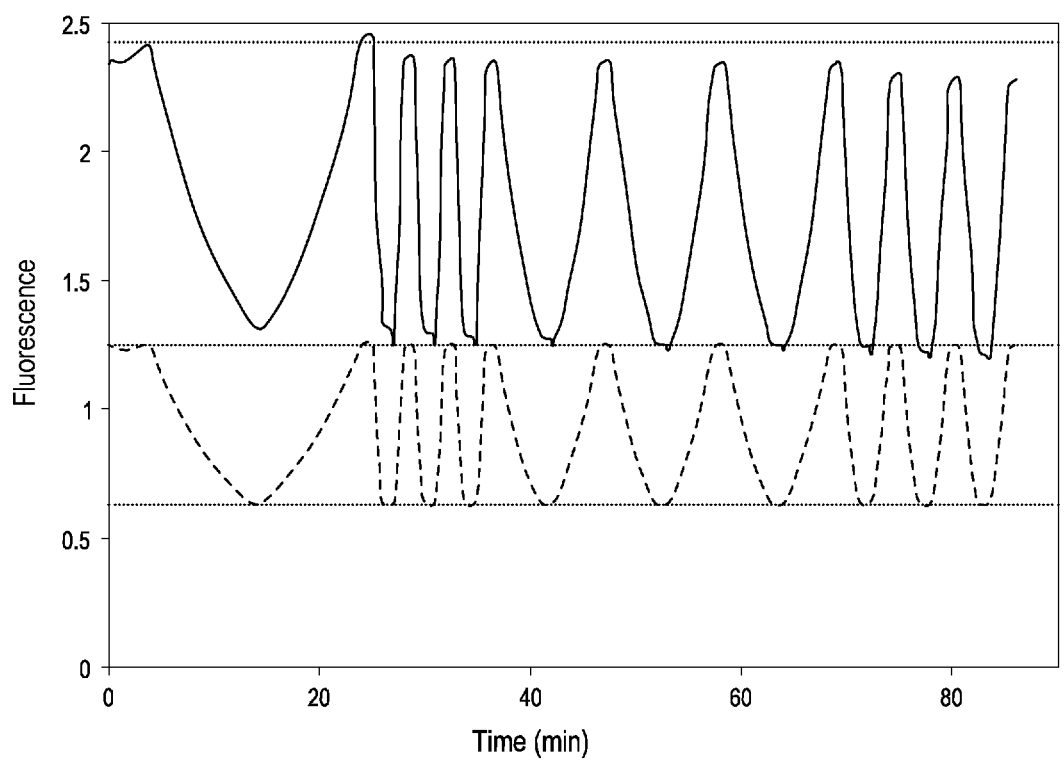
FIG. 7 illustrates fluorescence during heating and cooling on the LightCycler® 480 without (solid line) and with (dotted line) oil overlay.

In certain illustrative embodiments, in order for absolute fluorescence to serve as a temperature monitor, the instrument and reagent/dye should be substantially stable over time. Although many real-time PCR instruments use a heated lid instead of an oil overlay to limit evaporation and condensation, more consistent fluorescence readings may be obtained with oil than without it (see FIGS. 7-8). Oil overlays may stabilize fluorescence across multiple cycles, particularly during hold times and at temperature extremes (see FIG. 7).

In an illustrative example, a 70 µL reaction volume was compared to a 50 µL volume with a 20 µL oil overlay. Data illustrated in FIG. 7 include initial heating and cooling curves at 0.05° C./s followed by three cycles between 55° C. to 95° C. at ramp rates of 0.57, 0.11, and 0.29° C./s. The solid and dashed lines denote the absence and presence of an oil overlay, respectively. Dotted lines are for vertical alignment only. Without oil, fluorescence decreased about 8% per hour and short term anomalies were also present, effects that could affect solution temperature measurement by fluorescence.

Figure 8:
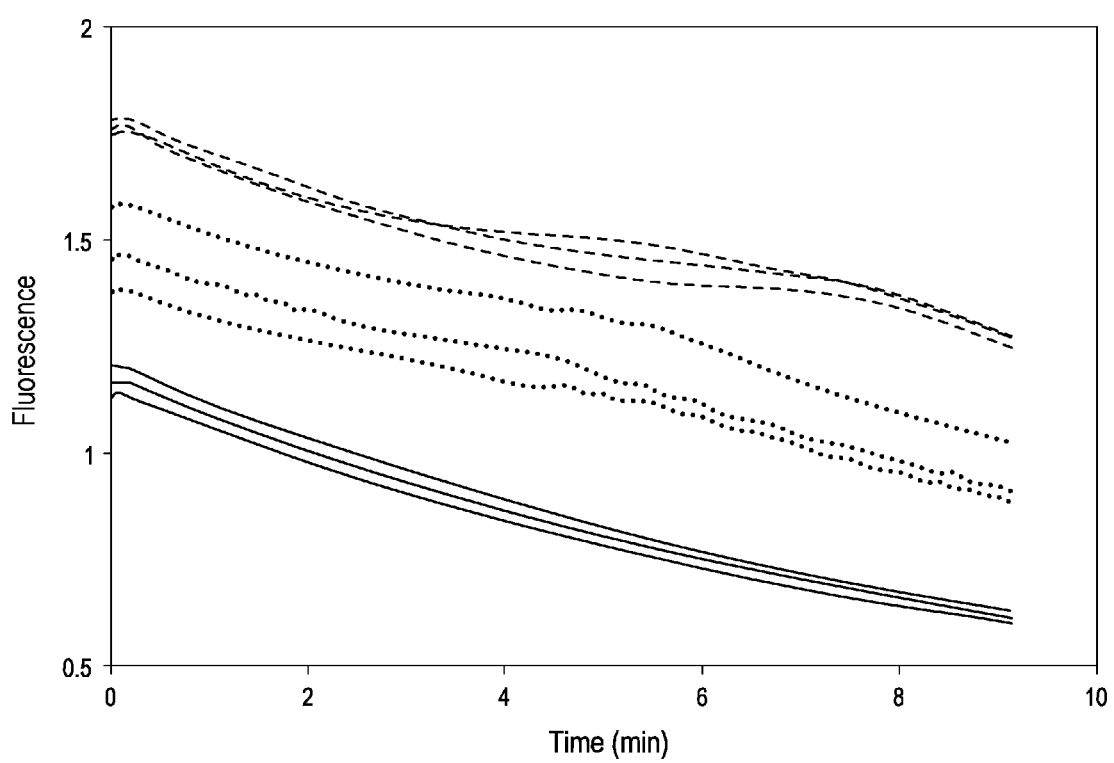
FIG. 8 illustrates fluorescence during heating on the LightCycler® 480.

Fluorescence artifacts may also be noted during temperature ramps typically used for melting curve analysis. For example, FIG. 8 illustrates (sulforhodamine B) fluorescence during heating on a LightCycler® 480 instrument, with an illustrative ramp rate of 0.05° C./s. Dashed lines denote a 10 µL sample volume with no oil overlay, dotted lines denote a 8 µL sample volume with a 2 µL oil overlay, and solid lines denote a 5 µL sample volume with a 5 µL oil overlay. With too little or no oil overlay, undulating curves were observed that could be mistaken for PCR products when displayed on derivative plots. Only those samples with an appropriate oil overlay showed a smooth decrease of fluorescence with time and temperature. Illustratively, oil overlay may improve results on any and/or all instruments, although changes may be minimal on capillary instruments. However, it is understood that oil overlay is illustrative only, and other techniques may be used to stabilize fluorescence.

In addition to evaporation and/or condensation, other potential artifacts affecting fluorescence may include instrument drift (sometimes referred to as "warm up" of the instrument), thermal degradation of the dye, and fluorescence quenching (each of which will now be addressed in turn).

With some instruments, although some initial instrument drift may be observed, this may be reduced substantially by "warming" up the instruments (illustratively, for 20 minutes). For example, in certain illustrative examples, when samples were incubated at 50, 80, or 94° C., minor instrument drifts up to +/−4% fluorescence were seen over the first 20 minutes (see FIGS. 9A-9C and 10A-10C) on three different instruments. After 20 minutes, any change in fluorescence over time may become relatively linear.

Figure 9A:
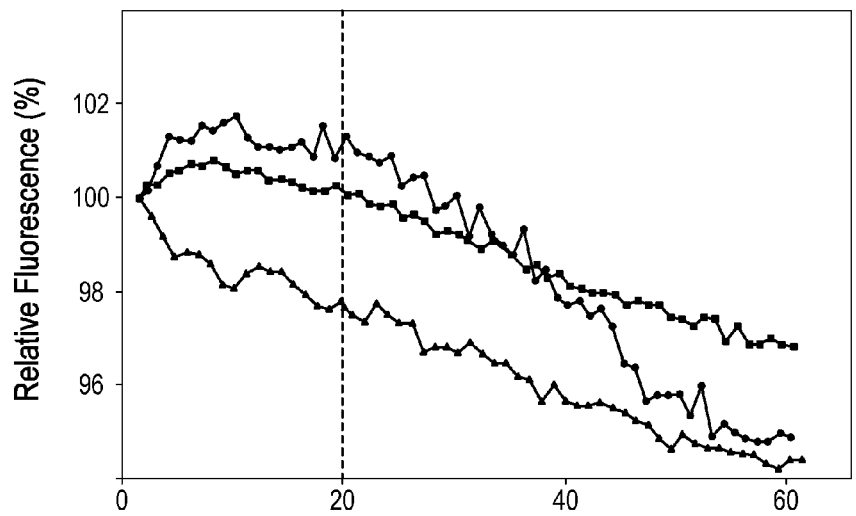
FIGS. 9A-9C illustrate instrument equilibration and thermal degradation of sulforhodamine B assessed at 94° C.
Figure 9B:
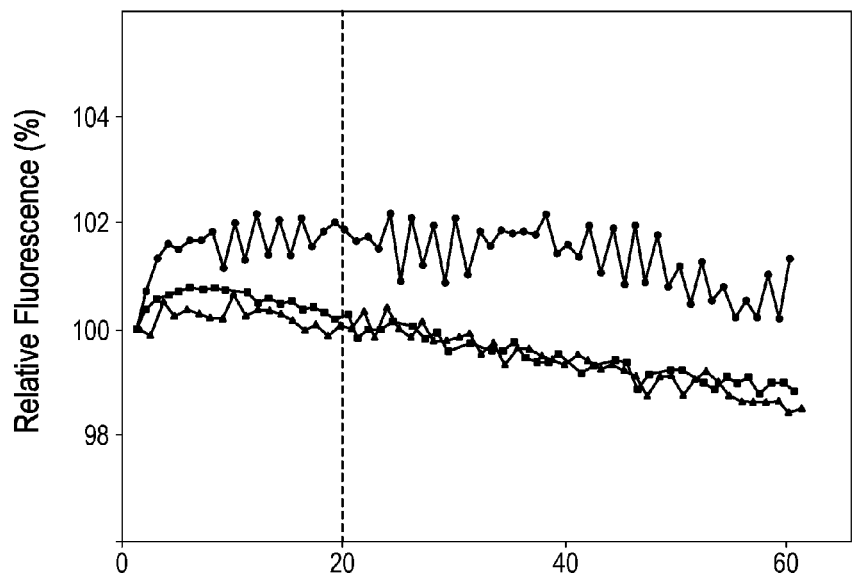
Figure 9C:
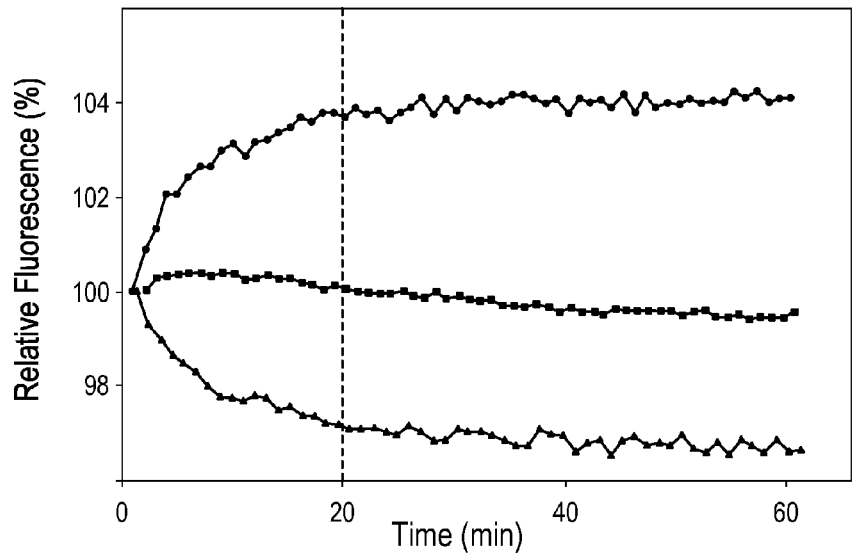

Furthermore, in at least one embodiment, no substantial thermal degradation of a temperature-sensitive reagent may be observed at certain (lower) temperatures, while a measurable amount of thermal degradation may be observed at other (higher) temperatures. For example, FIGS. 9A-9C show that in certain illustrative embodiments, after instrument equilibration, average sulforhodamine B fluorescence may be stable substantially at 50° C. (FIG. 9C), decrease about 2.2%/hour at 80° C. (FIG. 9B), and/or decrease about 5.4%/hour at 94° C. (FIG. 9A) for one or more of a LightCycler® 1.5 (filled circle), LightCycler® 2.0 (filled square), and LightCycler® 480 (filled triangle). Illustratively, for the first 20 minutes (dashed line) fluorescence is variable as the instrument equilibrates. After 20 minutes, fluorescence decreases at a temperature-dependent rate. Instruments were turned off for 1 hour between each experiment. Across all instruments, the average change in fluorescence was less than about 1%/hour at 50° C., 2.2%/hour at 80° C., and 5.4%/hour at 94° C. Thus, minor thermal degradation of the dye may occur under certain conditions and may be both temperature and time dependent.

In certain embodiments, this temperature-dependent degradation may be reduced by rapid cycling to minimize denaturation and overall cycling times (an illustrative embodiment in which fluorescence monitoring of temperature is highly useful). Another option for fluorescent estimation of temperature is to use fluorescence ratios so that the requirements for absolute fluorescence stability are not so strict.

Figure 10A:
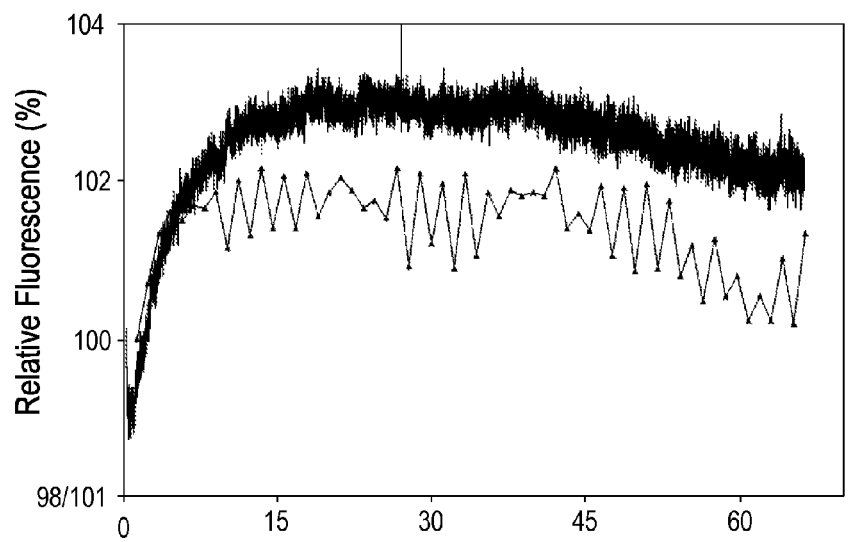
FIGS. 10A-10C illustrate fluorescence quenching of sulforhodamine B at 80° C. on a LightCycler® 1.5 (FIG. 10A), LightCycler® 2.0 (FIG. 10B), and LightCycler® 480 (FIG. 10C).
Figure 10B:
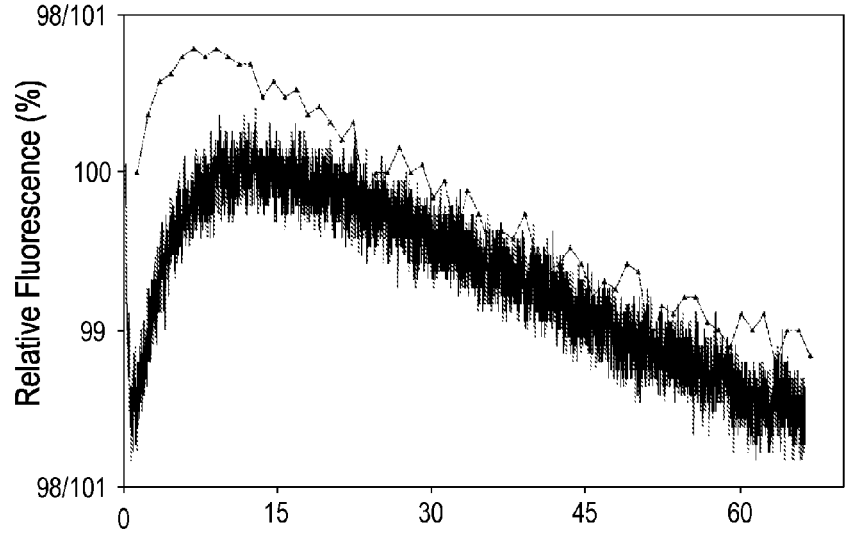
Figure 10C:
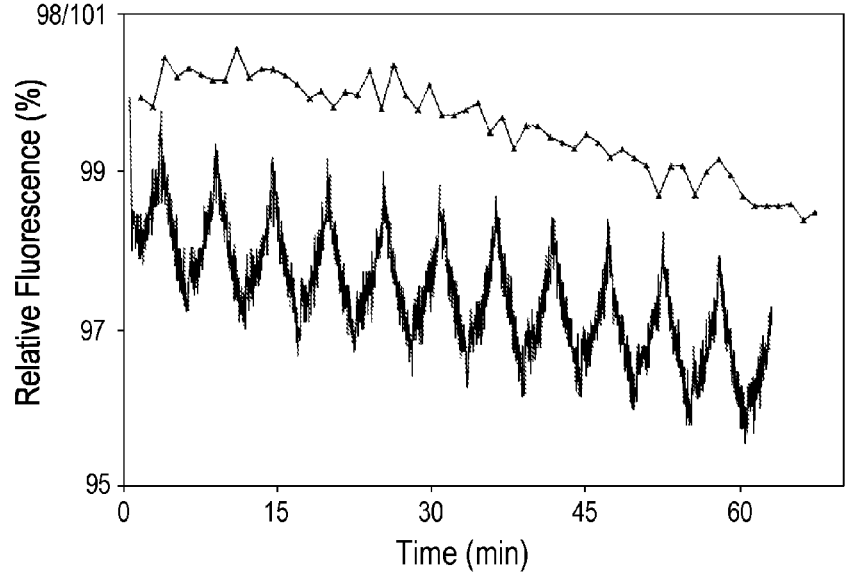

In certain illustrative embodiments, no substantial fluorescence quenching may be observed (for sulforhodamine B, illustratively). For example, FIGS. 10A-10C show no appreciable fluorescence quenching of sulforhodamine B over one hour at 80° C. on a LightCycler® 1.5 (FIG. 10A), LightCycler® 2.0 (FIG. 10B), and LightCycler® 480 (FIG. 10C). In some embodiments, after instrument equilibration, fluorescence decreases at about 2.2%/hour, irrespective of whether the samples are continuously illuminated (solid lines) or only illuminated once each minute (filled triangles). This decrease is consistent with thermal degradation alone (see FIGS. 9A-9C), with no apparent and/or substantial contribution of fluorescence quenching. During typical cycling, sulforhodamine B fluorescence decreased by 0.1% at extension (runtime 17 minutes) on an illustrative capillary instrument compared to 0.7% on an illustrative plate instrument (runtime 60 minutes). In one illustrative example, due to programming constraints associated with continuously acquiring data on the LightCycler® 480, multiple segments that cycled between 79° C. and 80° C. were programmed during the 1 hour hold period (see FIG. 10C).

In an illustrative embodiment, to test potential inhibition of PCR by sulforhodamine B, quantitative real-time PCR results, gel analysis, and high-resolution melting curves were examined. Samples containing sulforhodamine B had quantification cycles that differed by only about 0.10 when compared to standard samples containing no sulforhodamine B. Gel analysis confirmed both the purity and size of the product in samples containing sulforhodamine B. Finally, high-resolution melting curves comparing standard samples to those with sulforhodamine B were similar in intensity and peak temperature.

Figure 11A:
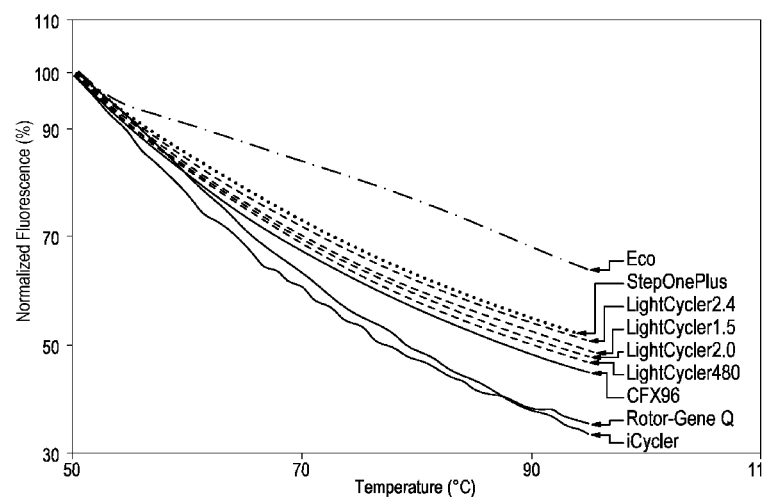
FIG. 11A illustrates calibration curves correlating temperature to fluorescence on nine real-time PCR instruments. Instruments included Class I (dashed lines), Class II (solid lines), Class III (dotted line) and Class IV (dash-dotted line).
Figure 11B:
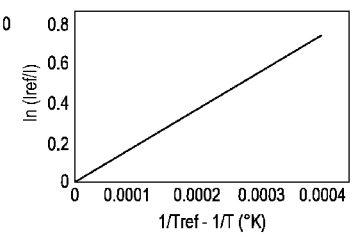
FIG. 11B illustrates the slope of a linear plot of the data illustrated in FIG. 5A for the LightCycler® 1.5 (y=1890X+0.013, R2=0.999).

Calibration curves for nine illustrative instruments are shown in FIG. 11A. Instruments included Class I (dashed lines), Class II (solid lines), Class III (dotted lines) and Class IV (dash-dot lines). In an illustrative example, slow heating rates (0.018-0.1° C./s) were used to equilibrate solution and instrument temperatures. Eight of the nine instruments successfully monitored sulforhodamine B fluorescence, even though the excitation wavelengths of many real-time instruments were not optimal for sulforhodamine B. In certain illustrative embodiments, the fluorescence of sulforhodamine B approximately doubles as the temperature decreases from 95 to 50° C. (see e.g. Class II (solid lines) instruments). For one illustrative example (the Eco™ instrument) fluorescein was used because of available optics (i.e., fluorescein was compatible with the fixed melting emission wavelength available), resulting in a calibration curve of different shape than the sulforhodamine B curves. In certain embodiments, fluorescein fluorescence increases about 60% as the temperature decreased from 95 to 50° C. Calibration constants were derived from the slope of linear plots of the data (as shown in FIG. 11B for the LightCycler® 1.5 (y=1890X+0.013, R2=0.999)). By way of illustration only, the calibration constant was 1097 for fluorescein and ranged from 1787 to 2831 for sulforhodamine B (see Table 5 below). Without being bound to theory, the different calibration constants for sulforhodamine B among instruments presumably arise from different optical characteristics and efficiencies.

TABLE 5

Solution Temperatures during Denaturation, Annealing, and Extension Segments

| Instrument | Calibration Constant[a] | Cycle Time[b] (s) | Hold Time[c] (s) | Solution Temperatures[d] (° C.) Target = 94° C. | Target = 55° C. | Target = 74° C. |
|---|---|---|---|---|---|---|
| LightCycler 24 | 1787 | 18[c] | 10 | 88.5 | 57.9 | 70.8-73.1 |
| ghtCycler 1.5 | 1890 | 27[c] | 10 | 95.1 | 56.2 | 76.5-76.2 |
| LightCycler 2.0 | 1953 | 25[c] | 10 | 92.3 | 56.1 | 73.7-75.4 |
| LightCycler 480[e] | 2042 | 79 | 1, 2, 5, 10, 20, 50 | 85.4-92.4 | 59.5-54.8 | 68.2-73.5 |
| Rotor-Gene Q | 2831 | 85 | 1, 2, 5, 10, 20, 50 | 93.3-91.3 | 59.2-57.4 | 77.7-77.1 |
| iCycler | 2661 | 120 | 5, 7, 10, 15, 20, 50 | 87.4-93.3 | 58.3-53.3 | 67.5-66.8 |
| CFX96 | 2122 | 80 | 1, 2, 5, 10, 20, 50 | 94.8-95.5 | 57.0-56.3 | 75.3-76.7 |
| StepOnePlus | 1779 | 78 | 10, 15, 20, 30, 50 | 94.9-97.7 | 56.4-54.7 | 73.8-75.1 |
| Eco | 1097 | 66 | 1, 2, 5, 10, 20, 50 | 85.6-95.9 | 58.1-56.2 | 73.6-72.3 |

[a]The calibration constant is a unitless constant defined the slope of the linear line formed by plotting (1/T(K) − 1/Tref(K)) against ln(I/Iref). See FIG. 11B and U.S. patent application Ser. No. 61/872,173, already incorporated by reference. All calibration constants are for sulforhodamine B except for the Eco instrument (fluorescein).
[b]Time required to complete a 94° C., 55° C., 74° C. cycle using hold times as recommended by the manufacturer, that is, 10 s at each segment for all instruments except the capillary LightCyclers, where 0 s was used for denaturation and annealing. Cycle times were obtained by monitoring a single sample on the LightCycler instruments.
[c]Hold times at each segment, except for the capillary LightCyclers where 0 s was used at denaturation and annealing.
[d]The temperature range indicates the minimum and maximum solution temperatures at the holding times monitored. Only a single value at the peak is given for the 0 s holds at denaturation and annealing on the capillary LightCyclers.
[e]The sample volume was 10 μl covered with 15 μl of oil.

In certain illustrative embodiments, using fluorescence as a temperature monitor during PCR may be dependent on data acquisition that may vary greatly from device to device, ranging from one data point per cycle to continuous acquisition. Similarly, the exportable data may vary from only cycle number and fluorescence, to comprehensive spreadsheets including time, program, cycle, segment, fluorescence and temperature. Software and available optics may also restrict the excitation and emission wavelengths that can be used. Even with these limitations, sample temperatures may be successfully monitored by fluorescence on many different instruments (including all the instruments disclosed herein), albeit some with greater difficulty than others.

Figure 12:
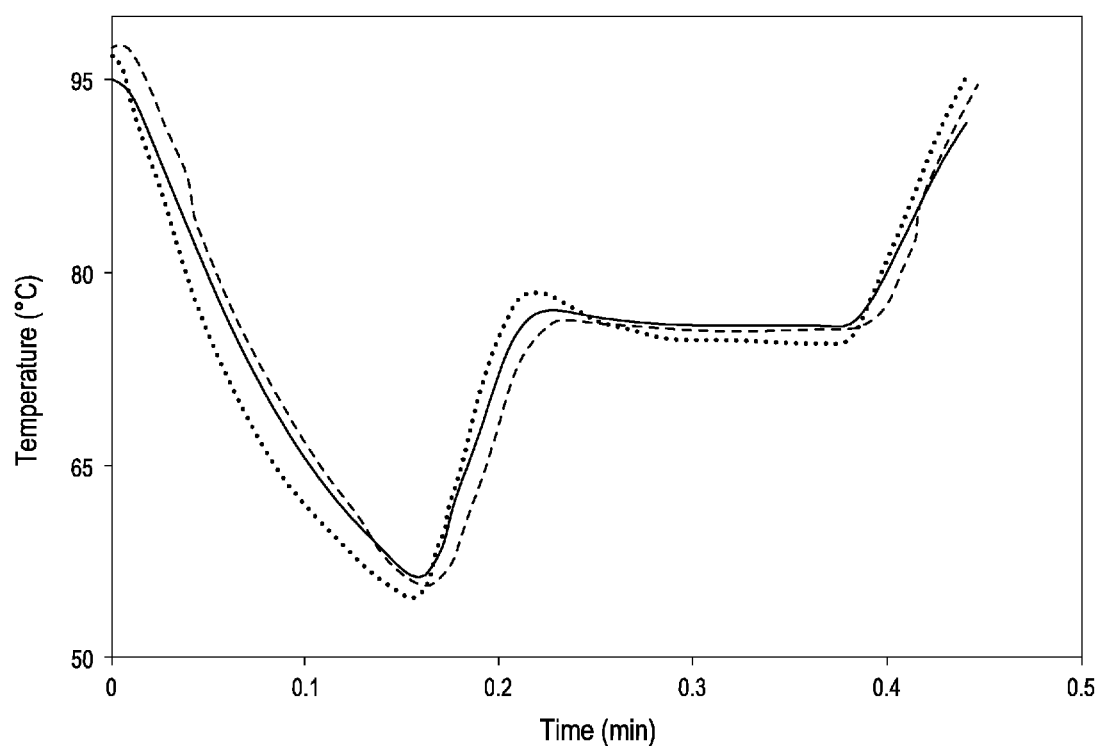
FIG. 12 illustrates temperature traces of a typical PCR cycle on a LightCycler® 1.5 determined by fluorescence ("Solution"—solid line), a micro-thermocouple ("Thermocouple"—dashed line), and displayed by the instrument ("Instrument"—dotted line).

Different instruments may vary greatly in their fluorescence collection capabilities during temperature cycling. In an illustrative example, continuous acquisition throughout temperature cycling and melting was only possible on Class I instruments. Furthermore, the greatest data density and cycling speeds were obtained on the capillary Class I instruments, although only one sample could be measured at a time. Individual samples were monitored throughout rapid cycle PCR with cycle times varying between 18-25 s depending on the instrument model. Solution temperatures (derived from fluorescence) (solid line) were compared to instrument (dotted line) and thermocouple (dashed line) readings on 3 capillary Class I instruments, and the results for one model (a LightCycler® 1.5, illustratively) are shown in FIG. 12.

By way of example only, the instrument was programmed for maximum transition rates (20° C./s), but achieved rates between 3.7-7.0° C./s during heating and 1.9-8.0° C./s during cooling. The extension temperature target was 74° C. with a 10 s hold, using denaturation (94° C.) and annealing (55° C.) temperature spikes ("0" s hold). Cycle time was 27 s. In certain embodiments, discrepancies between temperatures are exacerbated during rapid transitions and minimized during hold periods. During rapid transitions, the thermocouple trace best aligns with the solution temperature, both lagging behind the instrument temperature. Thus, in certain embodiments, solution and thermocouple temperatures may cluster together and may lag behind the instrument temperature trace.

At least one heating block instrument (the LightCycler® 480, illustratively) may also be classified as a Class 1 instrument because fluorescence may be monitored throughout temperature cycling. In certain embodiments, up to 96 or 384 samples may be monitored simultaneously and both excitation and emission wavelengths may be flexible. However, when fluorescence is acquired continuously, the ramp rate may be limited to 0.57° C./s or less—slower than typical PCR cycles.

Figure 13A:
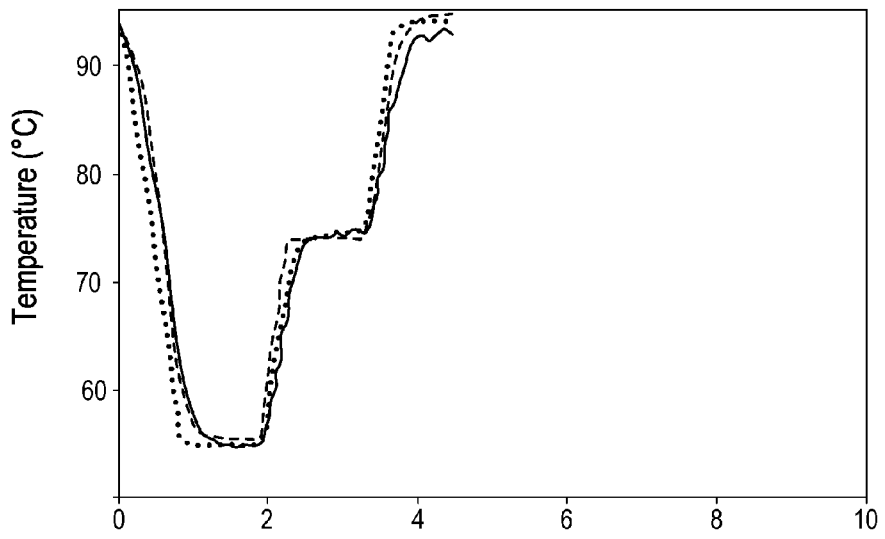
FIGS. 13A-13C illustrate temperature traces of PCR cycles on a LightCycler® 480 determined by fluorescence ("Solution"—solid lines), a micro-thermocouple ("Thermocouple"—dashed lines), and displayed by the instrument ("Instrument"—dotted lines) for a 30 μL sample+20 μL oil at 0.57° C./s (FIG. 13A), a 10 μL sample+15 μL oil at 0.29° C./s (FIG. 13B), and a 5 μL sample+5 μL oil at 0.14° C./s (FIG. 13C).
Figure 13B:
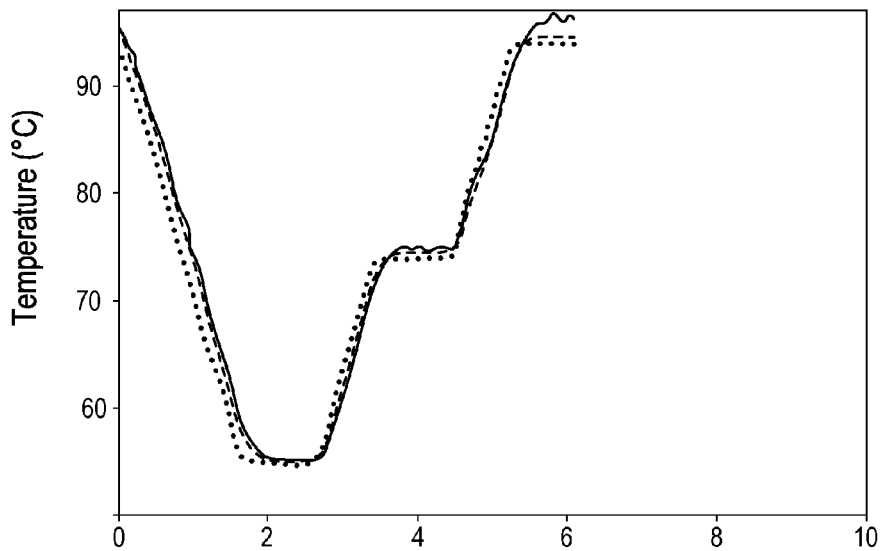
Figure 13C:
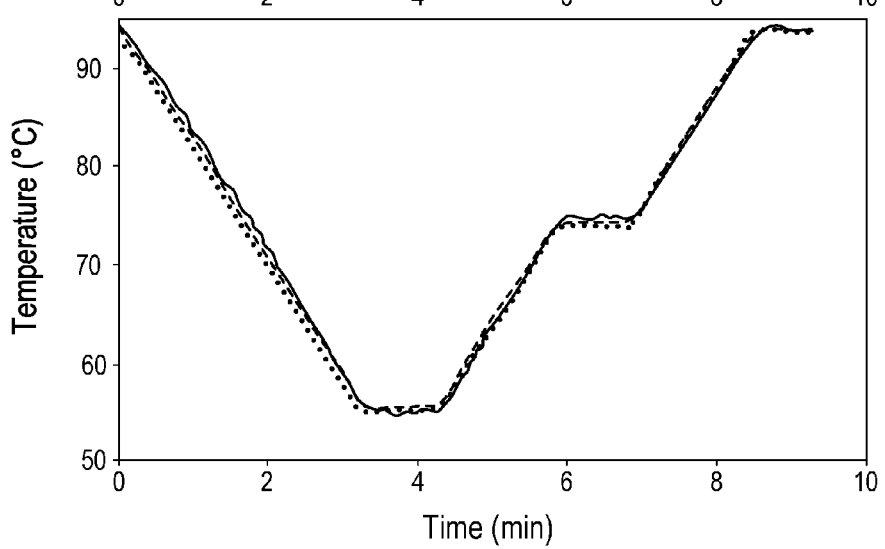

In one illustrative example, three different combinations of sample volumes and ramp rates were studied to examine instrument (dotted lines), thermocouple (dashed lines), and solution (solid lines) temperature mismatch during PCR cycling (see FIGS. 13A-13C). The target temperatures were 94° C. for denaturation, 55° C. for annealing, and 74° C. for extension, all with 10 s holds. The volumes and transition rates were (FIG. 13A) 30 μL sample+20 μL oil at 0.57° C./s, (FIG. 13B) 10 μL sample+15 μL oil at 0.29° C./s, and (FIG. 13C) 5 μL sample+5 μL oil at 0.14° C./s. Cycle times were 4.5, 6.1 and 9.3 min, respectively—10-20 fold slower than on the capillary instruments. Calibration constants were determined under each condition and were 1977, 2042, and 2055, respectively. As with the capillary LightCyclers, the solution and thermocouple temperature traces clustered together and lagged behind the instrument readings, particularly during temperature transitions.

In certain illustrative embodiments, the solution and thermocouple temperatures may track together and may be averaged as the best estimate of sample temperature, then quantitatively compared to the displayed instrument temperature. Table 6 (below) lists, as an illustrative example, the mean differences between sample and instrument temperatures during transitions on both capillary and 96-well Class I instruments. Illustratively, sample temperatures consistently lagged behind instrument readings and differences were greatest with faster transition rates and larger sample volumes on the 96-well plate, reaching a maximum difference of about 5.1° C. during cooling and about 4.5° C. during heating with 50 μL volumes and a transition rate of 0.57° C./s. Even though the transition rates with capillaries may be 10-20 fold faster than on a 96-well plate, temperature discrepancies may be less, illustratively averaging about 3.8° C. during cooling and about 0.4° (approach to extension) and about 1.4° C. (approach to denaturation) during heating.

Another illustrative way to quantify temperature mismatches is the time required for the sample temperature to reach the instrument reading (see Table 6). In the illustrative example shown in Table 6, the capillary format had an average lag or delay time of 0.47 s across all transitions, compared to 5.0 s for the 96-well plate. The maximum time delay on the 96-well plate was 8.3 s, occurring during the approach to denaturation with 50 μL samples at a transition rate of 0.57° C./s.

TABLE 6

Sample and instrument temperature differences and time delays during temperature transitions.

| | LC 1.5 | LC480 | LC480 | LC480 |
|---|---|---|---|---|
| Volume (sample + oil, μL) | 10 + 2 | 5 + 5 | 10 + 15 | 30 + 20 |
| Transition Rate (° C./s) | 20[b] | 0.14 | 0.29 | 0.57 |
| Cycle Time (min) | 0.44 | 9.3 | 6.1 | 4.5 |

| Temperature Transition | Difference between Sample and Instrument Temperatures (° C., Mean ± SD) | | | |
|---|---|---|---|---|
| 95 to 55° C. | −3.8 ± 1.5 | −1.3 ± 0.2 | −3.1 ± 0.3 | −5.1 ± 1.5 |
| 55 to 74° C. | 0.4 ± 2.3 | 0.2 ± 0.2 | 1.6 ± 0.6 | 4.5 ± 0.6 |
| 74 to 95° C. | 1.4 ± 1.5 | 0.1 ± 0.3 | 1.3 ± 0.7 | 3.4 ± 1.9 |

| Temperature Transition | Time Delay (s, mean) | | | |
|---|---|---|---|---|
| 95 to 55° C. | 0.5 | 6.1 | 7.7 | 6.1 |
| 55 to 74° C. | 0.6 | 1.4 | 4.4 | 4.8 |
| 74 to 95° C. | 0.3 | 2.0 | 4.1 | 8.3 |

Continuous monitoring of fluorescence throughout cycling may not be possible on certain instruments (e.g., class II-IV instruments, illustratively). However, in certain embodiments, a single fluorescence acquisition during a holding segment may be sufficient to determine the solution temperature. Accordingly, in some embodiments, a temperature trace can be reconstructed by acquiring different time points on multiple runs. The minimum time before acquisition may vary between instruments, ranging from about 1 to 10 s (or more). In at least one embodiment, holding times up to 50 s (or more) may be analyzed (see Table 5).

Considering all instruments, the first instrument temperature readings obtained during the annealing holds may be approximately 1.1-4.5° C. too high. Also, it is noted that the greatest temperature errors in one illustrative embodiment were 8.4 and 8.6° C. too cool after 1 s of denaturation on 2 different instruments.

Figure 14:
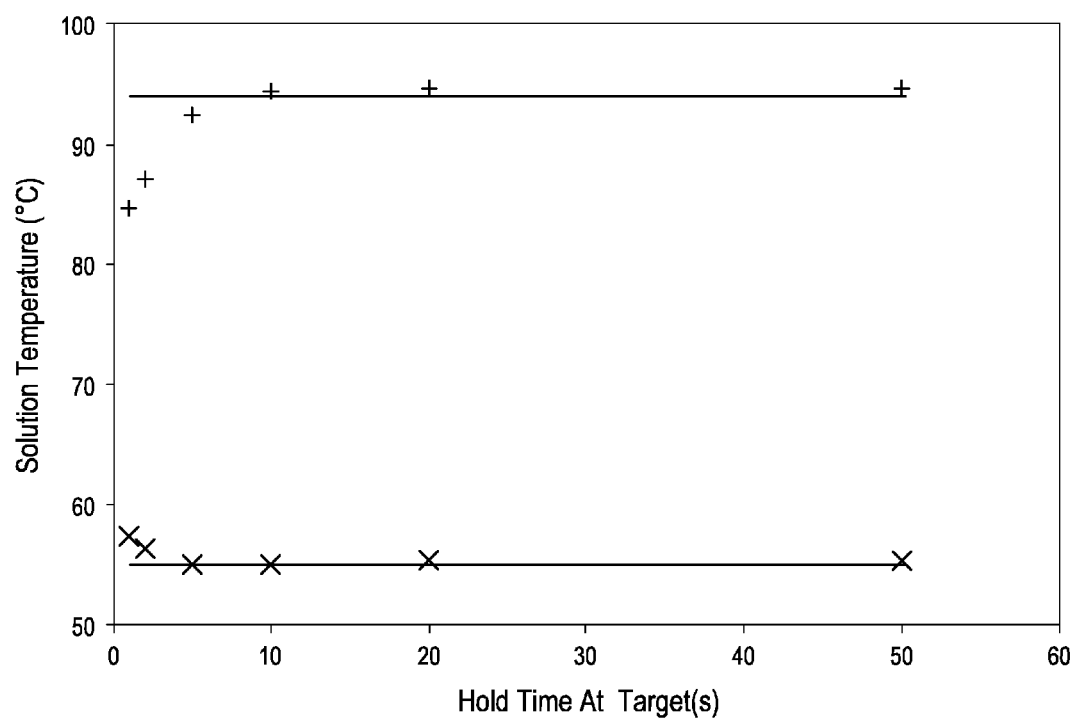
FIG. 14 illustrates solution temperature measurements determined by fluorescence during denaturation (+) and annealing (x) segment holds on the Eco™ instrument. The denaturation (94° C.) and annealing (55° C.) temperature targets are shown as solid horizontal lines.

An embodiment in which solution temperatures are determined during illustrative denaturation (+) and annealing (x) holds on a Class IV instrument is shown in FIG. 14. Solution temperature measurements may be determined by (fluorescein) fluorescence during denaturation (94° C. temperature target) and annealing (55° C. temperature target) segment holds on an Eco™ instrument. In at least one embodiment, after one second of annealing, the solution temperature may be 3.1° C. too hot. Similarly, after one second of denaturation, the solution temperature may be 8.4° C. too cool. Accordingly, up to five to 10 s (or more) of programmed hold times may be required for the solution to equilibrate near the target temperatures.

Figure 15A:
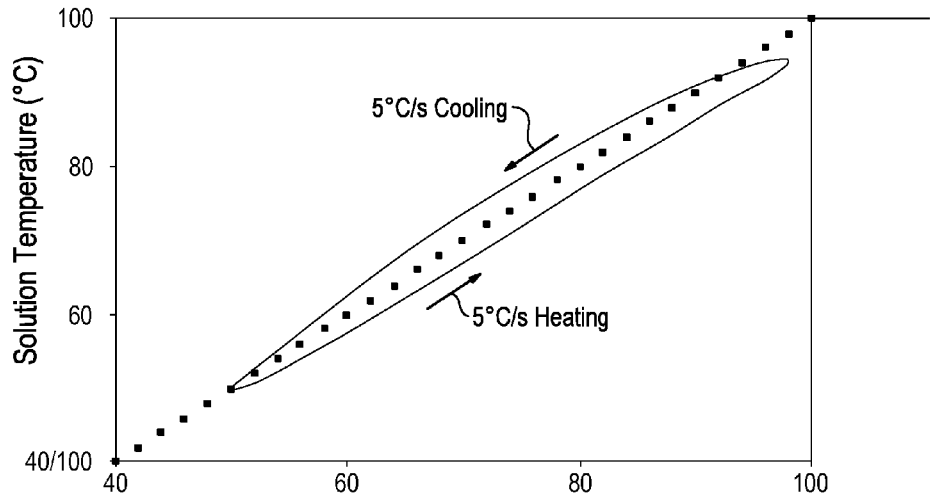
FIGS. 15A-15C illustrate temperature mismatch or hysteresis between the solution and instrument temperatures during heating and cooling on the LightCycler® 1.5 (FIG. 15A), LightCycler® 480 (FIG. 15B), and Rotor-Gene® Q (FIG. 15C). Ideal solution-instrument temperature correlations are shown as dotted lines.
Figure 15B:
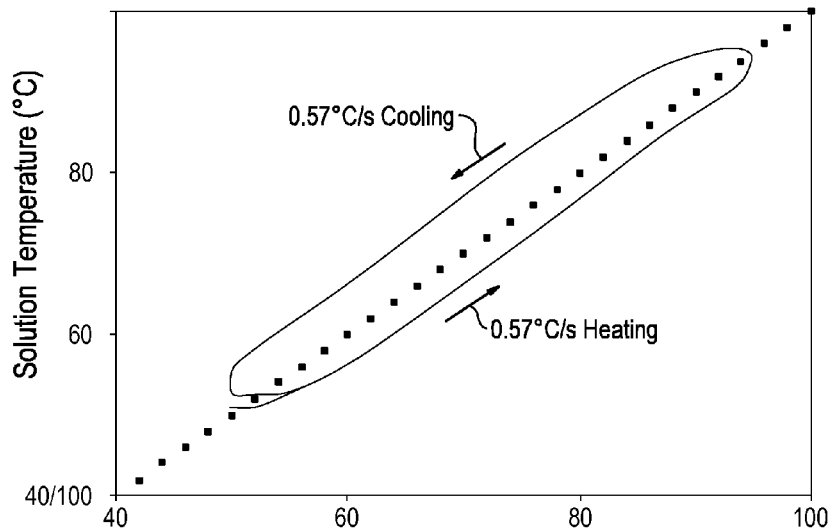
Figure 15C:
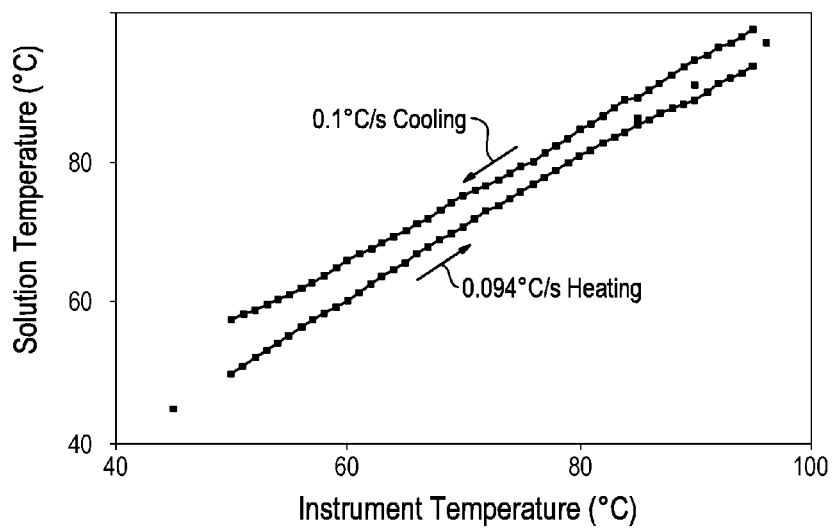
Figure 16A:
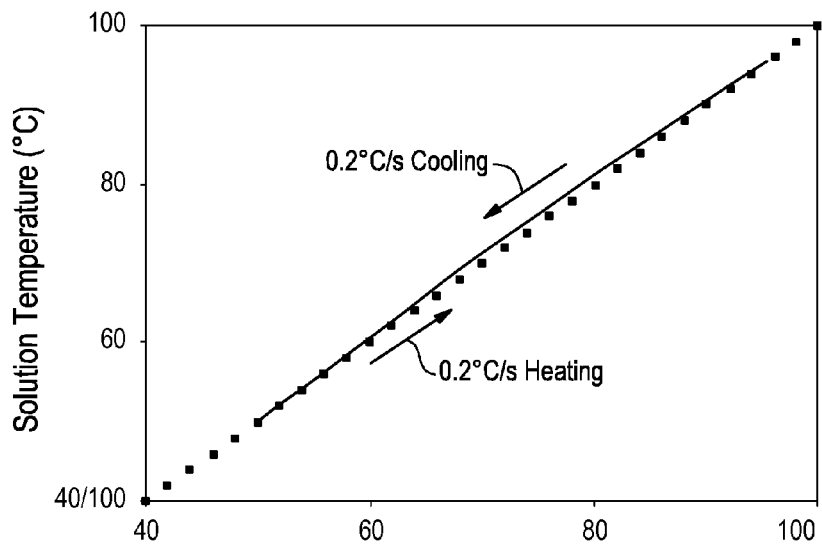
FIGS. 16A-16F illustrate solution-instrument temperature hysteresis during heating and cooling on a LightCycler® 1.5 capillary instrument (FIGS. 16A-16C) at 0.2° C./s (FIG. 16A), 1° C./s (FIG. 16B), and 5° C./s (FIG. 16C) ramp rates, and on a plate-based instrument at (FIGS. 16D-16F) at 0.11° C./s (FIG. 16D), 0.29° C./s (FIG. 16E), and 0.57° C./s (FIG. 16F) ramp rates.
Figure 16B:
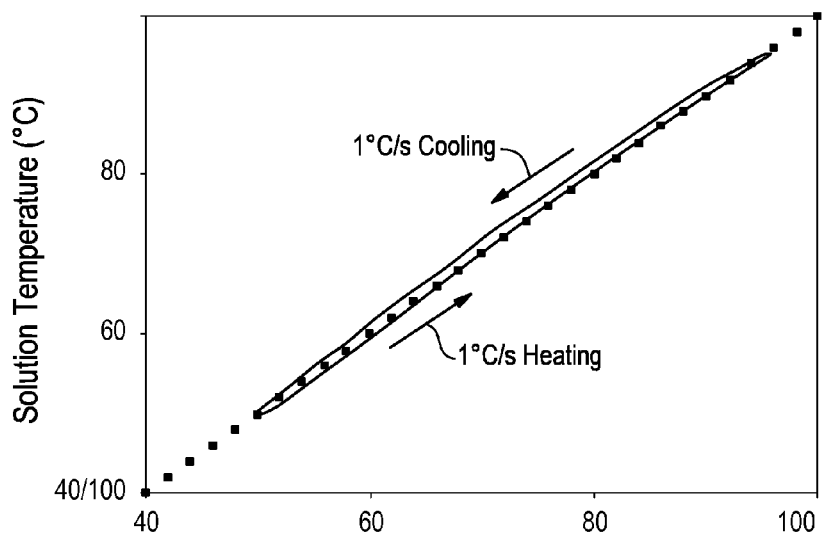
Figure 16C:
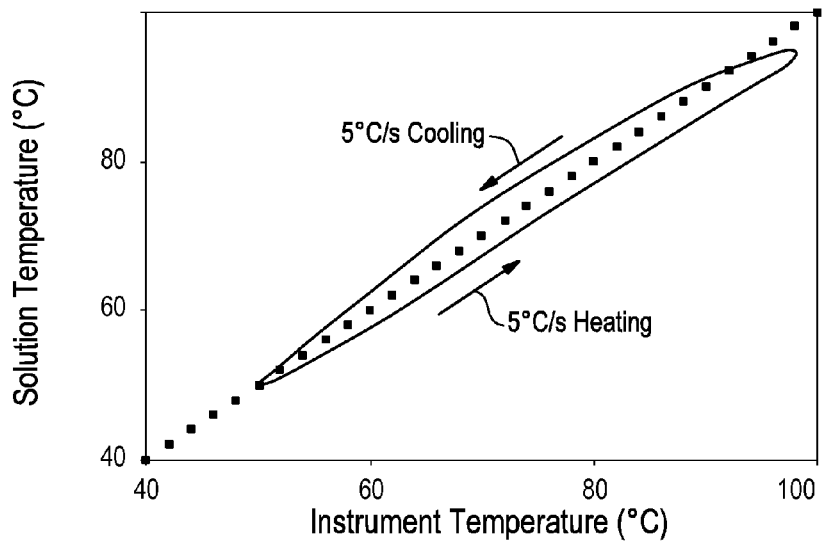
Figure 16D:
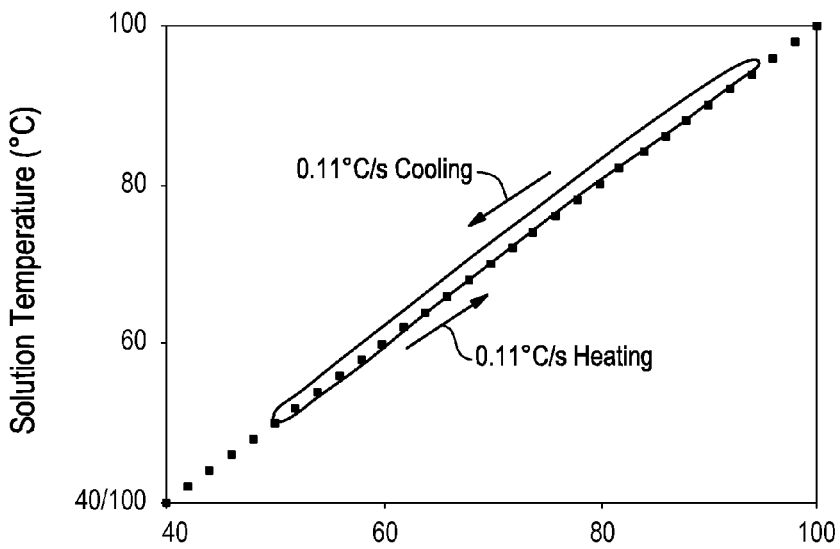
Figure 16E:
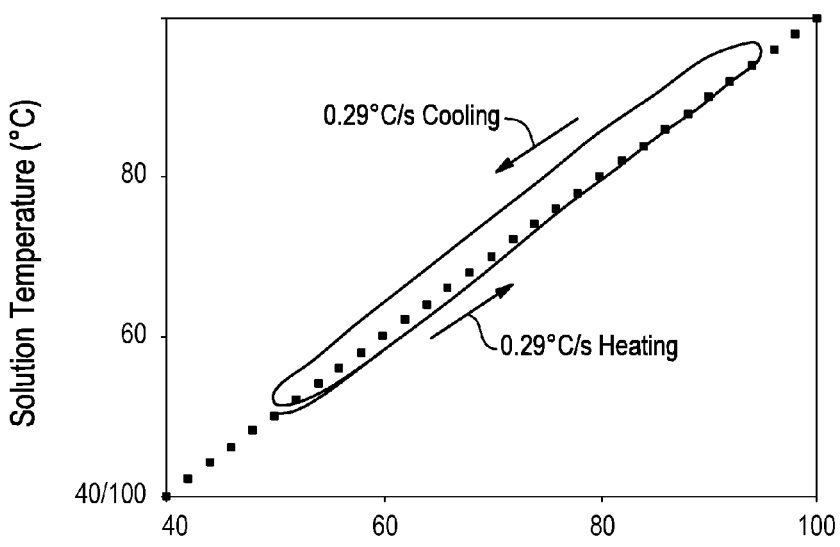
Figure 16F:
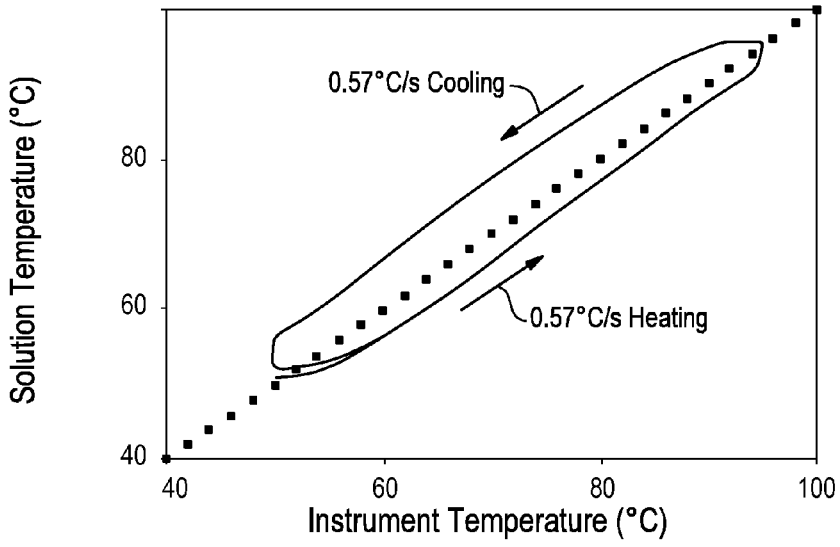

Thus, in certain embodiments, a continuous trace of the solution temperature derived from fluorescence may illustrate that thermocouple and solution temperatures cluster together and both lag behind the instrument temperature during typical PCR cycles. Thus, instruments may display and/or indicate that a target temperature has been reached before the sample has, in fact, reached the target temperature. Discrepancies between sample and instrument temperatures may depend on the instrument and may be greater during cooling than heating transitions. Furthermore, greater errors may occur at faster cycling speeds. The magnitude of the instrument errors during transitions may be about 1-5° C. and/or may exceed 5° C. under some conditions Another way to demonstrate differences between solution and instrument temperatures on Class I-II instruments is by the mismatch or hysteresis between heating and cooling segments. By way of example, temperature hysteresis (lag of the solution temperature compared to the instrument temperature) may be displayed by plotting both measurements against each other during heating and cooling (see FIGS. 15A-15C). FIGS. 15A-15C illustrate temperature mismatch or hysteresis between the solution and instrument temperatures during heating and cooling on the LightCycler® 1.5 (FIG. 15A), LightCycler® 480 (FIG. 15B), and Rotor-Gene® Q (FIG. 15C). Ideal solution-instrument temperature correlations are shown as dotted lines. On Class I instruments (FIGS. 15A and 15B) multiple cycles were achieved by concatenating heating and cooling segments without pause between them (3 cycles are shown). On the Class II instrument (FIG. 15C), although heating and cooling segments could be connected, fluorescence acquisitions were discontinued during a mandatory pause for equilibration (one heating and one cooling segment are shown). Ramp rates were 5° C./s for the LightCycler® 1.5, 0.57° C./s (9 times slower) on the LightCycler® 480, and 0.1° C./s (5.7 time slower yet again) on the Rotorgene Q. Solution to instrument temperature differences reached a maximum of 4.5° C. on the LightCycler® 1.5, 8.1° C. on the LightCycler® 480, and 7.5° C. on the Rotorgene Q.

FIGS. 16A-16F illustrate solution-instrument temperature hysteresis during heating and cooling on capillary and plate-base instruments. Instrument and solution temperatures were compared on a capillary instrument (LightCycler® 1.5) at 0.2° C./s (FIG. 16A), 1° C./s (FIG. 16B) and 5° C./s (FIG. 16C) ramp rates. Ideal solution-temperature correlations are noted by a dotted line on each graph. In some embodiments, data generated at the 0.2° C./s ramp rate may closely align to the ideal for both heating and/or cooling. However, at 5° C./s, the discrepancy between instrument and solution temperatures may reach up to 4.5° C.

Instrument and solution temperature differences were also examined on a plate-based instrument (LightCycler® 480) at 0.11° C./s (FIG. 16D), 0.29° C./s (FIG. 16E), and 0.57° C./s (FIG. 16F) ramp rates, all using 30 μL sample and 20 μL oil. In certain embodiments, the maximum discrepancy between instrument and solution temperatures may reach 8.1° C. or higher. In at least one embodiment, even at the slowest ramp rate (0.11° C./s), hysteresis levels may be comparable to those present at a rate of 1° C./s on the capillary instrument, suggesting that sample format and methods of heat transfer may be of importance.

Illustratively, all instruments studied showed hysteresis loops, indicating a mismatch between solution and instrument temperatures during heating and cooling. In certain embodiments, temperature mismatches may be exaggerated at faster ramp rates (see FIGS. 15A-15C and FIGS. 16A-16F), although some instruments may be inherently better matched than others. For example, a capillary instrument run at 5° C./s may show less hysteresis than a 96-well instrument run at 0.57° C./s and/or about the same hysteresis as another 96-well instrument run at 0.1° C./s (see FIGS. 15A-15C and FIGS. 16A-16F).

Therefore, the large temperature differential observed at faster ramp rates may also be confirmed by temperature hysteresis of concatenated heating/cooling transitions showing loops with areas reflecting the magnitude of the temperature errors (see FIGS. 15A-15C and FIGS. 16A-16F). As a result, the time delay required for the sample to reach the indicated instrument temperature during transitions may be up to 0.3-0.6 s or more for air/capillary systems and up to 1.4-8.3 s or more for typical 96-well format instruments.

Figure 17A:
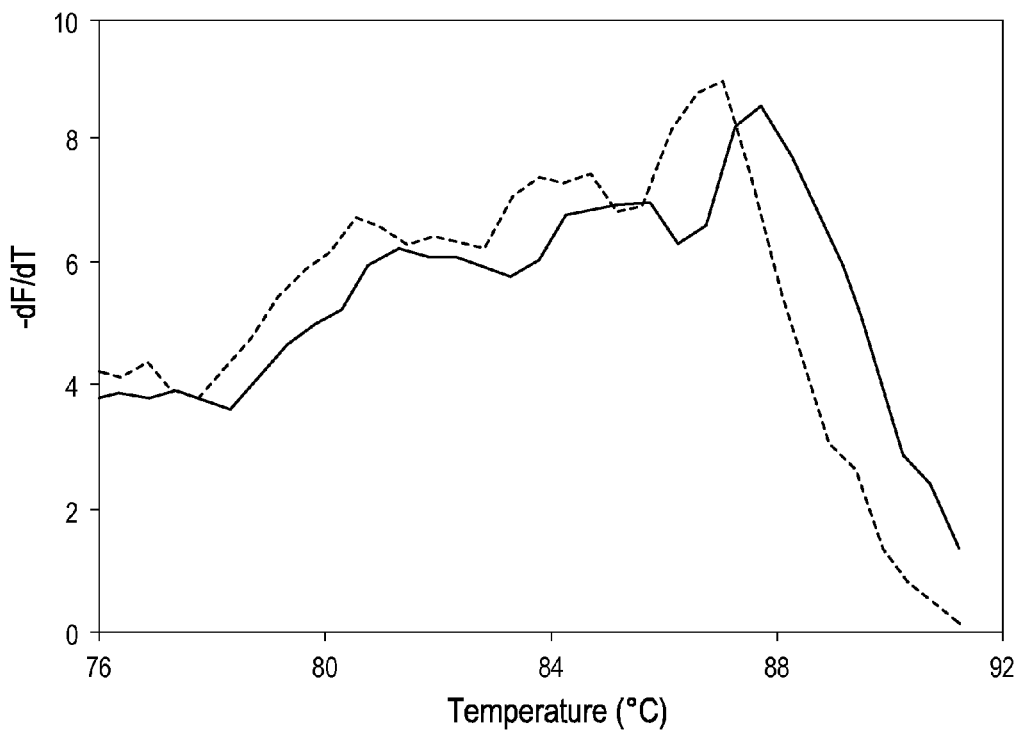
FIGS. 17A-17B illustrate negative derivative plots of melting curves generated on the LightCycler® 480 using solution (dashed lines) and instrument (solid lines) temperatures at 0.14° C./s (FIG. 17A) and 0.01° C./s (FIG. 17B).
Figure 17B:
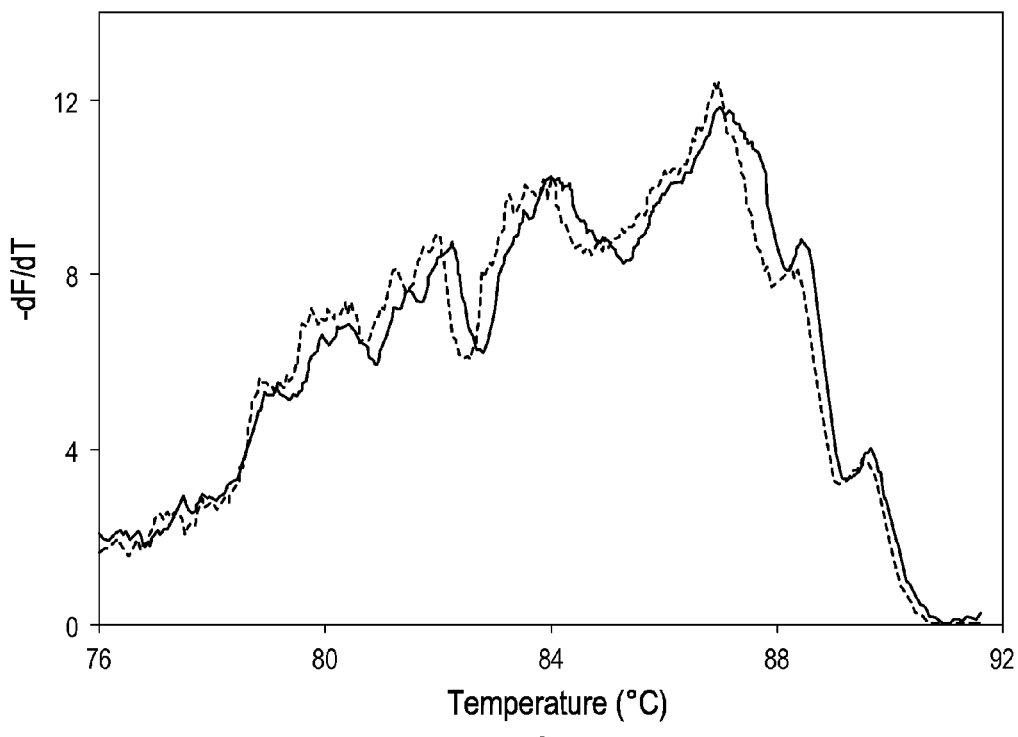

In at least one illustrative embodiment, the accuracy of melting curve analysis may be discerned by contrasting solution verses instrument temperatures (see FIGS. 17A-17B). For example, negative derivative plots of melting curves may be generated on a LightCycler® 480 using solution (dashed lines) and instrument (solid lines) temperatures at (FIG. 17A) 0.14° C./s) and (FIG. 17B) 0.01° C./s. The illustrative 96-well, Class I instrument may enable simultaneous collection of both DNA helicity and solution temperature in separate fluorescence channels. In some embodiments, Lambda DNA helicity may be visualized by the DNA dye LCGreen® Plus and solution temperatures may be determined by sulforhodamine B fluorescence. Similarly, a volume of 20 μL without oil overlay may be used according to manufacturer's recommendations. In certain illustrative embodiments, at a rate of 0.14° C./s, the melting curve derived from instrument temperatures may be 1.1° C. higher than curves derived from solution temperatures. At 0.01° C./s, this lag may be reduced approximately 5-fold to 0.2° C. Therefore, the solution temperatures may be said to lag behind instrument temperatures by 1.1° C. at 0.14° C./s and 0.2° C. at 0.01° C./s.

Given the observed temperature lag during heating and cooling, it is not surprising that hold times are often required by commercial cyclers during thermal cycling so that the temperature of the sample has enough time to reach the target temperatures of annealing, denaturation and extension. Reflecting this limitation, in certain embodiments, the only commercial cyclers to allow 0 s "hold" times are the most responsive, circulating air/capillary thermal cyclers. Minimum allowed hold times on other instruments may range from 1-10 s, even though hold times may not be necessary if the target temperatures are reached. Even with these required hold times, however, target temperatures may seldom be attained. For example, solution temperatures after the required annealing holds may range from 1-5° C. above the target temperature. After required denaturation holds, solution temperatures on some instruments may be more than 8° C. below target. While target temperatures may not be reached using minimum programmable holding times, solution temperatures may eventually stabilize to target temperatures in certain illustrative embodiments (see FIG. 14).

This time delay may elevate the apparent temperatures of melting curves to an extent that appears to depend on the rate of heating. This error can exceed 1° C. on common instruments at typical melting rates (see FIGS. 17A-17B). An increase in apparent melting temperature with increasing melting rate may accurately reflect the kinetics of DNA melting. Another explanation for this apparent correlation is an artifact resulting from an unintentional mismatch between the sample and instrument temperatures. Thus, current real-time instruments may inadequately control and/or record solution temperatures accurately during cycling, and errors may increase as cycle times become shorter. Temperature calibration is typically performed at equilibrium temperatures, not while the temperature is changing as occurs during PCR. Hence, simple re-calibration often will not improve the dynamic temperature errors revealed here. This may help explain the common perception that PCR protocols are not transferable between instrument brands. Better solution temperatures can be obtained during cycling by matching the thermal response of the sensor to the sample, or by using the methods described herein.

Once again using the custom multicolor fluorimeter, methods using one or two emission bands were examined for sulforhodamine B (acid form). Increased temperature accuracy was achieved with two spectral bands. The maximum temperature difference between the thermocouple and two-color analysis was 0.3° C., compared to 0.6° C. with a single-color. Implementation of a fluorescence ratio decreased the error by about a factor of 2.

Single nucleotide variants were successfully amplified using fluorescence-based temperature control using sulforhodamine B on the modified LightCycler 24. Quantification cycles ($C_q$) values in the low 20 s suggest efficient amplification, even when holding times of 10 s, or even when minimal "0" s holds are used. It is noted that zero second holding times may benefit from higher primer concentrations to speed the annealing process, as discussed further in C. T. Wittwer, K. Ririe, R. Rasmussen, in: F. Ferre (Ed.), Gene Quantification, Birkhauser, New York, 1998. pp. 129-144, the entirety of which is herein incorporated by reference. Accurate temperature cycling allows cycle times to be minimized, as equilibrium holding times (imposed to allow the solution temperature to "catch up" to instrument readings) can be reduced or eliminated altogether.

In a 35 cycle comparison of fluorescence- and thermocouple-based temperature cycling control, the average difference between temperature measurements was 0.5±0.4° C. These results show that fluorescence-based temperature control produced reproducible results across all 35 cycles. When differences at annealing and denaturation were considered, these differences were 0.3±0.2° C. and 0.9±0.3° C., respectively. Thus, the fluorescence-based temperature tracks well with thermocouple measurements, particularly at lower temperatures. The larger (and consistent) discrepancy at denaturation suggests a systematic source of error that occurs at higher temperature. Inherently, the amount of fluorescence change per ° C. for sulforhodamine B (monosodium salt) is lower at higher temperatures.

When absolute differences between temperature measurements and setpoint temperatures were compared at denaturation and annealing, the fluorescence-based temperature met target temperatures better than instrument determined temperatures. Average fluorescence-based and setpoint temperature differences were 0.4±0.2° C. and 0.4±0.3° C. at annealing and denaturation, respectively. When thermocouple and setpoint temperatures were compared, these values increased to 0.6±0.3° C. and 1.1±0.5° C. for annealing and denaturation, respectively.

The use of fluorescence as a temperature monitor provides a noninvasive method of assessing the actual, average solution temperature that should remain robust even at the most rapid cycling speeds. Fluorescent monitoring of a passive reference dye, illustratively, to assess sample temperatures can improve PCR and melting analysis. By directly monitoring the solution temperature, errors at denaturation and annealing can be documented and correlated to efficiency, yield, and specificity by (1) making note of any abnormalities during heating or cooling; (2) observing unexpected results in efficiency, yield, and/or specificity; and (3) correlating the unexpected result with the abnormality. Furthermore, cycle times can be minimized and instrument performance validated on a run-by-run and sample-by-sample basis. The need to increase the accuracy of both quantitative real-time PCR and melting analysis require greater and greater temperature accuracy. For example, the success of high resolution melting analysis for both genotyping and variant scanning may depend on temperature accuracies <1° C. Determining solution temperatures by fluorescence is a viable and non-intrusive method for addressing temperature measurement issues during PCR and high-resolution melting analysis.

It is noted that products, processes, devices, systems, mixtures, and methods according to certain embodiments of the present invention may include, incorporate, or otherwise comprise properties, features, components, members, and/or elements described in other embodiments, including systems, methods, products, devices, and/or embodiments of the same disclosed herein. Thus, reference to a specific feature in relation to one embodiment should not be construed as being limited to applications only within said embodiment.

While various aspects and embodiments have been disclosed herein, other aspects and embodiments are contemplated. The various aspects and embodiments disclosed herein are for purposes of illustration and are not intended to be limiting. Additionally, the words "including," "having," "involving" and variants thereof (e.g., "includes," "has," and "involves") as used herein, including the claims, shall be open ended and have the same meaning as the word "comprising" and variants thereof (e.g., "comprise" and "comprises").

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached invention disclosure for purposes of illustrating the invention, it will be apparent to those skilled in the art that various changes in the methods and apparatus disclosed herein may be made without departing from the scope of the invention, which is defined in the appended claims. All changes which come within the meaning and range of equivalency of the claims are to be embraced within their scope.

We claim:

1. A method of measuring a temperature of a sample, comprising:
providing a sample that includes:
a nucleic acid;
a temperature-sensitive fluorescent dye that, in response to a stimulus, emits a temperature-sensitive fluorescent signal that:
in the presence of the nucleic acid, is not directly proportional to an amount of the nucleic acid present in the sample, is not affected by dsDNA denaturation, or is substantially independent of the amount of the nucleic acid present in the sample; and
changes as a function of temperature in a known manner; and
a second fluorescent dye that produces a second fluorescent signal,
wherein the second fluorescent signal is indicative of the amount of the nucleic acid present in the sample;
exciting the temperature-sensitive fluorescent dye to induce emission of the temperature-sensitive fluorescent signal;
measuring the temperature-sensitive fluorescent signal emitted from the temperature-sensitive fluorescent dye; and
determining a fluorescence-determined temperature of the sample based on the temperature-sensitive fluorescent signal emitted by the temperature-sensitive fluorescent dye.

2. The method as recited in claim 1, wherein the temperature-sensitive fluorescent dye comprises sulforhodamine B.

3. The method as recited in claim 1, wherein exciting the temperature-sensitive fluorescent dye comprises exposing the temperature-sensitive fluorescent dye to electromagnetic radiation light having a wavelength sufficient to induce emission of the temperature-sensitive fluorescent signal.

4. The method as recited in claim 1, wherein the sample comprises an aqueous solution.

5. The method as recited in claim 1, wherein the sample comprises a suspension.

6. The method as recited in claim 1, wherein the sample comprises a PCR mixture.

7. The method as recited in claim 6, further comprising measuring fluorescence emitted from the sample at one or more time points during PCR cycling.

8. The method as recited in claim 6, further comprising controlling thermal cycling of the PCR mixture in accordance with a thermocycling profile by using feedback control, wherein a predetermined value of the temperature-sensitive fluorescent signal indicates an appropriate time to initiate a change to a next phase in the thermocycling profile,
wherein the predetermined value is selected from the group consisting of: emission intensity of the temperature-sensitive fluorescent signal, a temperature calculated from the emission intensity of the temperature-sensitive fluorescent signal, and a value or parameter calculated from the emission intensity of the temperature-sensitive fluorescent signal, and
wherein the next phase is selected from the group consisting of: a start of a programmed temperature hold period for the PCR mixture; an end of the programmed temperature hold period for the PCR mixture; ramping to a predetermined temperature.

9. The method as recited in claim 1, wherein variance between the temperature of the sample as determined based on the temperature-sensitive fluorescent signal emitted by the temperature-sensitive fluorescent dye and a temperature measured through direct contact of the sample that includes the temperature-sensitive fluorescent dye is less than or equal to 1 degree Celsius.

10. The method as recited in claim 1, wherein an intensity of the temperature-sensitive fluorescent signal emitted from the temperature-sensitive fluorescent dye is substantially independent of the amount of the nucleic acid present in the sample.

11. The method as recited in claim 1, wherein the temperature-sensitive fluorescent dye is not a dsDNA binding dye, the temperature-sensitive fluorescent dye is not tethered to a nucleic acid, and the temperature-sensitive fluorescent signal of the temperature-sensitive fluorescent dye is not affected by dsDNA denaturation.

12. The method as recited in claim 1, wherein
the second fluorescent signal is indicative of an amount of double-stranded nucleic acid present,
the determining step takes place while melting the nucleic acid and measuring the signal indicative of the amount of double-stranded nucleic acid present, and
further including the step of generating a melting curve based on the second fluorescent signal, the melting curve being adjusted based on the fluorescence-determined temperature.

13. The method as recited in claim 1, wherein the determining step includes generating a ratio of the temperature-sensitive fluorescent signal to a signal from the sample that is generally temperature insensitive.

14. The method of claim 13, wherein the temperature-sensitive fluorescent signal is at a first wavelength, and the signal that is generally temperature insensitive is a signal from the temperature-sensitive fluorescent dye at a second wavelength.

15. The method of claim 13, wherein the signal that is generally temperature insensitive is the second fluorescent signal.

16. The method as recited in claim 1, wherein an intensity of the temperature-sensitive fluorescent signal emitted from the temperature-sensitive fluorescent dye is not directly proportional to the amount of the nucleic acid present in the sample.

17. The method as recited in claim 1, wherein an intensity of the temperature-sensitive fluorescent signal emitted from the temperature-sensitive fluorescent dye is not affected by dsDNA denaturation.

18. The method as recited in claim 1, wherein a wavelength at which the temperature-sensitive fluorescent signal is emitted from the temperature-sensitive fluorescent dye is not directly proportional to the amount of the nucleic acid present in the sample.

19. The method as recited in claim 1, wherein a wavelength at which the temperature-sensitive fluorescent signal is emitted from the temperature-sensitive fluorescent dye is not affected by dsDNA denaturation.

20. The method as recited in claim 1, wherein the sample includes-complementary strands of the nucleic acid and the step of determining a fluorescence-determined temperature of the sample takes place while melting the double-stranded nucleic acid and measuring the signal indicative of the amount of double-stranded nucleic acid present in the sample.

21. The method as recited in claim 20, wherein the controlling thermal cycling step comprises:
    changing the temperature of the PCR mixture from a first temperature to a second temperature;
    exciting the temperature-sensitive fluorescent dye to induce emission of the temperature-sensitive fluorescent signal therefrom;
    detecting the temperature-sensitive fluorescent signal emitted by the temperature-sensitive fluorescent dye; and
    changing to the next phase in the thermocycling profile upon detecting the predetermined value of the temperature-sensitive fluorescent signal.

22. The method as recited in claim 1, wherein the second fluorescent dye is a dsDNA binding dye.

23. A method of measuring a temperature of a sample, comprising:
    providing a sample that includes:
        a nucleic acid;
        a temperature-sensitive fluorescent dye that, in response to a stimulus, emits a temperature-sensitive fluorescent signal that:
            in the presence of the nucleic acid, is not directly proportional to an amount of the nucleic acid present in the sample, is not affected by dsDNA denaturation, or is substantially independent of the amount of the nucleic acid present in the sample; and
            changes as a function of temperature in a known manner; and
        a second fluorescent dye that produces a second fluorescent signal,
    wherein the second fluorescent signal is indicative of an amount of double-stranded nucleic acid present in the sample;
    exciting the temperature-sensitive fluorescent dye to induce emission of the temperature-sensitive fluorescent signal;
    measuring the temperature-sensitive fluorescent signal emitted from the temperature-sensitive fluorescent dye;
    determining a fluorescence-determined temperature of the sample based on the temperature-sensitive fluorescent signal emitted by the temperature-sensitive fluorescent dye while melting the nucleic acid and measuring the signal indicative of the amount of double-stranded nucleic acid present; and
    generating a melting curve based on the second fluorescent signal, the melting curve being adjusted based on the fluorescence-determined temperature, wherein the melting curve is generated using the formula $$T = \frac{1}{\frac{\ln(I/I_{ref})}{C} + (1/T_{ref})}$$

wherein I is a measured fluorescent intensity of the temperature-sensitive reagent at T temperature, $I_{ref}$ is a fluorescent intensity at a reference temperature $T_{ref}$, and C is a calibration constant equal to $$\ln\left(\frac{1}{I_{ref}}\right) / \left(\frac{1}{T} - \frac{1}{T_{ref}}\right).$$

24. The method as recited in claim 23, wherein the melting curve is displayed as a derivative melting plot.

25. A method of calibrating a sample heating device, comprising:
    disposing a sample in the sample heating device, the sample including a temperature-sensitive fluorescent dye that, in response to a stimulus, emits a temperature-sensitive fluorescent signal that:
        in the presence of a nucleic acid, is not directly proportional to an amount of the nucleic acid, is not affected by dsDNA denaturation, or is substantially independent of the amount of the nucleic acid; and
        changes as a function of temperature in a known and predictable manner;
    stimulating the temperature-sensitive fluorescent dye to induce emission of the temperature-sensitive fluorescent signal therefrom;
    determining a fluorescence-determined temperature of the sample based on the temperature-sensitive fluorescent signal emitted by the temperature-sensitive fluorescent dye;
    determining a device-determined temperature for the sample; and
    adjusting a temperature setting of the sample heating device based on at least the fluorescence-determined temperature.

26. The method as recited in claim 25, wherein the temperature-sensitive fluorescent dye is a passive reference reagent.

27. The method as recited in claim 25, wherein the intensity of temperature-sensitive fluorescent signal emitted by the temperature-sensitive reagent is not affected by dsDNA denaturation.

28. The method as recited in claim 25, wherein the sample comprises a suspension.

29. The method as recited in claim 25, wherein the sample comprises an aqueous solution.

30. The method as recited in claim 25, wherein the temperature-sensitive fluorescent dye comprises sulforhodamine B.

31. The method as recited in claim 25, wherein stimulating the temperature-sensitive fluorescent dye comprises exciting the fluorescent dye with electromagnetic radiation.

32. The method as recited in claim 25, wherein the device-determined temperature for the sample is measured without directly contacting the sample.

33. The method as recited in claim 25, wherein the device-determined temperature for the sample is measured through direct contact with the sample.

34. The method as recited in claim 25, wherein variance between the fluorescence-determined temperature and a temperature measured through direct contact of a sample that includes the temperature-sensitive fluorescent dye is less than or equal to 1 degree Celsius.

35. A thermocycling system configured to employ temperature-dependent fluorescence as an indication of internal sample temperature, the system comprising:
 a sample vessel having an aqueous sample disposed therein, the aqueous sample comprising an amount of a nucleic acid and a temperature-sensitive fluorescent dye that, in response to a stimulus, emits a temperature-sensitive fluorescent signal that:
  in the presence of a nucleic acid, is not directly proportional to the amount of the nucleic acid present in the sample, is not affected by dsDNA denaturation, or is substantially independent of the amount of the nucleic acid present in the sample; and
  changes as a function of temperature in a known manner;
 a sample temperature controlling device configured to manipulate a temperature of the sample;
 a sample temperature control mechanism configured to utilize the sample temperature controlling device to regulate the temperature of the sample;
  wherein the sample temperature control mechanism comprises a sample temperature raising mechanism and a sample temperature lowering mechanism; and
 a sample fluorescence measuring element configured to quantify fluorescence of the sample;
  wherein the sample temperature control mechanism regulates the temperature of the sample based on the fluorescence of the sample.

36. The thermocycling system as recited in claim 35, further comprising a sample temperature measuring device.

37. The thermocycling system as recited in claim 36, wherein the sample temperature measuring device measures a temperature of the sample without directly contacting said sample.

38. The thermocycling system as recited in claim 35, wherein the sample temperature measuring device measures a temperature of the sample through direct contact with said sample.

39. The thermocycling system as recited in claim 35, wherein the sample temperature controlling device is configured to raise the temperature of the sample by exposing the sample vessel to matter having a temperature greater than the temperature of the sample.

40. The thermocycling system as recited in claim 35, wherein the sample temperature control mechanism involves moving the sample among a plurality of sample temperature controlling devices.

41. The thermocycling system as recited in claim 35, wherein the sample temperature control mechanism involves changing the temperature of matter associated with the sample temperature controlling device.

42. The thermocycling system as recited in claim 35, wherein the sample fluorescence measuring element comprises an optical member configured to query the fluorescence of the sample.

43. The thermocycling system as recited in claim 35, further comprising a CPU that executes instructions to operate the sample temperature controlling mechanism based on one or more of: sample fluorescence and a value or parameter calculated from sample fluorescence.

44. The thermocycling system as recited in claim 35, further comprising a sample fluorescence stimulating element configured to induce temperature-sensitive fluorescence from the sample.

45. The thermocycling system as recited in claim 35, wherein the sample comprises a PCR sample mixture.

46. A PCR mixture, comprising:
 an aqueous fluid; and, disposed in the aqueous fluid:
  a nucleic acid; and
  a temperature-sensitive fluorescent dye that emits, in response to a stimulus, a fluorescent signal that:
   in the presence of a nucleic acid, is not directly proportional to an amount of the nucleic acid present in the sample, is not affected by dsDNA denaturation, or is substantially independent of an amount of the nucleic acid present in the sample; and
   changes between 95° C. and 50° C. as a function of temperature in a known manner.

47. The PCR mixture as recited in claim 46, wherein the fluorescent signal increases by about 50% between 95° C. and 50° C.

48. The PCR mixture as recited in claim 46, wherein the temperature-sensitive fluorescent dye comprises sulforhodamine B.

49. The PCR mixture as recited in claim 46, further comprising a nucleic acid polymerase.

50. The PCR mixture as recited in claim 46, further comprising one or more dNTPs.

51. The PCR mixture as recited in claim 46, further comprising a plurality of nucleic acid primers configured to anneal to a portion of the nucleic acid.

52. The PCR mixture as recited in claim 46, further comprising a quantitative indicator of PCR product formation, wherein the quantitative indicator of PCR product formation comprises a fluorescent dye.

53. The PCR mixture as recited in claim 52, wherein the quantitative indicator of PCR product formation comprises a double-stranded DNA-binding reagent.

54. The PCR mixture as recited in claim 46, wherein the temperature-sensitive fluorescent dye displays a temperature sensitivity of about 1%/° C.

55. The PCR mixture as recited in claim 46, wherein the temperature-sensitive fluorescent dye is not a dsDNA binding dye and is not tethered to a nucleic acid.

56. A method of controlling thermal cycling through a thermocycling profile of a sample using feedback control, the method comprising:
 providing a sample at a first temperature, wherein the sample includes a temperature-sensitive fluorescent dye that, in response to a stimulus, emits a temperature-sensitive fluorescent signal that:
  in the presence of a nucleic acid, is not directly proportional to an amount of the nucleic acid present in the sample, is not affected by dsDNA denaturation, or is substantially independent of an amount of the nucleic acid present in the sample; and
  changes as a function of temperature in a known manner;
 stimulating the temperature-sensitive fluorescent dye to induce emission of the temperature-sensitive fluorescent signal therefrom;
 detecting the temperature-sensitive fluorescent signal emitted by the temperature-sensitive fluorescent dye; and
 changing to a next phase in the thermocycling profile upon detecting a predetermined value of the temperature-sensitive fluorescent signal, wherein the predetermined value of the temperature-sensitive fluorescent signal indicates an appropriate time to initiate the change to the next phase in the thermocycling profile.

57. The method as recited in claim 56 wherein the predetermined value is selected from the group consisting of an intensity of the temperature-sensitive fluorescent signal, a temperature calculated from the temperature-sensitive fluorescent signal, and a value or parameter calculated from the temperature-sensitive fluorescent signal.

58. The method as recited in claim 56 wherein the next phase is selected from the group consisting of: a start of a programmed temperature hold period for the sample; an end of the programmed temperature hold period for the sample; ramping to a second temperature; and ramping to the first temperature.

59. The method as recited in claim 56 wherein the sample comprises a PCR mixture.

60. The method as recited in claim 56 further comprising:
providing a thermal cycling device programmed with the thermocycling profile; and
placing the sample in a sample vessel in the thermal cycling device.

\* \* \* \* \*

SEQUENCE LISTING

```
<160> NUMBER OF SEQ ID NOS: 8

<210> SEQ ID NO 1
<211> LENGTH: 24
<212> TYPE: DNA
<213> ORGANISM: Homo sapiens

<400> SEQUENCE: 1
ggttcccaat aaaagtgact ctag                                              24

<210> SEQ ID NO 2
<211> LENGTH: 18
<212> TYPE: DNA
<213> ORGANISM: Homo sapiens

<400> SEQUENCE: 2
ctgagcccag agagctgc                                                     18

<210> SEQ ID NO 3
<211> LENGTH: 21
<212> TYPE: DNA
<213> ORGANISM: Homo sapiens

<400> SEQUENCE: 3
ccactgcact gaagtataag t                                                 21

<210> SEQ ID NO 4
<211> LENGTH: 21
<212> TYPE: DNA
<213> ORGANISM: Homo sapiens

<400> SEQUENCE: 4
ttagcagagt gtgacaaaaa a                                                 21

<210> SEQ ID NO 5
<211> LENGTH: 24
<212> TYPE: DNA
<213> ORGANISM: Homo sapiens

<400> SEQUENCE: 5
aagatggagt caacatttta caag                                              24

<210> SEQ ID NO 6
<211> LENGTH: 19
<212> TYPE: DNA
<213> ORGANISM: Homo sapiens

<400> SEQUENCE: 6
gatgactgag gtcaacgag                                                    19

<210> SEQ ID NO 7
<211> LENGTH: 30
<212> TYPE: DNA
<213> ORGANISM: Homo sapiens

<400> SEQUENCE: 7
aggatgtttg tttatattat ttctaactca                                        30

<210> SEQ ID NO 8
<211> LENGTH: 22
<212> TYPE: DNA
<213> ORGANISM: Homo sapiens
```

```
<400> SEQUENCE: 8
ctactccctc ataatgtaat gc                                          22
```